US012661103B2

(12) United States Patent
Fleischman et al.

(10) Patent No.: US 12,661,103 B2
(45) Date of Patent: Jun. 23, 2026

(54) SUTURE-LOCKING WASHER FOR USE WITH A BONE ANCHOR, AND METHOD FOR SUPPORTING THE THUMB OF A PATIENT AFTER BASAL JOINT ARTHROPLASTY, AND OTHER NOVEL ORTHOPEDIC APPARATUS AND OTHER NOVEL ORTHOPEDIC PROCEDURES

(71) Applicant: Simparo Inc., Norristown, PA (US)

(72) Inventors: Sidney Fleischman, Durham, NC (US);
James Whayne, Chapel Hill, NC (US);
Izi Bruker, Newton, MA (US); Jeanne L. DelSignore, Rushville, NY (US);
Kevin L. Ohashi, Jamaica Plain, MA (US); James Christopher Harber, Shorewood, MN (US)

(73) Assignee: Simparo Inc., Norristown, PA (US)

( * ) Notice: Subject to any disclaimer, the term of this patent is extended or adjusted under 35 U.S.C. 154(b) by 150 days.

(21) Appl. No.: 17/978,589

(22) Filed: Nov. 1, 2022

(65) Prior Publication Data

US 2023/0293164 A1 Sep. 21, 2023

Related U.S. Application Data

(63) Continuation of application No. 15/999,085, filed on Aug. 16, 2018, now Pat. No. 11,484,301, which is a
(Continued)

(51) Int. Cl.
*A61B 17/04* (2006.01)
*A61B 17/86* (2006.01)
(Continued)

(52) U.S. Cl.
CPC ...... *A61B 17/0401* (2013.01); *A61B 17/0487* (2013.01); *A61B 17/8695* (2013.01);
(Continued)

(58) Field of Classification Search
CPC ............ A61B 17/0487; A61B 17/8695; A61B 2017/0448; A61B 2017/0456; A61B 2017/0462
See application file for complete search history.

(56) References Cited

U.S. PATENT DOCUMENTS

| | | | |
|---|---|---|---|
| 2,416,260 A | 2/1947 | Karle | |
| 2,579,192 A | 12/1951 | Kohl et al. | |

(Continued)

FOREIGN PATENT DOCUMENTS

| | | |
|---|---|---|
| WO | WO 2006/034719 | 4/2006 |
| WO | WO 2007/002071 | 1/2007 |
| WO | WO 2010/047981 | 4/2010 |

OTHER PUBLICATIONS

Badia, Alejandro, Surgical Options for Thumb Basal Joint Arthritis, US Musculoskeletal Review, 2006, pp. 69-70.
(Continued)

*Primary Examiner* — Alexander J Orkin
(74) *Attorney, Agent, or Firm* — Pandiscio & Pandiscio

(57) ABSTRACT

The invention provides surgical methods, devices, apparatus, and systems for supporting the thumb of a patient after basal joint arthroplasty. The embodiments of the invention comprise at least one index metacarpal anchor, at least one thumb metacarpal anchor, at least one sling for positioning the thumb metacarpal anchor relative to the index metacarpal anchor, and at least one anchor washer for tightening and securing the sling(s) without the need to tie the suture(s) components of the sling(s) into knots. Index and thumb metacarpal anchors comprise at least one bone-engaging element for engaging the respective metacarpal. The anchor washer may incorporate one or more sling-engagement mechanisms. Increasing the number of sling-engagement mechanisms associated with the anchor washer increases the surface area of the sling(s) and provides multiple sling
(Continued)

elements to provide redundancy and increase the pull force of the sling(s) attachment(s) used to affix the thumb and index metacarpal anchors into a position relative to each other.

14 Claims, 44 Drawing Sheets

Related U.S. Application Data continuation-in-part of application No. 14/596,973, filed on Jan. 14, 2015, now Pat. No. 10,278,692.

(60) Provisional application No. 62/546,187, filed on Aug. 16, 2017, provisional application No. 61/927,309, filed on Jan. 14, 2014.

(51) Int. Cl.
  *A61F 2/08* (2006.01)
  *A61F 2/42* (2006.01)
  *A61B 17/56* (2006.01)
  *A61F 2/30* (2006.01)

(52) U.S. Cl.
  CPC .......... *A61F 2/0811* (2013.01); *A61F 2/4202* (2013.01); *A61F 2/4241* (2013.01); *A61B 2017/0409* (2013.01); *A61B 2017/0414* (2013.01); *A61B 2017/044* (2013.01); *A61B 2017/0448* (2013.01); *A61B 2017/0456* (2013.01); *A61B 2017/0459* (2013.01); *A61B 2017/0462* (2013.01); *A61B 2017/565* (2013.01); *A61B 2017/567* (2013.01); *A61F 2002/0829* (2013.01); *A61F 2002/0864* (2013.01); *A61F 2002/0882* (2013.01); *A61F 2002/0888* (2013.01); *A61F 2002/30461* (2013.01); *A61F 2002/30672* (2013.01); *A61F 2002/3085* (2013.01); *A61F 2002/30998* (2013.01); *A61F 2002/4253* (2013.01)

(56) References Cited

U.S. PATENT DOCUMENTS

| | | | |
|---|---|---|---|
| 2,808,055 A | 10/1957 | Thayer | |
| 3,496,940 A | 2/1970 | Steinman | |
| 3,545,008 A | 12/1970 | Bader, Jr. | |
| 3,745,590 A | 7/1973 | Stubstad | |
| 3,805,300 A | 4/1974 | Tascon-Alonso et al. | |
| 4,187,558 A | 2/1980 | Dahlen et al. | |
| 4,408,938 A | 10/1983 | Maguire | |
| 4,484,570 A | 11/1984 | Sutter et al. | |
| 4,492,226 A | 1/1985 | Belykh et al. | |
| 4,590,928 A | 5/1986 | Hunt et al. | |
| 4,713,075 A | 12/1987 | Kurland | |
| 4,741,330 A | 5/1988 | Hayhurst | |
| 4,775,380 A | 10/1988 | Seedhom et al. | |
| 4,778,468 A | 10/1988 | Hunt et al. | |
| 4,779,616 A | 10/1988 | Johnson | |
| 4,870,957 A | 10/1989 | Goble et al. | |
| 4,871,289 A | 10/1989 | Choiniere | |
| 4,927,421 A | 5/1990 | Goble et al. | |
| 5,037,422 A | 8/1991 | Hayhurst et al. | |
| 5,046,513 A | 9/1991 | Gattuma et al. | |
| 5,207,679 A | 5/1993 | Li | |
| 5,209,753 A | 5/1993 | Biedermann et al. | |
| 5,224,946 A | 7/1993 | Hayhurst et al. | |
| 5,226,426 A | 7/1993 | Yoon | |
| 5,236,445 A | 8/1993 | Hayhurst et al. | |
| 5,258,015 A * | 11/1993 | Li ........................ A61B 17/685 |
| | | | 24/453 |
| 5,268,001 A | 12/1993 | Nicholson et al. | |
| 5,324,308 A | 6/1994 | Pierce | |

| | | | |
|---|---|---|---|
| 5,336,240 A | 8/1994 | Metzler et al. | |
| 5,354,298 A | 10/1994 | Lee et al. | |
| 5,417,712 A | 5/1995 | Whittaker et al. | |
| 5,423,860 A | 6/1995 | Lizardi et al. | |
| 5,464,427 A | 11/1995 | Curtis et al. | |
| 5,480,403 A | 1/1996 | Lee et al. | |
| 5,486,197 A | 1/1996 | Le et al. | |
| 5,501,695 A | 3/1996 | Anspach, Jr. et al. | |
| 5,522,844 A | 6/1996 | Johnson | |
| 5,522,845 A | 6/1996 | Wenstrom, Jr. | |
| 5,534,012 A | 7/1996 | Bonutti | |
| 5,545,180 A | 8/1996 | Le et al. | |
| 5,569,306 A | 10/1996 | Thal | |
| 5,584,835 A | 12/1996 | Greenfield | |
| 5,601,558 A | 2/1997 | Torrie et al. | |
| 5,611,515 A | 3/1997 | Benderev et al. | |
| 5,632,748 A | 5/1997 | Beck, Jr. et al. | |
| 5,643,321 A | 7/1997 | McDevitt | |
| 5,645,589 A | 7/1997 | Li | |
| 5,649,963 A | 7/1997 | McDevitt | |
| 5,658,313 A | 8/1997 | Thal | |
| 5,662,658 A | 9/1997 | Wenstrom, Jr. | |
| 5,665,112 A | 9/1997 | Thal | |
| 5,681,320 A | 10/1997 | McGuire | |
| 5,683,419 A | 11/1997 | Thal | |
| 5,690,649 A | 11/1997 | Li | |
| 5,702,215 A | 12/1997 | Li | |
| 5,702,397 A | 12/1997 | Goble et al. | |
| 5,702,422 A | 12/1997 | Stone | |
| 5,702,468 A | 12/1997 | Goldberg | |
| 5,707,395 A | 1/1998 | Li | |
| 5,709,708 A | 1/1998 | Thal | |
| 5,716,368 A | 2/1998 | de la Torre et al. | |
| 5,725,529 A | 3/1998 | Nicholson et al. | |
| 5,725,541 A | 3/1998 | Anspach, III et al. | |
| 5,728,136 A | 3/1998 | Thal | |
| 5,741,300 A | 4/1998 | Li | |
| 5,741,301 A | 4/1998 | Pagedas | |
| 5,782,863 A | 7/1998 | Bartlett | |
| 5,782,864 A | 7/1998 | Lizardi | |
| 5,797,963 A | 8/1998 | McDevitt | |
| 5,814,071 A | 9/1998 | McDevitt et al. | |
| 5,814,072 A | 9/1998 | Bonutti | |
| 5,814,073 A | 9/1998 | Bonutti | |
| 5,843,127 A | 12/1998 | Li | |
| 5,845,645 A | 12/1998 | Bonutti | |
| 5,849,004 A | 12/1998 | Bramlet | |
| 5,860,978 A | 1/1999 | McDevitt et al. | |
| 5,906,624 A | 5/1999 | Wenstrom, Jr. | |
| 5,911,721 A | 6/1999 | Nicholson et al. | |
| 5,928,244 A | 7/1999 | Tovey et al. | |
| 5,935,129 A | 8/1999 | McDevitt et al. | |
| 5,935,134 A | 8/1999 | Pedlick et al. | |
| 5,957,953 A | 9/1999 | DiPoto et al. | |
| 5,968,044 A | 10/1999 | Nicholson et al. | |
| 5,980,558 A | 11/1999 | Wiley | |
| 5,980,559 A | 11/1999 | Bonutti | |
| 5,993,459 A | 11/1999 | Larsen et al. | |
| 6,010,447 A | 1/2000 | Kardjian | |
| 6,015,428 A * | 1/2000 | Pagedas ............... A61B 17/062 |
| | | | 606/232 |
| 6,041,485 A | 3/2000 | Pedlick et al. | |
| 6,042,534 A | 3/2000 | Gellman et al. | |
| 6,045,573 A | 4/2000 | Wenstrom, Jr. et al. | |
| 6,056,772 A | 5/2000 | Bonutti | |
| 6,066,160 A | 5/2000 | Colvin et al. | |
| 6,083,522 A | 7/2000 | Chu et al. | |
| 6,086,608 A | 7/2000 | Ek et al. | |
| 6,099,547 A | 8/2000 | Geltman et al. | |
| 6,110,101 A | 8/2000 | Tihon et al. | |
| 6,117,144 A | 9/2000 | Nobles et al. | |
| 6,149,653 A | 11/2000 | Deslauriers | |
| 6,168,598 B1 | 1/2001 | Martello | |
| 6,245,082 B1 | 6/2001 | Gellman et al. | |
| 6,267,766 B1 | 7/2001 | Burkhart | |
| 6,312,448 B1 | 11/2001 | Bonutti | |
| 6,319,269 B1 | 11/2001 | Li | |
| 6,368,326 B1 | 4/2002 | Dakin et al. | |
| 6,506,190 B1 | 1/2003 | Walshe | |

(56)                 References Cited

U.S. PATENT DOCUMENTS

| | | | |
|---|---|---|---|
| 6,517,578 | B2 | 2/2003 | Hein |
| 6,524,316 | B1 | 2/2003 | Nicholson et al. |
| 6,527,794 | B1 | 3/2003 | McDevitt et al. |
| 6,527,795 | B1 | 3/2003 | Lizardi |
| 6,544,281 | B2 | 4/2003 | ElAttrache et al. |
| 6,562,071 | B2 | 5/2003 | Järvinen |
| 6,575,987 | B2 | 6/2003 | Gellman et al. |
| 6,641,596 | B1 | 11/2003 | Lizardi |
| 6,660,023 | B2 | 12/2003 | McDevitt et al. |
| 6,669,697 | B1 * | 12/2003 | Pisharodi ............. A61B 17/701 |
| | | | 606/264 |
| 6,673,094 | B1 | 1/2004 | McDevitt et al. |
| 6,775,928 | B2 | 8/2004 | Grande et al. |
| 6,872,227 | B2 | 3/2005 | Sump et al. |
| 7,073,279 | B2 | 7/2006 | Min |
| 7,083,568 | B2 | 8/2006 | Neisz et al. |
| 7,938,847 | B2 | 5/2011 | Fanton et al. |
| 8,398,678 | B2 | 3/2013 | Baker et al. |
| 8,439,976 | B2 | 5/2013 | Albertorio et al. |
| 8,460,319 | B2 | 6/2013 | Wales et al. |
| 8,512,376 | B2 | 8/2013 | Thornes |
| 8,721,650 | B2 | 5/2014 | Fanton et al. |
| 8,753,375 | B2 | 6/2014 | Albertorio |
| 8,758,406 | B2 | 6/2014 | Fanton et al. |
| 8,888,815 | B2 | 11/2014 | Holmes, Jr. |
| 9,023,083 | B2 | 5/2015 | Foerster et al. |
| 9,179,950 | B2 | 11/2015 | Zajac et al. |
| 9,707,090 | B2 | 7/2017 | DelSignore |
| 11,484,301 | B2 * | 11/2022 | Fleischman ........ A61B 17/0487 |
| 2001/0008971 | A1 | 7/2001 | Schwartz et al. |
| 2002/0019670 | A1 | 2/2002 | Crawley et al. |
| 2002/0123750 | A1 | 9/2002 | Eisermann et al. |
| 2002/0177853 | A1 | 11/2002 | Chervitz et al. |
| 2003/0039676 | A1 | 2/2003 | Boyce et al. |
| 2003/0130694 | A1 | 7/2003 | Bojarski et al. |
| 2003/0139775 | A1 | 7/2003 | Grafton |
| 2003/0233022 | A1 | 12/2003 | Vidlund et al. |
| 2004/0087949 | A1 * | 5/2004 | Bono ................. A61B 17/7041 |
| | | | 606/246 |
| 2004/0127906 | A1 | 7/2004 | Culbert et al. |
| 2005/0019368 | A1 | 1/2005 | Cook et al. |
| 2005/0245932 | A1 | 11/2005 | Fanton et al. |
| 2005/0251209 | A1 | 11/2005 | Saadat et al. |
| 2006/0089711 | A1 | 4/2006 | Dolan |
| 2006/0149261 | A1 | 7/2006 | Nilsson et al. |
| 2006/0195007 | A1 | 8/2006 | Anderson et al. |
| 2006/0241617 | A1 | 10/2006 | Holloway et al. |
| 2006/0282081 | A1 | 12/2006 | Fanton et al. |
| 2006/0282082 | A1 | 12/2006 | Fanton et al. |
| 2006/0282083 | A1 | 12/2006 | Fanton et al. |
| 2007/0156149 | A1 | 7/2007 | Fanton et al. |
| 2007/0156150 | A1 | 7/2007 | Fanton et al. |
| 2007/0156176 | A1 | 7/2007 | Fanton et al. |
| 2007/0255317 | A1 | 11/2007 | Fanton et al. |
| 2007/0260259 | A1 | 11/2007 | Fanton et al. |
| 2008/0132944 | A1 | 6/2008 | Kress |
| 2009/0018655 | A1 | 1/2009 | Brunelle et al. |
| 2009/0171143 | A1 | 7/2009 | Chu et al. |
| 2009/0254190 | A1 | 10/2009 | Gannoe et al. |
| 2009/0306776 | A1 | 12/2009 | Murray |
| 2010/0106254 | A1 | 4/2010 | Delsignore |
| 2011/0208239 | A1 | 8/2011 | Stone et al. |
| 2011/0270306 | A1 | 11/2011 | Denham et al. |
| 2012/0245632 | A1 | 9/2012 | Tsai et al. |
| 2013/0035720 | A1 | 2/2013 | Perriello et al. |
| 2013/0123841 | A1 | 5/2013 | Lyon |
| 2013/0172944 | A1 | 7/2013 | Fritzinger et al. |
| 2013/0190817 | A1 | 7/2013 | Bouduban et al. |
| 2013/0211451 | A1 | 8/2013 | Wales et al. |
| 2014/0052176 | A1 | 2/2014 | Conley et al. |
| 2014/0074161 | A1 * | 3/2014 | Rosenthal .......... A61B 17/0401 |
| | | | 606/232 |
| 2014/0121682 | A1 | 5/2014 | Ferree |
| 2014/0296911 | A1 | 10/2014 | Fanton et al. |
| 2015/0032156 | A1 | 1/2015 | Bennett |
| 2015/0127047 | A1 | 5/2015 | Bruker et al. |
| 2015/0164498 | A1 | 6/2015 | Dreyfuss et al. |
| 2016/0302786 | A1 | 10/2016 | Bennett et al. |

OTHER PUBLICATIONS

Cassidy et al., Basal Joint Arthroplasty and Carpal Tunnel Release Through a Single Incision: An In Vitro Study, J. Hand Surg., vol. 29A, pp. 1085-1088.

Delsignore, Jeanne L. et al., Suture Suspension Arthroplasty Technique for Basal Joint Arthritis Reconstruction, Techniques in Hand and Upper Extremity Surgery, vol. 13, No. 4, 2009, pp. 166-172.

Delsignore, Jeanne, A Modified Technique for Basal Joint Suspensionplasty, Am. Soc. Hand Surgery, Aug. 2004, Issue No. 52.

Glickel et al., Basal Joint Arthroplasty: Indications and Treatment, Current Opinion in Orthopaedics, 2001, vol. 12, pp. 290-294.

Griggs et al., The Use of Suture Anchors in the Hand and Wrist, in Current Practice in Hand Surgery, 1997, pp. 73-77, Mosby.

Heyworth, Benton E., Tendon transfer arthroplasty vs. LRTI arthroplasty for surgical treatment of basal joint arthritis of the thumb: A randondized, double-blinded clinical trial, Doris Duke Medical Students' Journal, vol. 2, 2002-2003, pp. 46-52.

Matullo, Kristofer S. et al., CMC Arthroplasty of the Thumb: A Review, Am. Assn. Hand Surgery, vol. 2, 2007, pp. 232-239.

PCT Search Report for PCT Application No. PCT/US2009/060263; mailed Dec. 1, 2009; 2 pages.

Shaieb, M. D. et al., Tensile Strengths of Various Suture Techniques, J. Hand Surgery (British and European Volume), vol. 22, No. 6, 1997, pp. 764-767.

Shuler, Michael S. et al., Basal Joint Arthritis of the Thumb, J. Am. Acad. Orthop. Surg., vol. 16, No. 7, 2008, pp. 418-423.

Tornier, Piton product brochure, 2016.

Trumble, Thomas et al., Thumb Carpometacarpal Arthroplasty with Ligament Reconstruction and Interposition Costochondral Arthroplasty, Journal of Wrist Surgery, vol. 2, No. 3, 2013, pp. 220-227.

Weidrich, The Use of Suture Anchors in the Hand and Wrist, Operative Tech. in Plastic and Recon. Surg., 1997, vol. 4, pp. 42-48.

* cited by examiner

SPACE CREATED
BY EXCISION OF
THE TRAPEZIUM

95

100     100

100     100

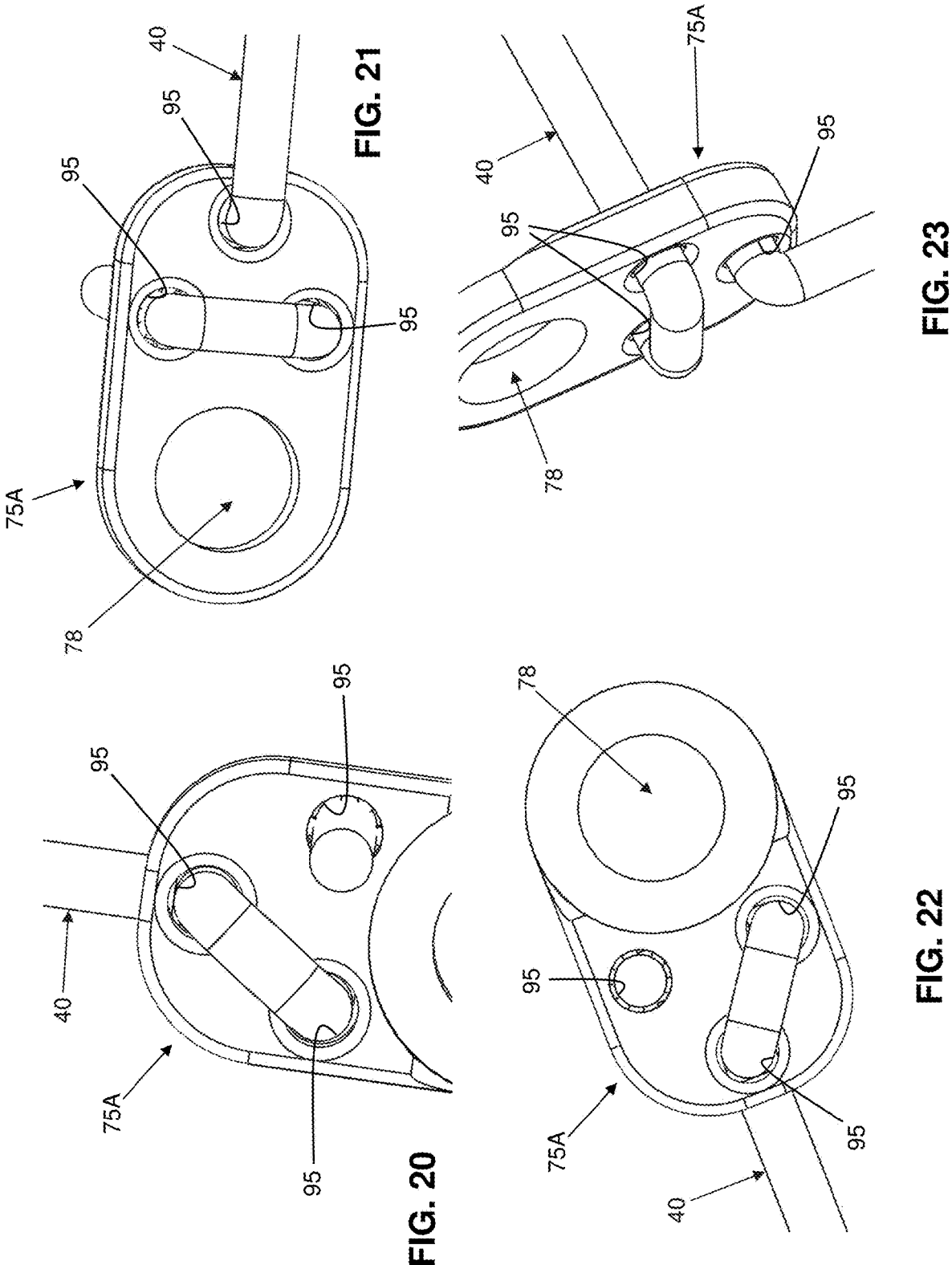

SECTION B-B
SCALE 8:1

SUTURE-LOCKING WASHER FOR USE WITH A BONE ANCHOR, AND METHOD FOR SUPPORTING THE THUMB OF A PATIENT AFTER BASAL JOINT ARTHROPLASTY, AND OTHER NOVEL ORTHOPEDIC APPARATUS AND OTHER NOVEL ORTHOPEDIC PROCEDURES

REFERENCE TO PENDING PRIOR PATENT APPLICATIONS

This patent application is a continuation of pending prior U.S. patent application Ser. No. 15/999,085, filed Aug. 16, 2018 by CMC Group LLC and Sidney Fleischman et al. for SUTURE-LOCKING WASHER FOR USE WITH A BONE ANCHOR, AND METHOD FOR SUPPORTING THE THUMB OF A PATIENT AFTER BASAL JOINT ARTHROPLASTY, AND OTHER NOVEL ORTHOPEDIC APPARATUS AND OTHER NOVEL ORTHOPEDIC PRO-CEDURES, which patent application in turn:

(1) is a continuation-in-part of prior U.S. patent application Ser. No. 14/596,973, filed Jan. 14, 2015 by CMC Group LLC and Izi Bruker et al. for SLING SUSPEN-SION SYSTEM FOR SUPPORTING THE THUMB OF A PATIENT AFTER BASAL JOINT ARTHRO-PLASTY, which patent application:

(a) claims benefit of prior U.S. Provisional Patent Application Ser. No. 61/927,309, filed Jan. 14, 2014 by CMC Group LLC and Izi Bruker et al. for BASAL THUMB ARTHRITIS SLING SYSTEM; and (2) claims benefit of prior U.S. Provisional Patent Application Ser. No. 62/546,187, filed Aug. 16, 2017 by CMC Group LLC and Sidney Fleischman et al. for SUTURE-LOCKING WASHER FOR USE WITH A BONE ANCHOR, AND METHOD FOR SUPPORT-ING THE THUMB OF A PATIENT AFTER BASAL JOINT ARTHROPLASTY.

The four (4) above-identified patent applications are hereby incorporated herein by reference.

FIELD OF THE INVENTION

This invention relates to novel orthopedic medical devices for locking an elongated element (e.g., a suture) to a bone anchor in order to reposition bone, soft tissue, or other anatomy, and to a novel sling suspension system for supporting the thumb of a patient after basal joint arthroplasty.

The novel orthopedic medical devices of the present invention may, alternatively, relate to tenodesis applications, or other soft tissue-to-bone attachment applications, in which conventional screw anchors (or other types of anchors), or other implantable medical devices, are aug-mented with novel suture attachment mechanisms that obvi-ate the need to tie knots in the suture when attaching the suture to a bone anchor (or to another implantable medical device) or to tissue.

BACKGROUND OF THE INVENTION

Degenerative osteoarthritis of the first metacarpal joint of the thumb (sometimes referred to as "the basal joint") is a common debilitating condition, especially in middle-aged women. Research shows that 25% of all women and 8% of all men in their fifties complain of pain in the base of the thumb, secondary to basal joint osteoarthritis. Basal joint arthritis can cause substantial pain, digit weakness and loss of functionality.

In severe cases of basal joint arthritis, basal joint recon-struction may be required. In general, basal joint reconstruc-tion involves trapezial excision (sometimes referred to as "basal joint arthroplasty"), which is required for pain relief, and subsequent soft tissue reconstruction in order to restore proper balance, alignment, longitudinal length and function to the thumb.

Unfortunately, such soft tissue reconstruction has tradi-tionally involved harvesting tendons which are subsequently transferred and re-directed via drill holes in the thumb metacarpal in order to restore proper balance, alignment, longitudinal length and function to the thumb. However, this means harvesting, and thereby sacrificing, all or some of one or more existing, functioning tendons. In addition, such soft tissue reconstruction typically requires temporary pinning of the anatomy, which can give rise to pin tract complications such as infection, nerve damage and neuroma formation.

As a result, a new approach is needed for effecting basal joint reconstruction after performing basal joint arthroplasty in order to alleviate basal joint arthritis.

In addition to the foregoing, in many situations, anatomi-cal objects (e.g., bone, soft tissue, prostheses, etc.) need to be attached to one another. And in many situations, it may be desirable to effect this attachment with suture. However, it can sometimes be problematic to tie knots in the suture so as to fix the anatomical objects relative to one another. In addition, it can sometimes be problematic to form through-holes in bone to secure the suture to the bone. Therefore, a new approach is needed for making knotless fixations of anatomical objects without having to drill through-holes in bone.

SUMMARY OF THE INVENTION

The present invention comprises the provision and use of novel suture-securing mechanisms that enable the tightening and locking (e.g., cinching) of suture to an anchor or other implantable medical device without the need to tie knots in the suture in order to adjustably secure the suture to the anchor or other implantable medical device.

In one preferred form of the invention, there is provided suture-locking washers which are mounted to bone anchors, wherein the suture-locking washers comprise suture-secur-ing mechanisms.

The present invention also comprises the provision and use of bone anchors and novel suture-locking washers for use as part of a novel sling suspension system which may be used to effect basal joint reconstruction after performing basal joint arthroplasty in order to alleviate basal joint arthritis.

More particularly, in one preferred form of the invention, the invention comprises suture-locking washers comprising suture-securing mechanisms, wherein the suture-locking washers are utilized in combination with bone anchors to form a novel sling suspension system which can be used to join the thumb metacarpal to the index metacarpal, whereby to enable tightening and locking (e.g., cinching) of a sling (e.g., a suture) of the sling suspension system so as to support the thumb of a patient after basal joint arthroplasty. The present invention eliminates the specific complications and increased morbidity associated with tendon harvesting and transfer procedures, and also eliminates the complica-tions and increased morbidity associated with those proce-dures that require temporary pin fixation or drill holes for tendon or suture passage. The novel sling suspension system of the present invention provides secure and stable support for the thumb of a patient after performing basal joint arthroplasty so as to alleviate basal joint arthritis, and is fast and simple to use, since the suture-securing mechanism of the suture-locking washer eliminates the need to tie knots in the suture in order to secure the suture to a bone anchor.

In one preferred form of the invention, there is provided a sling suspension system for supporting the thumb of a patient after basal joint arthroplasty, the sling suspension system comprising:

an index metacarpal anchor;

a thumb metacarpal anchor; and a sling (e.g., a suture) for securing the thumb metacarpal anchor to the index metacarpal anchor;

the index metacarpal anchor comprising at least one bone-engaging element for securing the index metacarpal anchor to bone and a sling-engaging element for capturing the sling to the index metacarpal anchor;

the thumb metacarpal anchor comprising at least one bone-engaging element for securing the thumb metacarpal anchor to bone and a sling-engaging element for capturing the sling to the thumb metacarpal anchor;

the sling comprising an elongated body having a first anchor-engaging element for securing the sling to the sling-engaging element of the index metacarpal anchor, and a second anchor-engaging element for securing the sling to the sling-engaging element of the thumb metacarpal anchor;

wherein the at least one sling-engaging element of the thumb metacarpal anchor comprises at least one suture-locking washer for adjustably securing the sling to the thumb metacarpal anchor.

In another preferred form of the invention, there is provided a method for supporting the thumb of a patient after basal joint arthroplasty, the method comprising:

securing a first end of a sling to an index metacarpal anchor;

positioning the index metacarpal anchor in the index metacarpal;

adjustably securing the second end of the sling to a thumb metacarpal anchor;

inserting the thumb metacarpal anchor into the thumb metacarpal; and tightening the sling (e.g., a suture) in one direction through an adjustable suture-securing mechanism of the thumb metacarpal anchor so as to fixedly connect the thumb metacarpal to the index metacarpal.

In one preferred form of the invention, the suture-securing mechanism of the thumb metacarpal anchor is provided via a suture-locking washer which is secured to the thumb metacarpal anchor.

In another preferred form of the invention, there is provided a method for alleviating basal joint arthritis, the method comprising:

excising the trapezium of a patient;

securing a first end of a sling (e.g., a suture) to an index metacarpal anchor;

positioning the index metacarpal anchor in the index metacarpal;

adjustably securing the second end of the sling to a thumb metacarpal anchor;

inserting the thumb metacarpal anchor into the thumb metacarpal; and tightening the sling by pulling a free end of the sling relative to a suture-securing mechanism of the thumb metacarpal anchor so that the second end of the sling is fixedly secured to the thumb metacarpal anchor, whereby the sling fixedly connects the thumb metacarpal to the index metacarpal.

In one preferred form of the invention, the suture-securing mechanism of the thumb metacarpal anchor is provided via a suture-locking washer which is secured to the thumb metacarpal anchor.

In another preferred form of the invention, the suture-locking washer (which carries the suture-securing mechanism) is formed integral with the thumb metacarpal anchor.

In another preferred form of the invention, the suture-locking washer (which carries the suture-securing mechanism) is mounted to a bone anchor (which may be used as the thumb metacarpal anchor, or as the index metacarpal anchor, or as an anchor for other locations within the body) or to another implantable medical device.

And in another preferred form of the invention, the suture-securing mechanism may be incorporated directly into a bone anchor (which may be used as the thumb metacarpal anchor, or as the index metacarpal anchor, or as an anchor for other locations within the body) or into another implantable medical device.

And in another form of the invention, a novel method and apparatus is provided for effecting knotless fixations of anatomical objects.

In another form of the invention, there is provided a sling suspension system for supporting the thumb of a patient after basal joint arthroplasty, the sling suspension system comprising:

an index metacarpal anchor;

a thumb metacarpal anchor; and a sling for securing said thumb metacarpal anchor to said index metacarpal anchor;

said index metacarpal anchor comprising at least one bone-engaging element for securing said index metacarpal anchor to an index metacarpal, and a sling-engaging element for attaching said sling to said index metacarpal anchor;

said thumb metacarpal anchor comprising at least one bone-engaging element for securing said thumb metacarpal anchor to a thumb metacarpal, and a sling-engaging element for attaching said sling to said thumb metacarpal anchor;

wherein at least one of said sling-engaging element of said thumb metacarpal anchor and said sling-engaging element of said index metacarpal anchor comprises a sling-securing mechanism which is configured to provide one-way movement of said sling relative to said sling-securing mechanism.

In another form of the invention, there is provided a method for supporting the thumb of a patient after basal joint arthroplasty, said method comprising:

providing a sling suspension system, said sling suspension system comprising:

an index metacarpal anchor;

a thumb metacarpal anchor; and a sling for securing said thumb metacarpal anchor to said index metacarpal anchor;

said index metacarpal anchor comprising at least one bone-engaging element for securing said index metacarpal anchor to an index metacarpal, and a sling-engaging element for attaching said sling to said index metacarpal anchor;

said thumb metacarpal anchor comprising at least one bone-engaging element for securing said thumb metacarpal anchor to a thumb metacarpal, and a sling-engaging element for attaching said sling to said thumb metacarpal anchor;

wherein at least one of said sling-engaging element of said thumb metacarpal anchor and said sling-engaging element of said index metacarpal anchor comprises a sling-securing mechanism which is configured to provide one-way movement of said sling relative to said sling-securing mechanism;

attaching said sling to said sling-engaging element of said index metacarpal anchor and attaching said sling to said sling-engaging element of said thumb metacarpal anchor;

positioning said index metacarpal anchor in an index metacarpal;

inserting said thumb metacarpal anchor into a thumb metacarpal; and moving said sling through said sling-securing mechanism so as to shorten the length of said sling extending between said index metacarpal anchor and said thumb metacarpal anchor so as to fixedly connect the thumb metacarpal to the index metacarpal.

In another form of the invention, there is provided apparatus for securing a first anatomical object to a second anatomical object, said apparatus comprising:

a body having an opening; and a tubular structure disposed in said opening, said tubular structure comprising a side wall defining a passageway, a portion of said side wall of said tubular structure projecting into said passageway so as to provide one-way movement of a filament through said passageway.

In another form of the invention, there is provided a method for securing a first anatomical object to a second anatomical object, said method comprising:

providing apparatus for securing the first anatomical object to the second anatomical object, said apparatus comprising:

a body having an opening; and a tubular structure disposed in said opening, said tubular structure comprising a side wall defining a passageway, a portion of said side wall of said tubular structure projecting into said passageway so as to provide one-way movement of a filament through said passageway;

passing a filament through said passageway;

associating one end of said filament with the second anatomical object and associating said body with the first anatomical object; and moving said filament through said passageway so as to shorten the length of said filament extending between the first anatomical object and the second anatomical object so as to fixedly connect the first anatomical object to the second anatomical object.

BRIEF DESCRIPTION OF DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 17-23 are schematic views of another novel suture-locking washer formed in accordance with the present invention;

DETAILED DESCRIPTION OF THE PREFERRED EMBODIMENTS

The Human Hand

Figure 1:
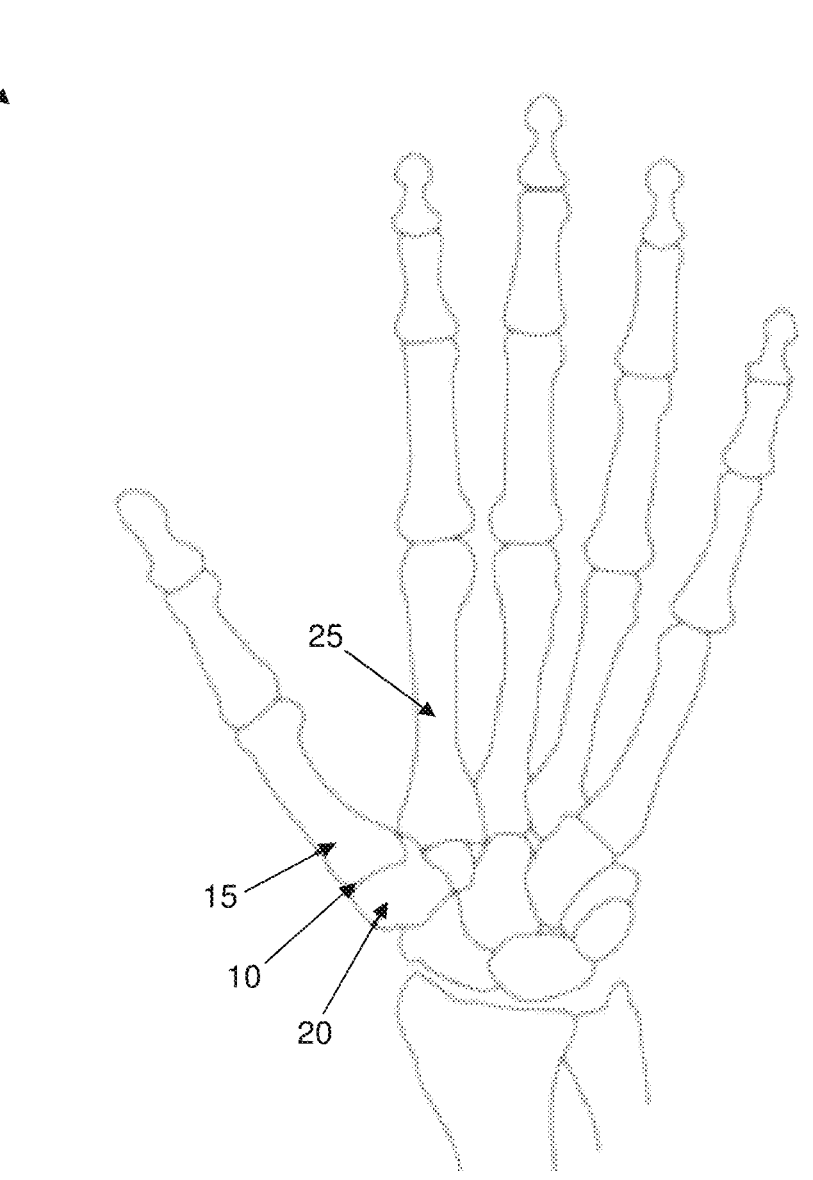
FIG. 1 is a schematic view showing the bone structure of the right hand of a human.

Looking first at FIG. 1, there is shown the right hand 5 of a human. As seen in the figure, the basal joint 10 is formed at the junction of the thumb metacarpal 15 and the trapezium 20. Note also the location of the adjacent index metacarpal 25.

As noted above, many people suffer from significant basal joint arthritis and would benefit from basal joint reconstruction in order to alleviate the basal joint arthritis.

Basal Joint Reconstruction

The present invention provides a new approach for effecting basal joint reconstruction after performing basal joint arthroplasty in order to alleviate basal joint arthritis.

Figure 2:
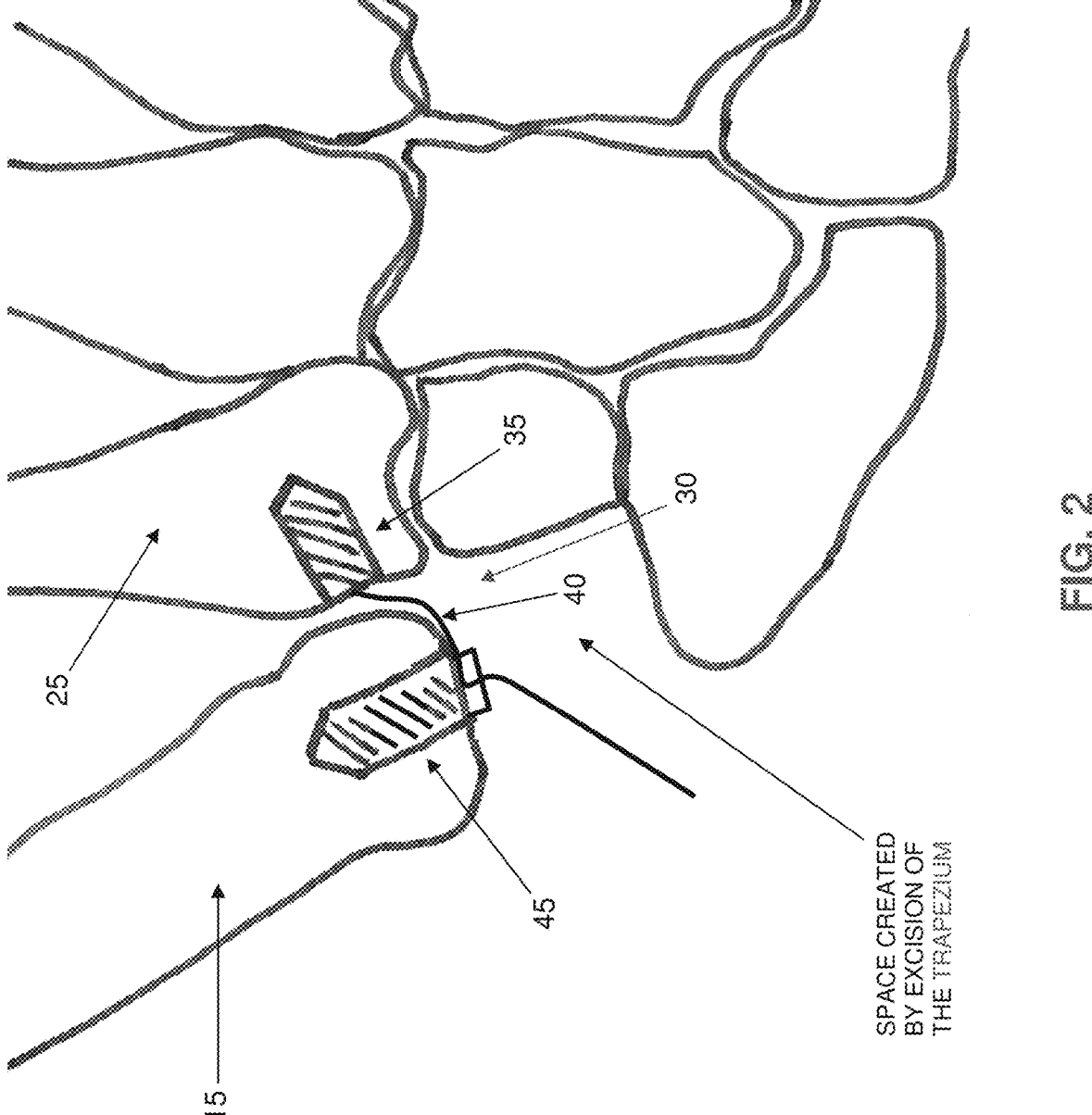
FIG. 2 is a schematic view showing a basal joint reconstruction using the novel sling suspension system of the present invention.

More particularly, and looking now at FIG. 2, the present invention comprises the provision and use of a novel sling suspension system 30 that joins the thumb metacarpal to the index metacarpal so as to support the thumb of a patient after basal joint arthroplasty.

As will hereinafter be discussed in further detail, and still looking at FIG. 2, novel sling suspension system 30 generally comprises an index metacarpal anchor 35 having a sling (e.g., a suture) 40 fixedly secured thereto, and a thumb metacarpal anchor 45 having sling (e.g., a suture) 40 adjustably secured thereto.

And as will hereinafter be discussed, novel sling suspension system 30 may be used in a procedure to alleviate basal joint arthritis, wherein:

the trapezium of a patient is excised;

the index metacarpal anchor is positioned in the index metacarpal;

the thumb metacarpal anchor is positioned in the thumb metacarpal; and the sling is tightened by pulling a free end of the sling relative to a suture-securing mechanism of the thumb metacarpal anchor so that the sling is fixedly secured to the thumb metacarpal anchor, whereby the sling fixedly connects the thumb metacarpal to the index metacarpal.

The novel sling suspension system of the present invention provides secure and stable support for the thumb of a patient after performing basal joint arthroplasty in order to alleviate basal joint arthritis, and is relatively fast and simple to implement.

More particularly, the present invention comprises the provision and use of a suture-securing mechanism which may be used in concert with one or more bone anchors for effecting basal joint reconstruction after performing basal joint arthroplasty to alleviate basal joint arthritis.

In one form of the present invention, the invention comprises the provision and use of a novel sling suspension system comprising a knotless sling attachment that can be used to join the thumb metacarpal to the index metacarpal in order to support the thumb of a patient after basal joint arthroplasty. The present invention eliminates the specific complications and increased morbidity associated with tendon harvesting and transfer procedures, as well as the specific complications and increased morbidity associated with those procedures that require temporary pin fixation or drill holes for tendon or suture passage.

In one preferred form of the invention, the novel sling suspension system comprises at least one suture-locking washer for use with a bone anchor, wherein the at least one suture-locking washer comprises at least one suture-securing mechanism to enable tightening and securing (e.g., cinching) of a suture (i.e., the "sling") once appropriate anchors (e.g., an index finger screw anchor, a thumb screw anchor, etc.) are positioned in the anatomy so as to provide stable support for the thumb of a patient after performing basal joint arthroplasty, whereby to alleviate basal joint arthritis. The novel sling suspension system of the present invention is relatively fast and simple to implement.

The Novel Sling Suspension System Utilizing Novel Suture-Locking Washers

As noted above, many people suffer from significant basal joint arthritis and would benefit from basal joint reconstruction to alleviate the basal joint arthritis.

Figure 3:
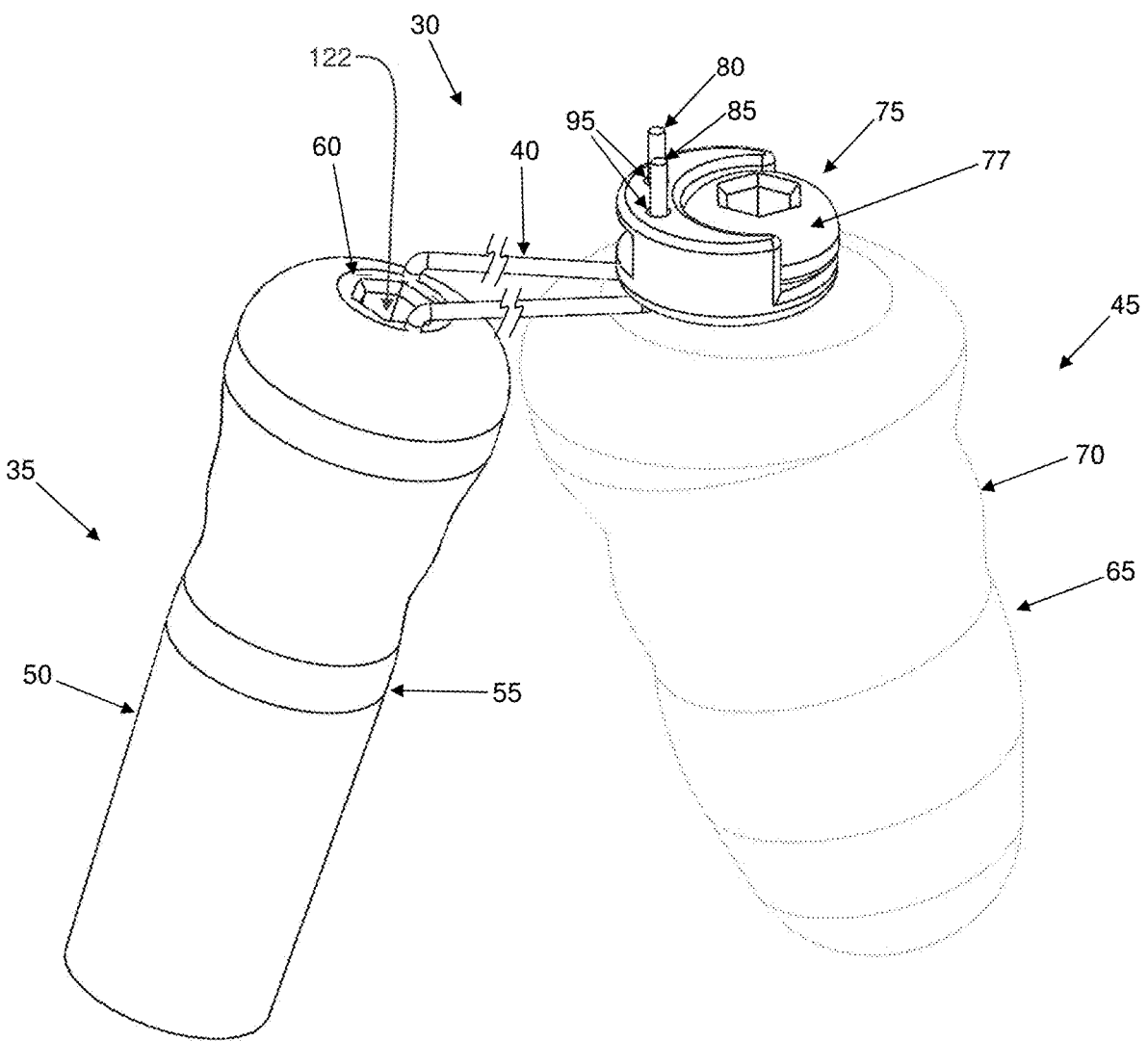
FIG. 3 is a schematic view showing a novel sling suspension system formed in accordance with the present invention, wherein the novel sling suspension system comprises an index metacarpal anchor with a suture secured thereto, and a thumb metacarpal anchor with a suture adjustably secured thereto, wherein the suture is adjustably secured to the thumb metacarpal anchor via a suture-locking washer.
Figure 4:
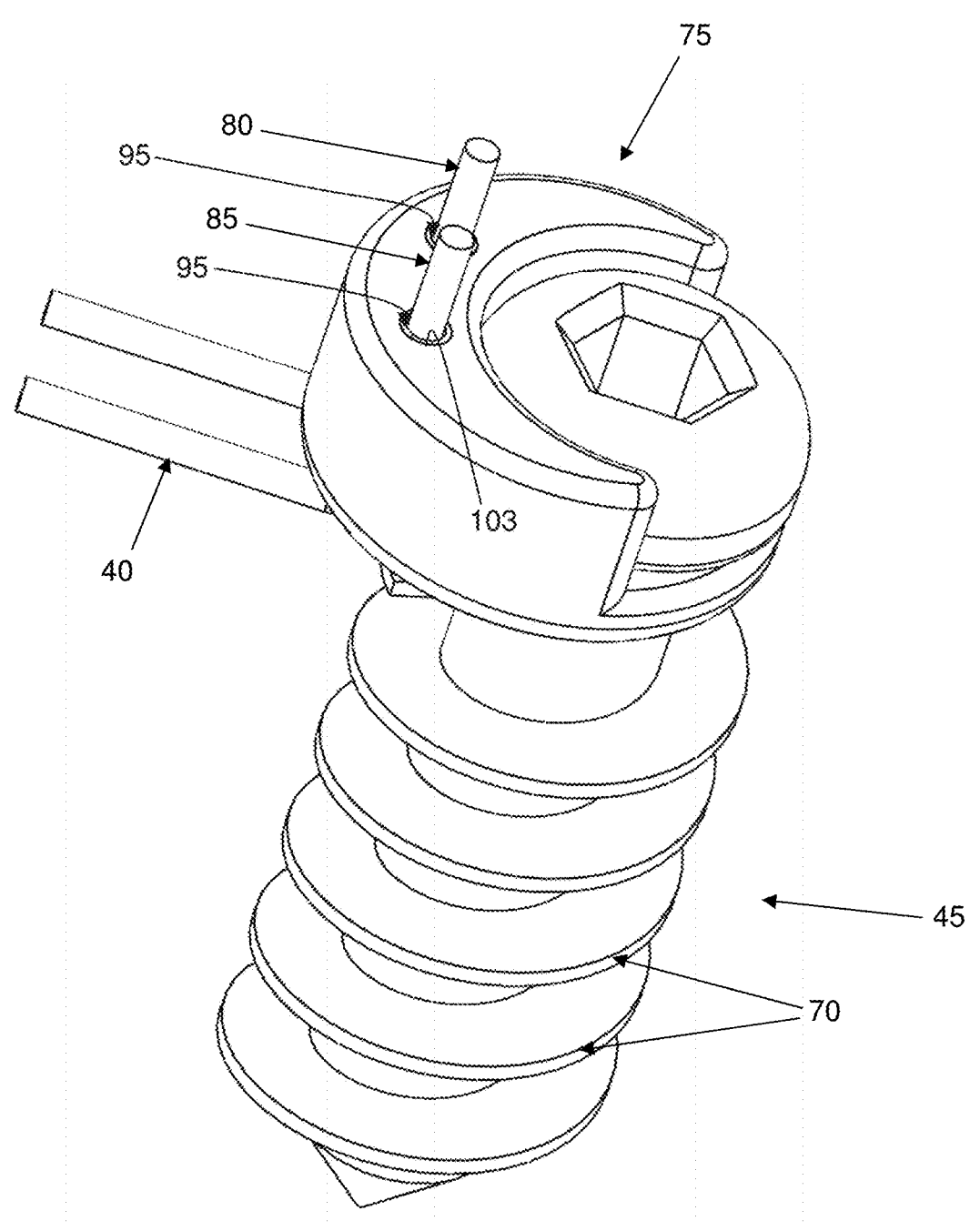
FIGS. 4-11 are various views of selected portions of the novel sling suspension system shown in FIG. 3.

FIG. 3 shows a novel sling suspension system 30 for disposition in and between an index finger and a thumb of a human hand.

Sling suspension system 30 generally comprises index metacarpal anchor 35 for deployment in index metacarpal 25, thumb metacarpal anchor 45 for deployment in thumb metacarpal 15, and sling 40 (e.g., a suture) for securing thumb metacarpal anchor 45 to index metacarpal anchor 35, whereby to support the thumb of a patient after basal joint arthroplasty has been performed in order to alleviate basal joint arthritis. See FIG. 3. Although sling 40 will hereinafter generally be discussed in the context of a suture "sling", it should be appreciated that sling 40 may comprise substantially any elongated flexible element, and is not intended to be limited to suture. In addition, it should also be appreciated that sling 40 may comprise structure in addition to an elongated flexible element (e.g., a suture). By way of example but not limitation, sling 40 may comprise a hammock-like structure mounted to one or more elongated flexible elements (e.g., sutures), such that the one or more elongated flexible elements (e.g., sutures) may be mounted to index metacarpal anchor 35 and thumb metacarpal anchor 45, and the hammock-like structure may engage and support portions of thumb metacarpal 15.

Index metacarpal anchor 35 is intended to be deployed in (e.g., screwed into or pushed into) a drill hole (i.e., a bone hole) formed at or near the base of index metacarpal 25. See FIG. 2. Alternatively, index metacarpal anchor 35 may comprise a self-tapping anchor, in which case the bone hole is formed during delivery of the bone anchor into the index metacarpal. Index metacarpal anchor 35 comprises a body 50 having at least one bone-engaging element 55 (e.g., screw threads, ribs, etc.) (see FIG. 3) formed thereon for engaging the side wall of the bone hole, i.e., for engaging index metacarpal 25. In this way, index metacarpal anchor 35 can be secured to index metacarpal 25. Index metacarpal anchor 35 further comprises a sling-engaging element 60 (e.g., a recessed eyelet) (see FIG. 3) for capturing sling 40 to index metacarpal anchor 35.

Figures 5, 6, 7, 8:
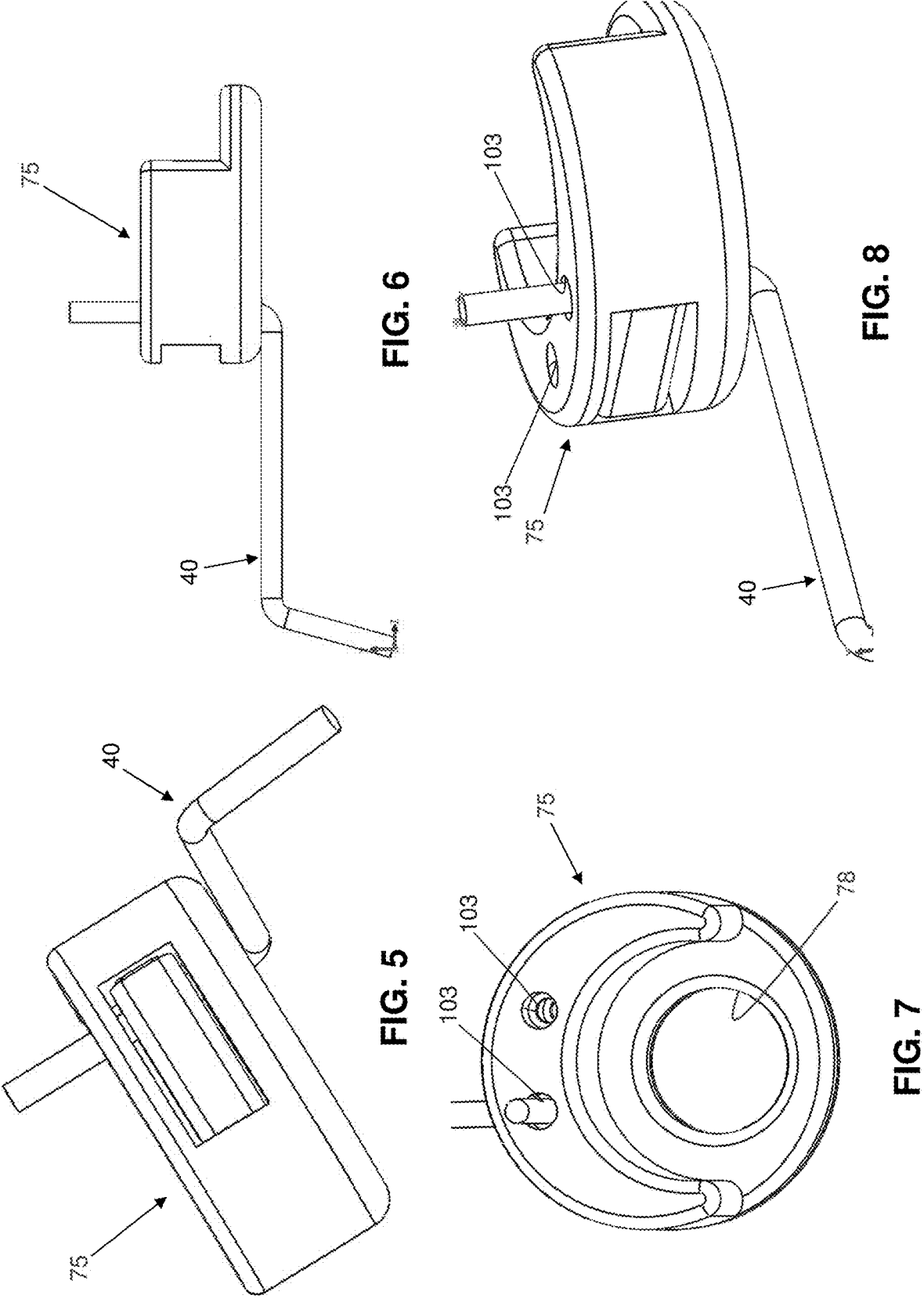

Thumb metacarpal anchor 45 is intended to be deployed in (e.g., screwed into or pushed into) a drill hole (i.e., a bone hole) formed at or near the base of thumb metacarpal 15. See FIG. 2. Alternatively, thumb metacarpal anchor 45 may comprise a self-tapping anchor, in which case the bone hole is formed during delivery of the bone anchor into the thumb metacarpal. Thumb metacarpal anchor 45 comprises a body 65 having at least one bone-engaging element 70 (e.g., screw threads, ribs, etc.) (see FIG. 3) formed thereon for engaging the side wall of the bone hole, i.e., for engaging thumb metacarpal 15. In this way, thumb metacarpal anchor 45 can be secured to thumb metacarpal 15. Thumb metacarpal anchor 45 further comprises a suture-locking washer 75 (i.e., a sling-engaging element) for mounting to thumb metacarpal anchor 45 and for adjustably gripping and securing sling 40 to thumb metacarpal anchor 45 as will hereinafter be discussed in further detail. In one preferred form of the invention, suture-locking washer 75 comprises a body having a hole formed therein (see FIG. 7) for mounting the suture-locking washer to thumb metacarpal anchor 45. In one preferred form of the invention, suture-locking washer 75 is rotatably secured to thumb metacarpal anchor 45 so that suture-locking washer 75 is able to traverse (i.e., rotate) 360 degrees around the longitudinal axis of body 65 of thumb metacarpal anchor 45. By way of example but not limitation, suture-locking washer 75 is rotatably mounted to thumb metacarpal anchor 45 with a screw 77 (see FIG. 3) which passes through a hole 78 (see FIG. 7) formed in suture-locking washer 75 and into thumb metacarpal anchor 45.

Sling 40 secures thumb metacarpal anchor 45 to index metacarpal anchor 35, whereby to provide, in combination with thumb metacarpal anchor 45 and index metacarpal anchor 35, a sling suspension system for supporting the thumb of a patient after basal joint arthroplasty has been performed to alleviate basal joint arthritis. To this end, in one preferred form of the invention, sling 40 comprises an elongated flexible body (e.g., a suture) having a first end 80 and a second end 85. See FIG. 3. And in one preferred form of the invention, sling 40 includes an anchor-engaging element (not shown), e.g., a knot or looped section of the sling, for securing sling 40 to index metacarpal anchor 35 such that the sling is attached to index metacarpal anchor 35. Thus, in one preferred form of the invention, sling 40 comprises first end 80 and second end 85 which engage suture-locking washer 75 (which is itself mounted to thumb metacarpal anchor 45), and an intermediate portion of the elongated flexible body (e.g., the suture) which engages index metacarpal anchor 35. See FIG. 3.

Figure 9:
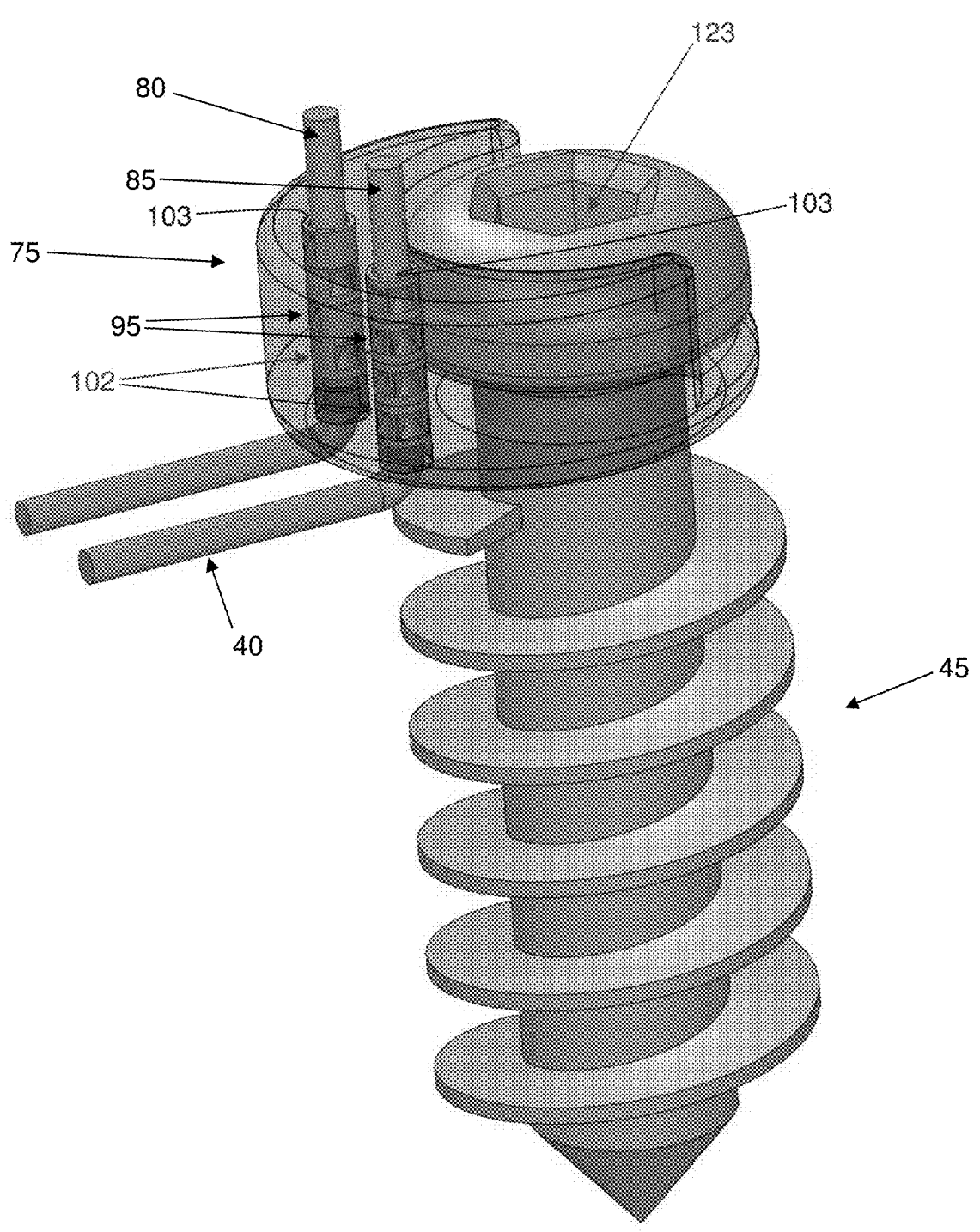
Figure 10:
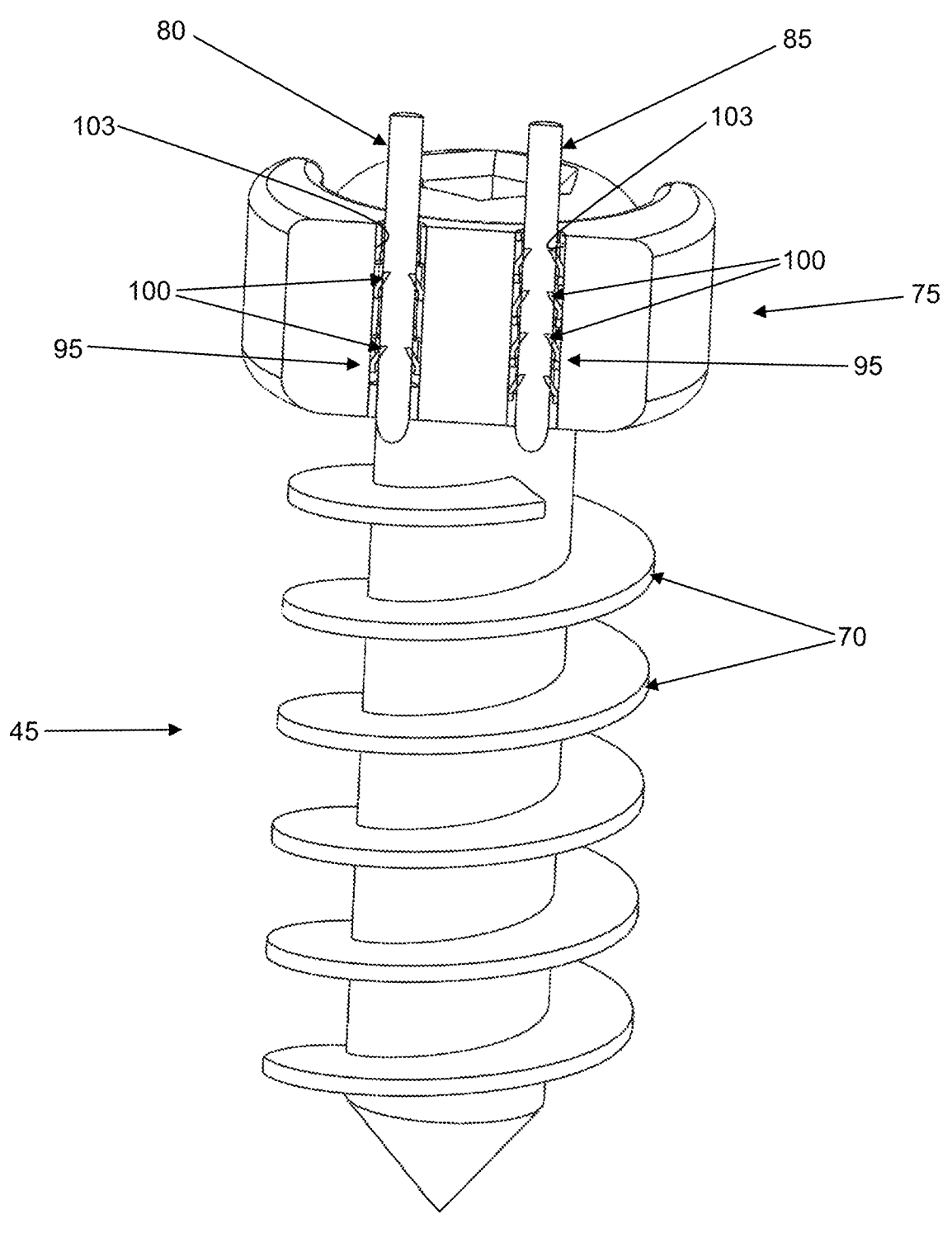
Figure 11:
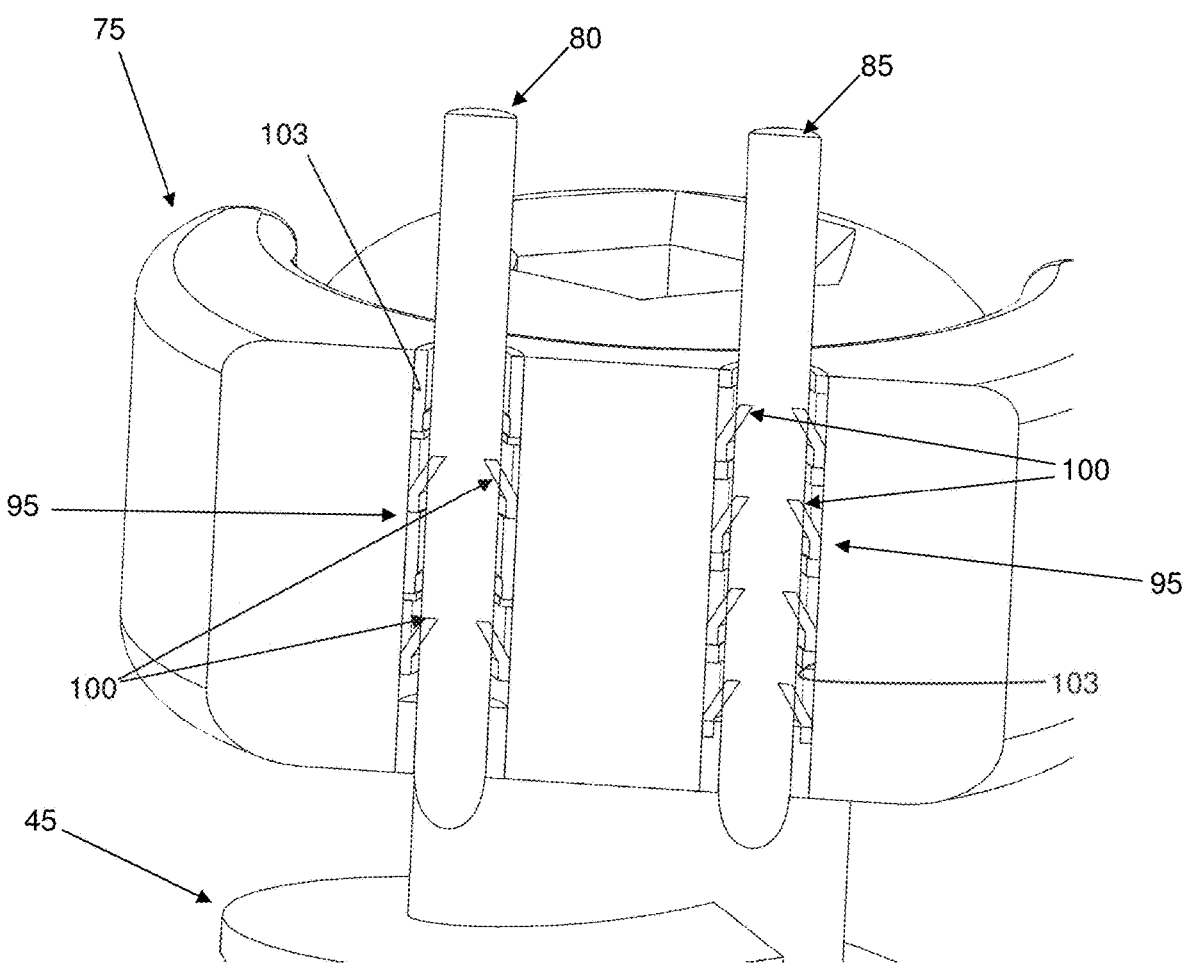

Suture-locking washer 75 comprises one or more adjustable suture-securing mechanisms 95 (see FIGS. 9-11) for securing sling 40 to suture-locking washer 75 of thumb metacarpal anchor 45 such that the sling is adjustably attached to thumb metacarpal anchor 45, as will hereinafter be discussed.

The elongated body of sling 40 may comprise a flexible filament (e.g., a suture, a rope, a web, a tape, etc.), or some other flexible elongated structure, i.e., substantially any flexible elongated structure which will suffice for the intended purpose, either man-made (e.g., biocompatible polymers, metals, etc.) or biologic (e.g., cross-linked collagen, cross-linked hydrogel, chitosan, etc.), and/or composite structures. In one preferred form of the invention, sling 40 comprises a suture. Where sling 40 comprises a suture, it should be appreciated that the suture can be a hollow or solid core braided suture, a monofilament suture, etc. It should also be appreciated that, if desired, sling 40 may be constructed and configured so that it is able to slide with respect to itself, e.g., such as where it has been passed through itself.

As shown in FIGS. 2 and 3 and discussed above, sling suspension system 30 comprises index metacarpal anchor 35 and thumb metacarpal anchor 45, both of which are fixedly secured to bone. In one preferred form of the invention, index metacarpal anchor 35 and thumb metacarpal anchor 45 both comprise screw anchors that engage the bone of a metacarpal and remain affixed to a metacarpal as the associated sling 40 (which is coupled to index metacarpal anchor 35 and thumb metacarpal anchor 45) is tightened and secured (i.e., cinched) to thumb metacarpal anchor 45. It should be appreciated that bone anchors having alternative bone-engaging mechanisms (e.g., ribs as opposed to screw threads, or expanding bodies, etc.) may alternatively (or additionally) be utilized, as will be apparent to those skilled in the art in view of the present disclosure.

As shown in FIGS. 2-9, sling 40 preferably comprises two suture strands (preferably high-strength, high-density polyethylene suture or the equivalent) which are looped or tied (or otherwise secured) to the base (i.e., the proximal end) of index metacarpal anchor 35. Alternatively, if desired, sling 40 may comprise a single strand of suture which is looped through (or otherwise secured to) the base (i.e., the proximal end) of index metacarpal anchor 35, e.g., such as by looping the suture through sling-engaging element 60 (e.g., a recessed eyelet). The free ends 80, 85 of sling 40 are threaded through suture-securing mechanism 95 of suture-locking washer 75. Suture-locking washer 75 is mounted to thumb metacarpal anchor 45 which, in one preferred form of the invention, comprises a screw anchor. It should be appreciated that, if desired, suture-locking washer 75 may, alternatively and/or additionally, be coupled to index metacarpal anchor 35. However, due to the clinical ease of pulling the sling relative to the thumb metacarpal anchor 45, in the preferred form of the present invention, suture-locking washer 75 is secured to thumb metacarpal anchor 45 as shown in FIG. 3.

The Suture-Securing Mechanism

Suture-locking washer 75 is mounted to the base (i.e., the proximal end) of thumb metacarpal anchor 45, and comprises the aforementioned at least one suture-securing mechanism 95. See FIGS. 9-11. Suture-securing mechanism 95 is shown in greater detail in FIGS. 9-12. In one preferred form of the invention, two suture-securing mechanisms 95 are utilized, each of which allows the passage and attachment of a free end 80, 85 of sling 40 to suture-locking washer 75, as will hereinafter be discussed in further detail. Once index metacarpal anchor 35 is secured to the index metacarpal, and thumb metacarpal anchor 45 is positioned in the thumb metacarpal, the free end(s) 80, 85 of sling 40 are retracted (i.e., pulled, or "cinched") as the thumb is positioned relative to the index finger. Suture-securing mechanisms 95 (shown in flattened form in FIG. 12) engage the first and second ends 80, 85 of sling 40 with suture-holding elements 100 (e.g., barbs) in order to allow one-way passage of first and second ends 80, 85 of sling 40 through suture-securing mechanisms 95, whereby to enable one-way tightening (i.e., cinching) of sling 40 upon positioning of the thumb metacarpal 15 relative to index metacarpal 25. As this occurs, suture-securing mechanisms 95 prevent sling 40 from sliding in the opposite direction of tightening, thereby preventing slipping of sling 40 and affixedly attaching sling 40 (and thus thumb metacarpal 15 and index metacarpal 25) into stable position during healing of the newly reconstructed basal joint.

The suture-securing mechanisms 95 shown in FIGS. 9-12 generally comprise tubular structures 102 (FIG. 9) which are laser-cut into (or otherwise formed into) a pattern including suture-holding elements (barbs or teeth) 100 (FIG. 10) which are bent or positioned inwardly when the tube is assembled so as to form the suture-securing mechanism 95, whereby to engage sling 40.

Figure 12:
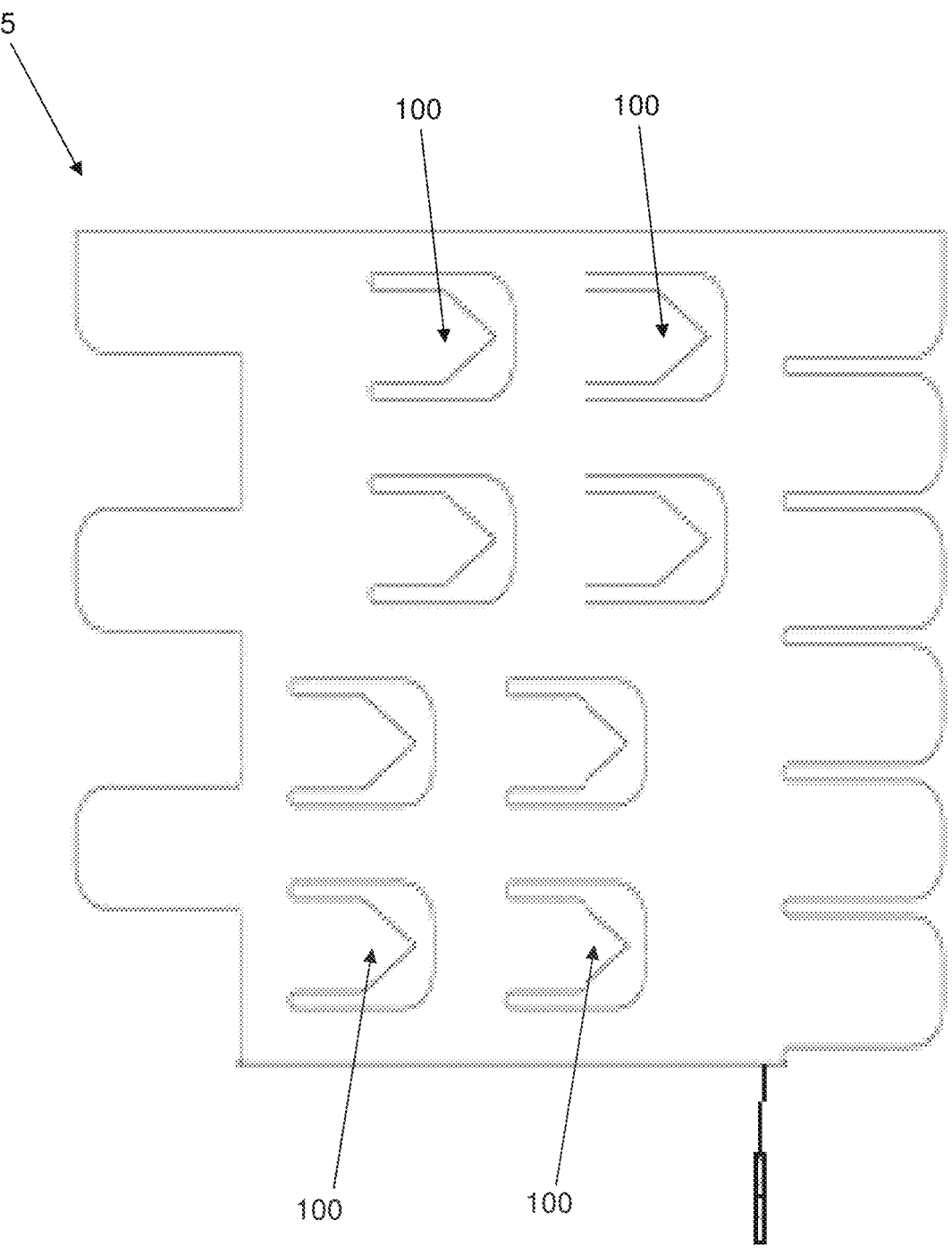
FIG. 12 is a flattened view of selected portions of the suture-securing mechanism of the suture-locking washer shown in FIGS. 4-11.
Figure 13:
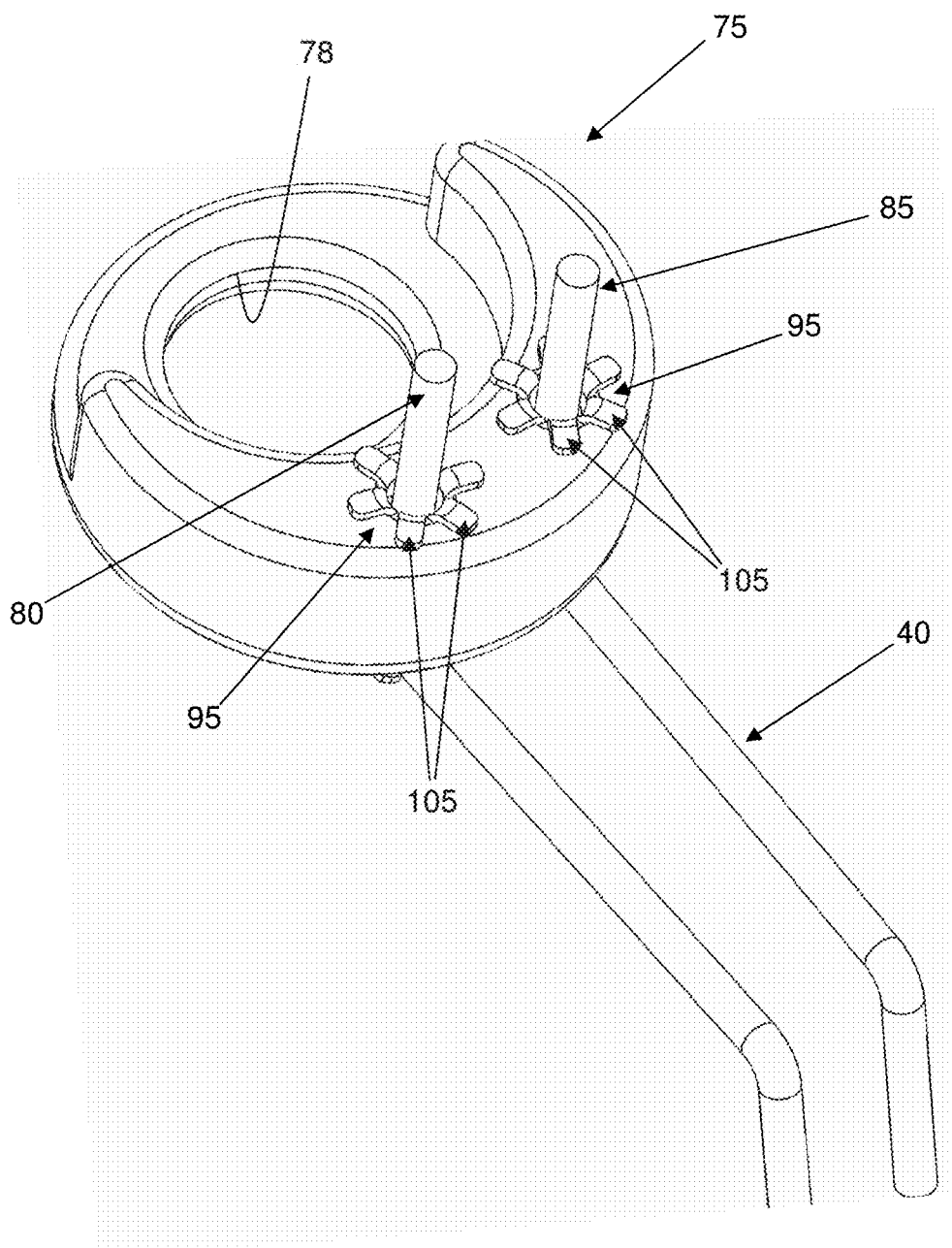
FIGS. 13-15 are schematic views showing another novel suture-securing mechanism formed in accordance with the present invention, wherein the suture-securing mechanism comprises a plurality of protrusions which facilitate mounting the suture-securing mechanism to a suture-locking washer.
Figure 14:
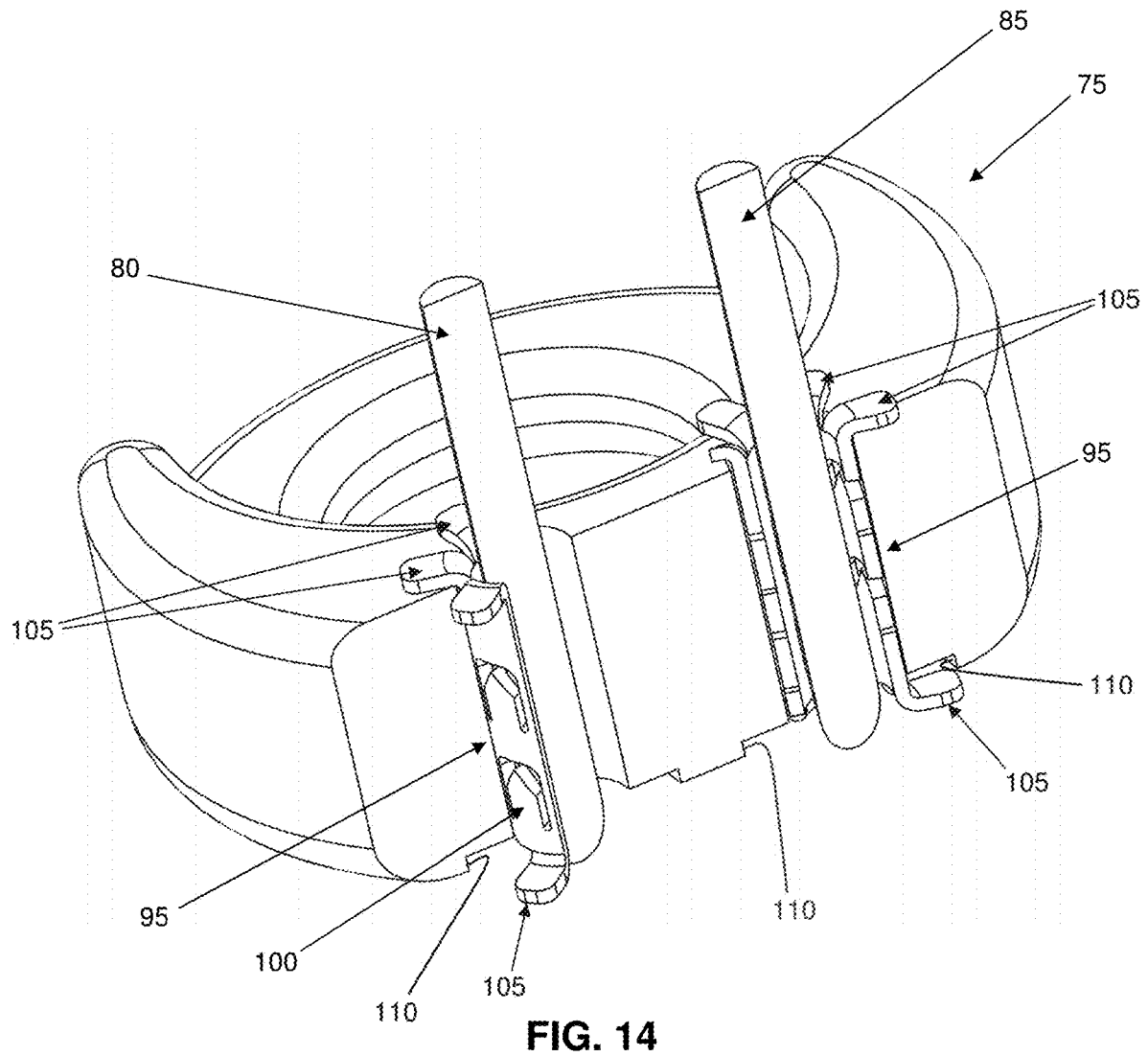
Figure 15:
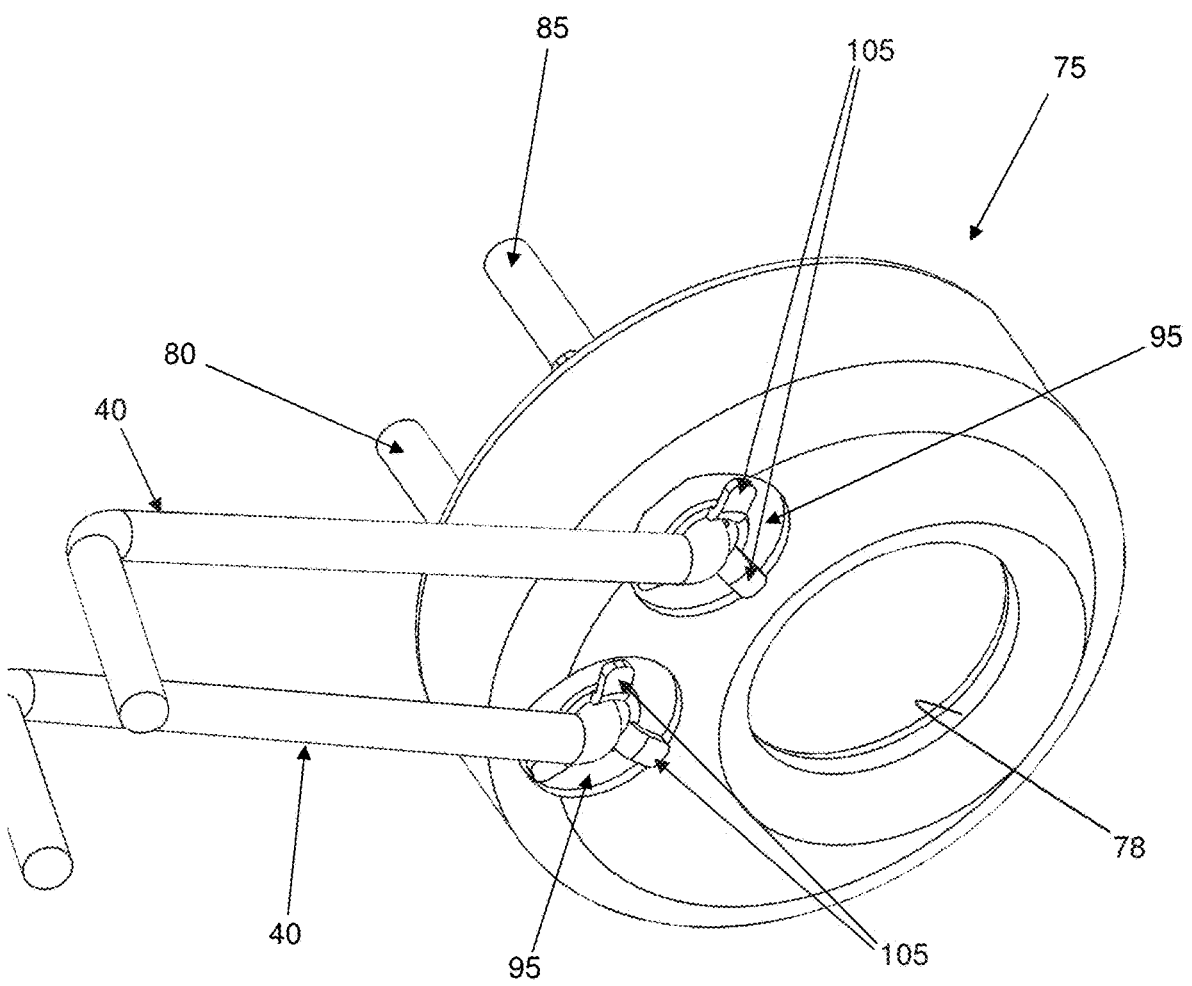
Figure 16:
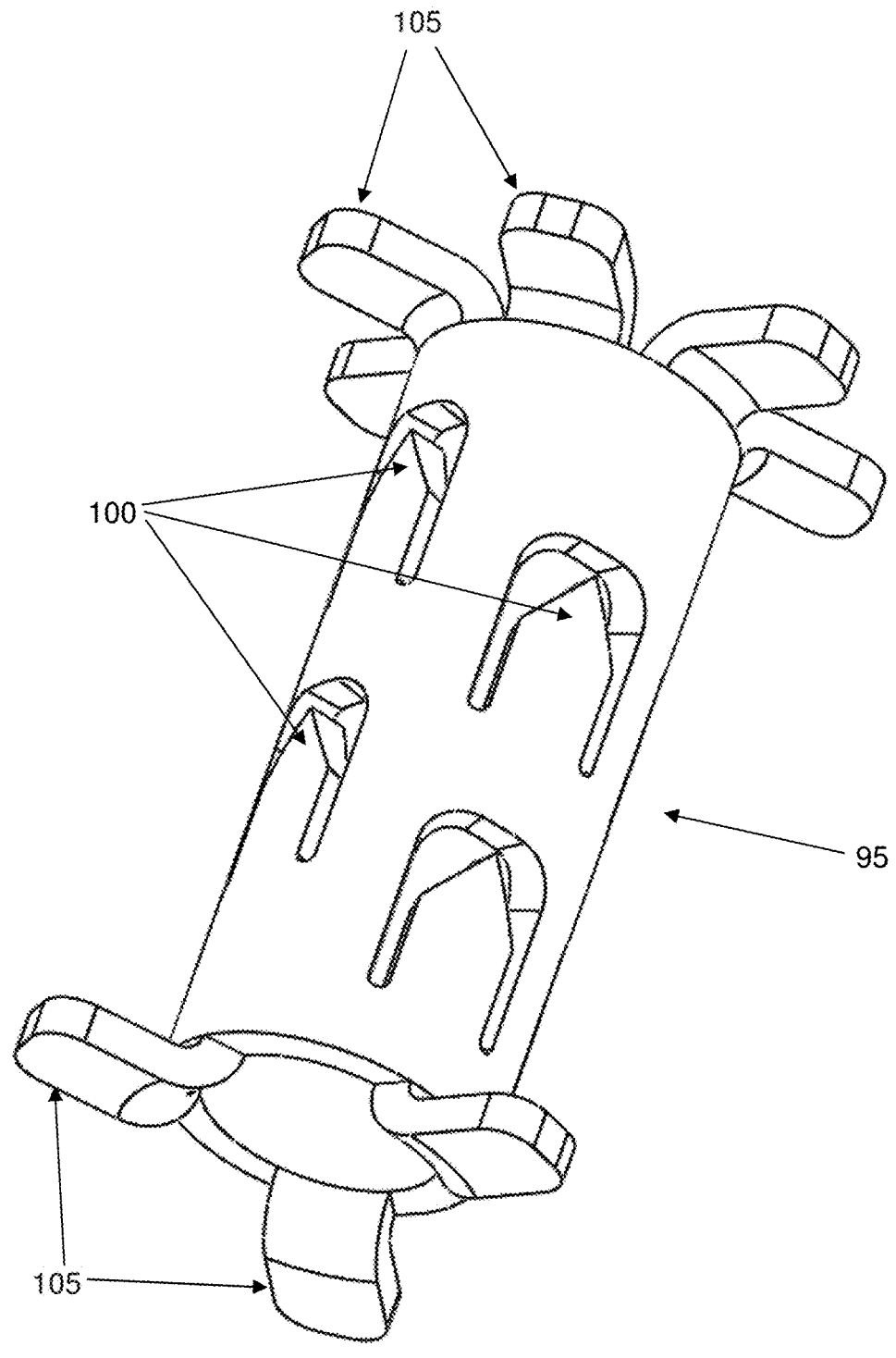
FIG. 16 is an perspective schematic view of the suture-securing mechanism shown in FIGS. 13-15.
Figures 17, 18, 19:
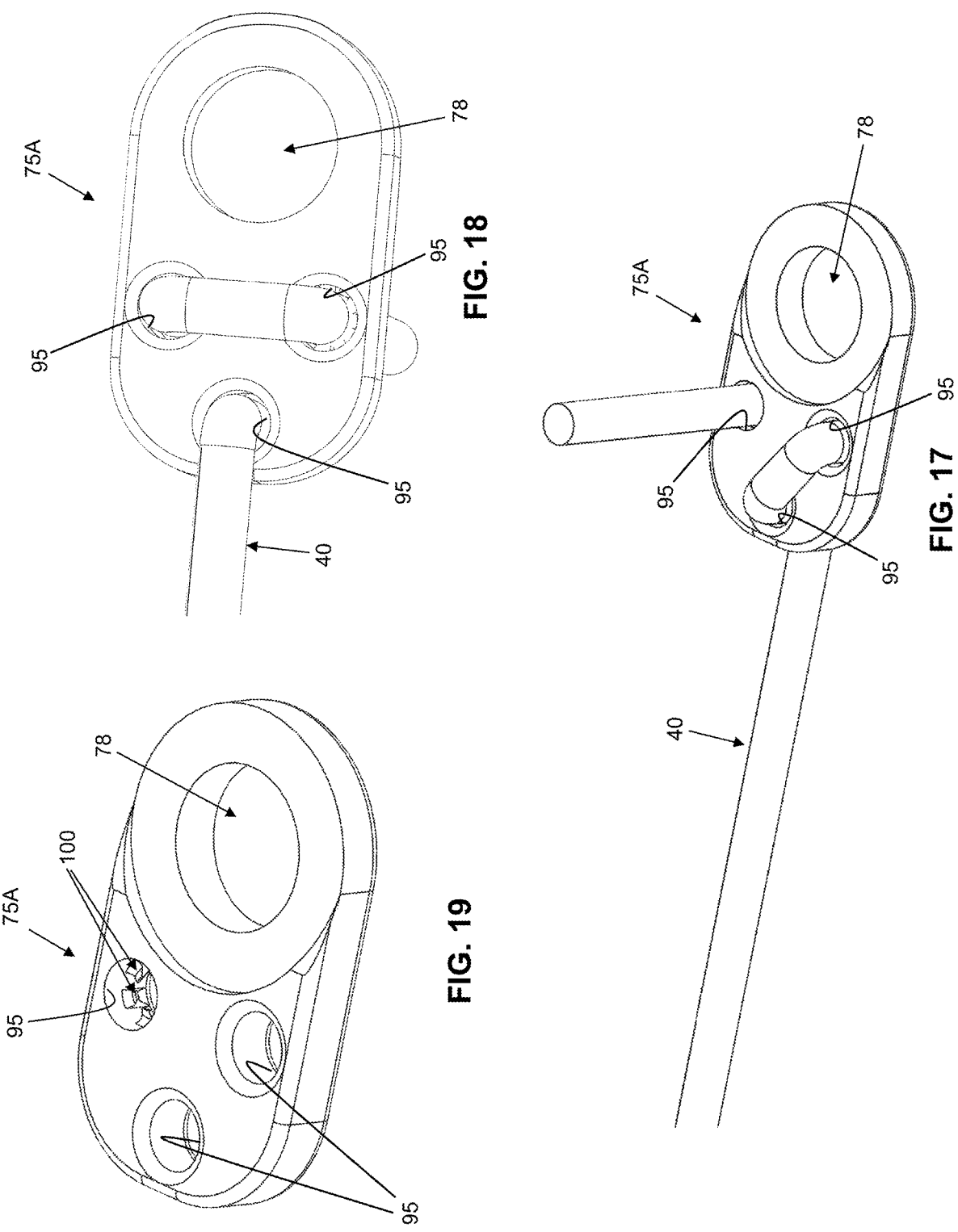
Figure 25:
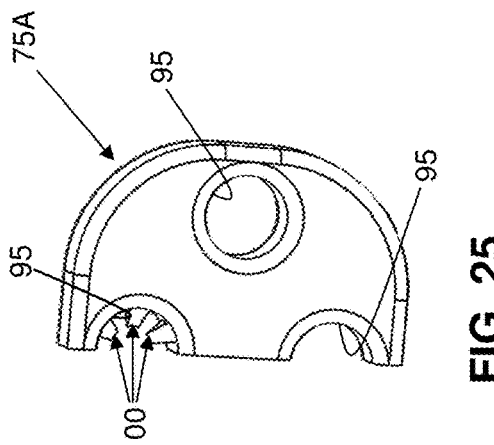
FIGS. 24-27 are various schematic sectional views of the suture-locking washer of FIGS. 17-23.
Figure 27:
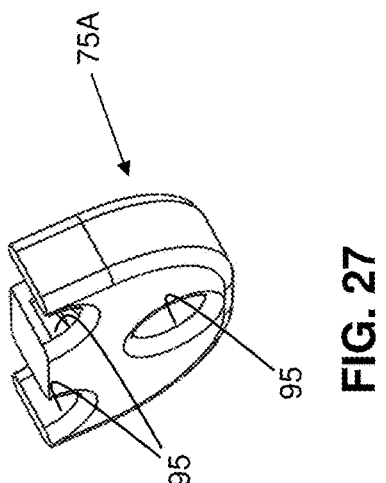
Figure 24:
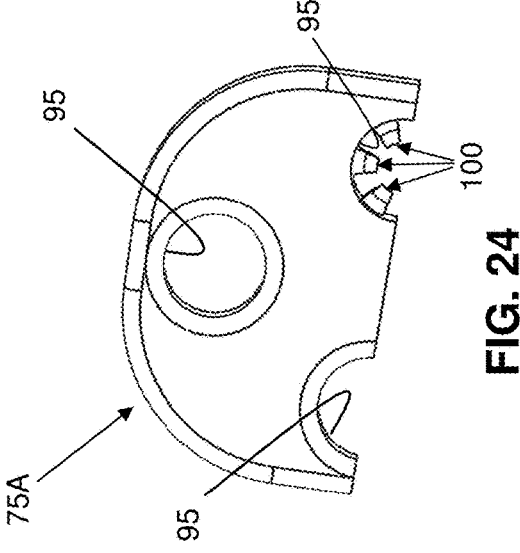
Figure 26:
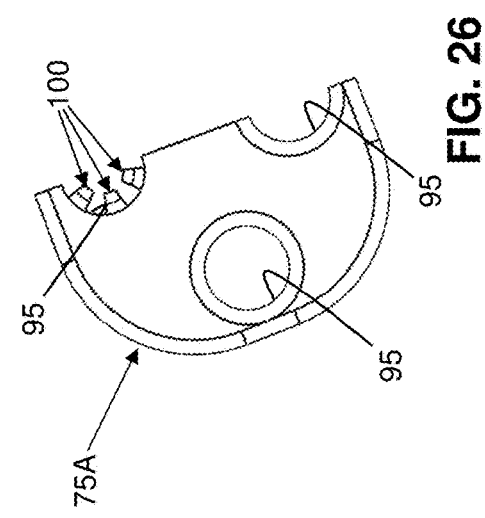

In one preferred form of the invention, and looking now at FIG. 12, tubular structures 102 start as a flat sheet of material, have suture-holding elements (barbs or teeth) 100 laser cut into the sheet of material, and then the sheet of material is bent into a tubular structure (i.e., tubular structure 102) so as to provide the complete suture-securing mechanisms 95.

Tubular structures 102 of suture-securing mechanisms 95 are fixedly secured in holes 103 formed in suture-locking washer 75, whereby to fix suture-securing mechanisms 95 relative to suture-locking washer 75. See FIG. 9.

In one preferred form of the invention, tubular structures 102 of suture-securing mechanisms 95 are press-fit into holes 103.

In another preferred form of the invention, and looking now at FIGS. 13-16, suture-securing mechanisms 95 may also comprise protrusions 105 that may be positioned to engage the outer surfaces of suture-locking washer 75 so as to maintain the position of the suture-securing mechanisms 95 relative to suture-locking washer 75. If desired, one or both ends of holes 103 may be provided with a counterbore 110 (FIG. 14) for receiving protrusions 105.

In one preferred form of the invention, suture-securing mechanisms 95 may comprise two "rows" and four "columns" (i.e., relative to the longitudinal axis of the suture-securing mechanism 95) of suture-holding elements (barbs or teeth) 100 that are offset from one another in order to prevent compressing sling 40 between the "points" of opposing barbs or teeth 100. Four columns are preferable in order to allow pre-positioning of the barbs or teeth 100 inwardly. Fewer or more rows of barbs or teeth 100 may be used, provided that the desired pull force is achieved and the height of anchor washer 75 (which is partially determined by the length of the suture-securing mechanism) is small enough to limit the profile of the thumb metacarpal anchor 45 (including the suture-locking washer 75 mounted thereto) from extending above the base of thumb metacarpal 15 upon deployment of thumb metacarpal anchor 45. If desired, suture-securing mechanisms 95 may comprise fewer columns with longer barb or teeth widths so that the barbs or teeth 100 do not fracture or weaken upon deflecting, and/or barbs or teeth 100 may be pre-positioned inwardly so as to allow engagement of sling 40. Such a pattern of barbs or teeth 100 increases the pull force while limiting damage to sling 40.

It should also be appreciated that alternative shapes and/or numbers of barbs or teeth 100 may be utilized to engage sling 40.

Use of the Novel Sling Suspension System

Sling suspension system 30 may be used in the following manner to support the thumb of a patient after a basal joint arthroplasty has been performed to alleviate basal joint arthritis.

1. The patient's trapezium is excised (see FIG. 2) to alleviate the basal joint arthritis.
2. Index metacarpal 25 and thumb metacarpal 15 are prepared to receive index metacarpal anchor 35 and thumb metacarpal anchor 45, respectively. In one preferred form of the invention, a bone hole is drilled into the thumb side of index metacarpal 25, and a bone hole is drilled into the base of thumb metacarpal 15. Note that the space created by the excised trapezium allows easy access to the base of thumb metacarpal 15 and to the thumb side of index metacarpal 25.
3. Sling 40 is attached to index metacarpal anchor 35 using sling-engaging element 60 (e.g., an eyelet) of index metacarpal anchor 35 and an anchor-engaging element (e.g., a knot) of sling 40, and sling 40 is attached to suture-locking washer 75 and suture-locking washer 75 is attached to thumb metacarpal anchor 45, if they are not already in this arrangement. See FIG. 3.
4. Index metacarpal anchor 35 is secured in the bone hole formed in index metacarpal 25.
5. Thumb metacarpal anchor 45 is secured in the bone hole formed in the base of thumb metacarpal 15.

6. The free end(s) 80, 85 of sling 40 is/are tensioned (i.e., cinched), whereby to correctly position thumb metacarpal anchor 45 relative to index metacarpal anchor 35, and hence to correctly position thumb metacarpal 15 relative to index metacarpal 25, so as to provide the desired reconstructed basal joint. See FIG. 3.
7. Free end(s) 80, 85 of secured sling 45 can then be cut with an appropriate instrument if desired.

Alternative Form of Suture-Locking Washer

FIGS. 17-27 show an alternative suture-locking washer 75A wherein the one or more suture-securing mechanisms 95 are formed integral with the body of suture-locking washer 75A (i.e., the side walls of 25 suture-securing mechanisms 95 are the side walls of holes 103 passing through the suture-locking washer). See FIGS. 19 and 24-26. In this form of the invention, suture-locking washer 75A comprises multiple holes 103 for sling 40 (i.e., a suture) to pass through, with at least one of the holes 103 including suture-holding elements (barbs or teeth) 100 positioned so as to allow passage of sling 40 in one direction while preventing slippage of the sling in the opposite direction. Others of holes 103 may omit barbs or teeth 100 (i.e., others of holes 103 may comprise smooth inside walls).

Deployment Assembly

Figure 28:
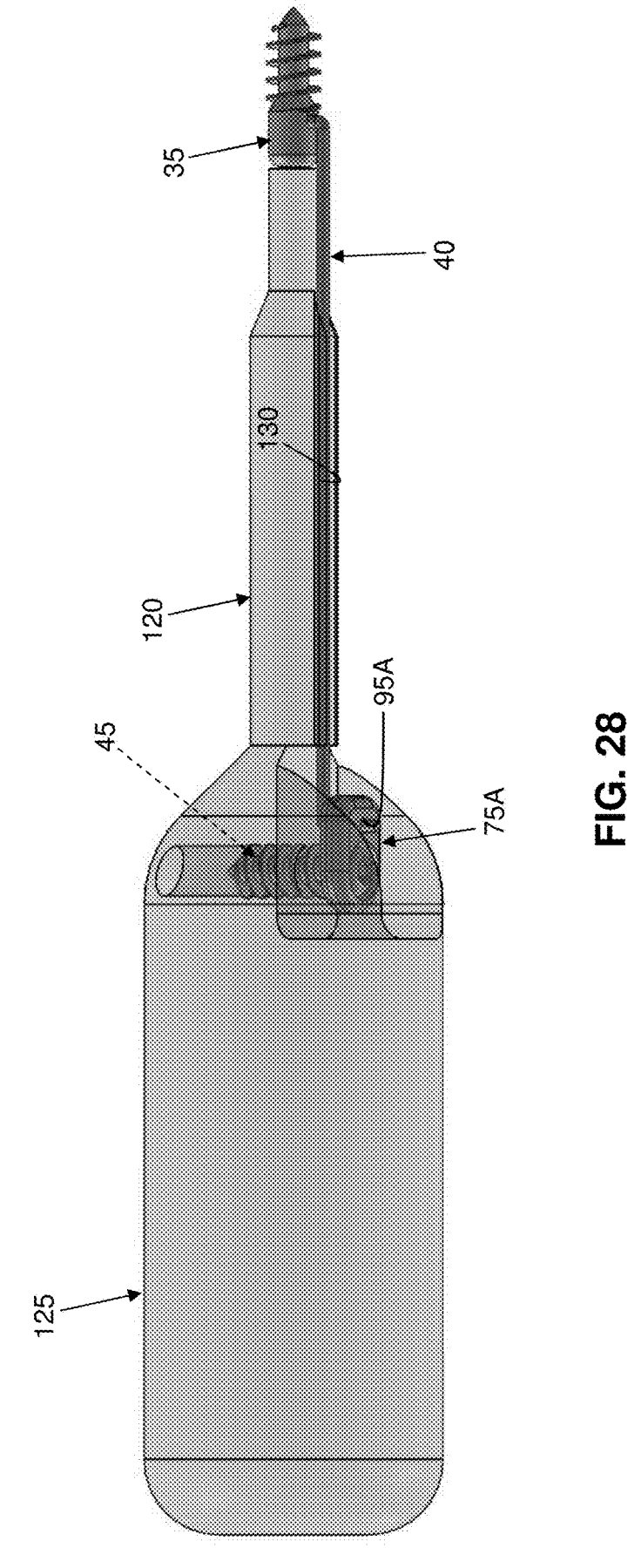
FIGS. 28-30 are schematic views of a deployment assembly for deploying the novel sling suspension system of the present invention.
Figure 29:
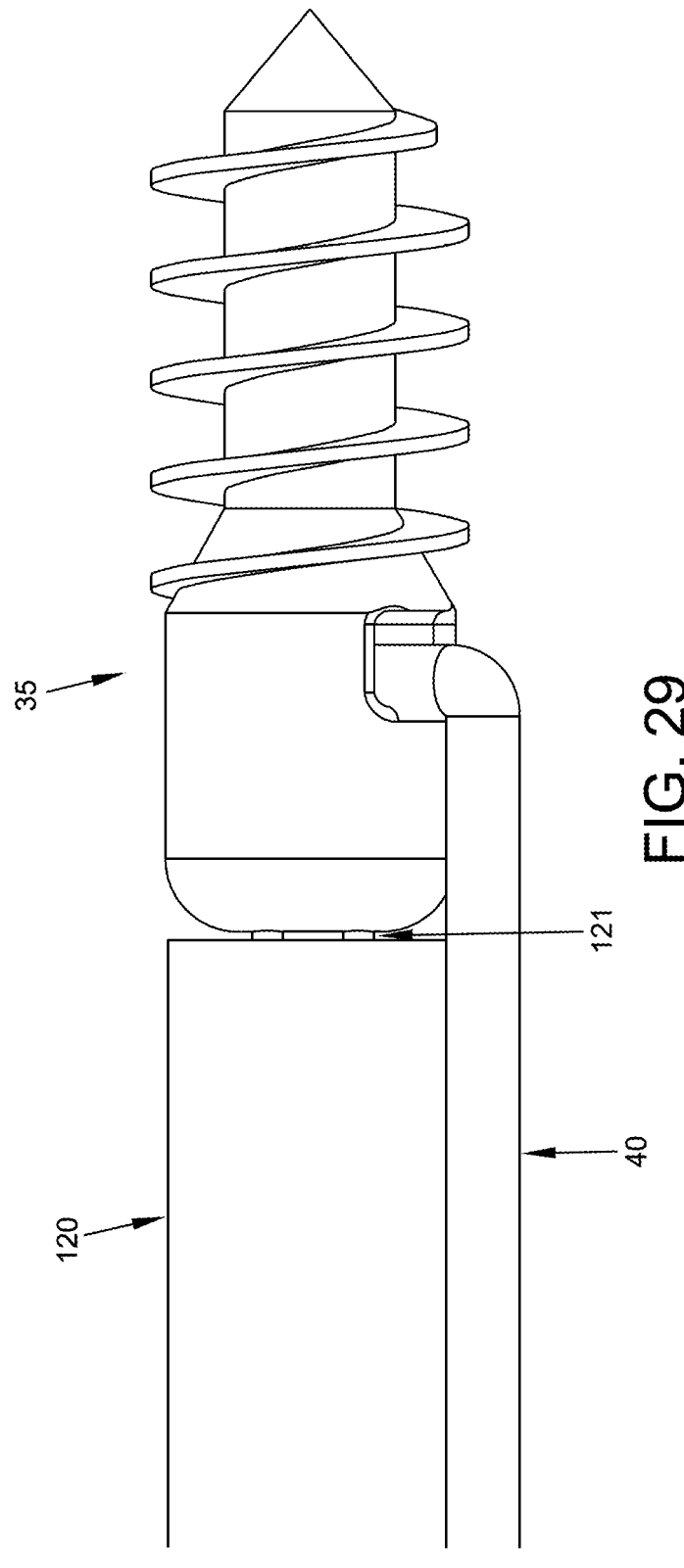
Figure 30:
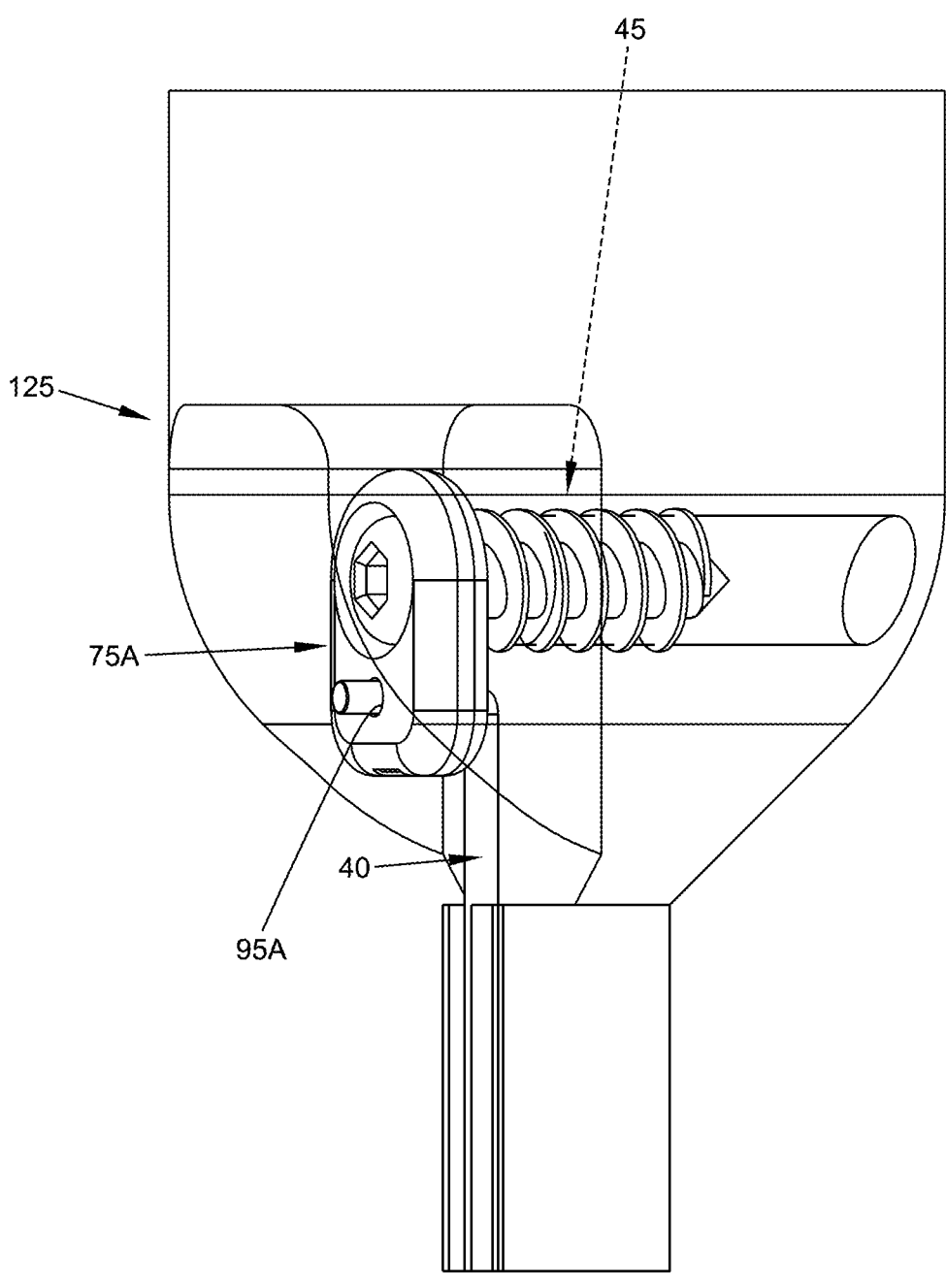

Looking now at FIGS. 28-30, there is shown a deployment assembly 115 which may be used to deploy sling suspension system 30. More particularly, deployment assembly 115 may be used to set index metacarpal anchor 35 into index metacarpal 25 (e.g., to insert index metacarpal anchor 35 into a bone hole formed in index metacarpal 25) and/or to set thumb metacarpal anchor 45 into thumb metacarpal 15 (e.g., to insert thumb metacarpal anchor 45 into a bone hole formed in thumb metacarpal 15). To this end, deployment assembly 115 preferably comprises a shaft 120 having a drive feature (e.g., a hex driver) 121 (FIG. 29) at its distal end for engaging (i) a counterpart drive feature (e.g., a hexagonal recess) 122 (FIG. 3) formed in the proximal end of index metacarpal anchor 35 so as to enable deployment assembly 115 to be used to drive index metacarpal anchor 35 into index metacarpal 25, and/or (ii) a counterpart drive feature (e.g., a hexagonal recess) 123 (FIG. 9) formed on the proximal end of thumb metacarpal anchor 45 so as to enable deployment assembly 115 to be used to drive thumb metacarpal anchor 45 into thumb metacarpal 15.

A handle 125 (FIG. 28) is provided at the proximal end of shaft 120 of deployment assembly 115.

In one exemplary form of the invention, suture-locking washer 75A is affixed to thumb metacarpal anchor 45 at the time of manufacture, so that the surgeon does not have to worry about fixing the suture-locking washer to the thumb metacarpal anchor at the time of use. See FIG. 28.

And in one exemplary form of the invention, index metacarpal anchor 35 is pre-loaded onto the distal end of shaft 120 of deployment assembly 115 at the time of system assembly, e.g., as shown in FIGS. 28 and 29. Thumb metacarpal anchor 45, with suture-locking washer 75A pre-affixed thereto, is preferably pre-loaded onto handle 125 of deployment assembly 115 (FIGS. 28 and 30). After deployment assembly 115 has been used to set index metacarpal anchor 35 into index metacarpal 25, thumb metacarpal anchor 45 (with suture-locking washer 75A pre-affixed thereto) is loaded on the distal end of shaft 120 of deployment assembly 115 and deployment assembly 115 is then used to set thumb metacarpal anchor 45 (with suture-locking washer 75A pre-affixed thereto) into thumb metacarpal 15.

Where index metacarpal anchor 35 is pre-loaded onto deployment assembly 115 at the time of system assembly, deployment assembly 115 is preferably provided with a channel 130 (FIGS. 28 and 30) that allows passage of sling 40 along shaft 120 to a suture-locking washer 75A mounted onto a thumb metacarpal anchor 45.

Alternative Deployment Assembly

Figure 31:
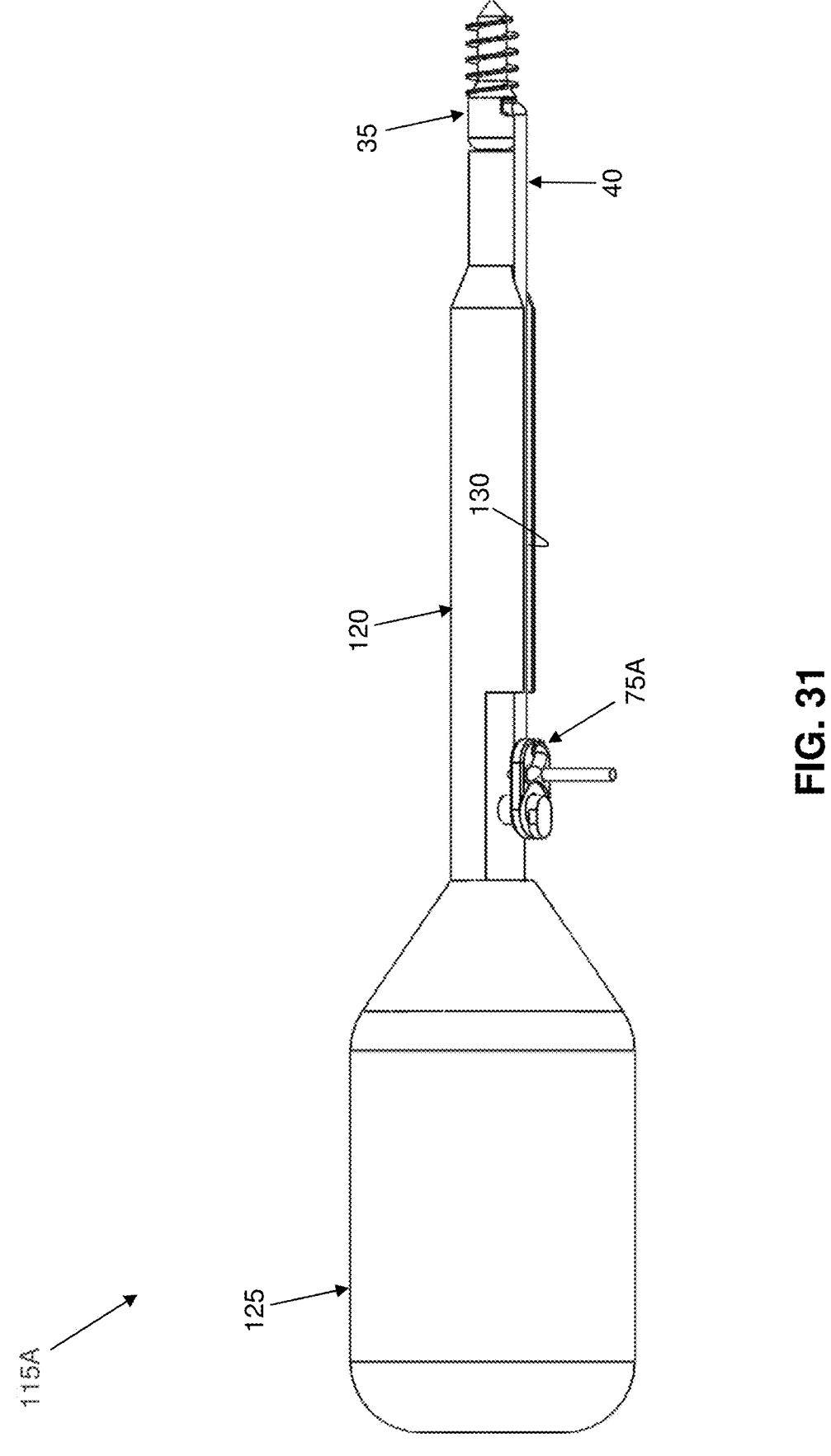
FIGS. 31 and 32 are schematic views of another deployment assembly for deploying the novel sling suspension system of the present invention.
Figure 32:
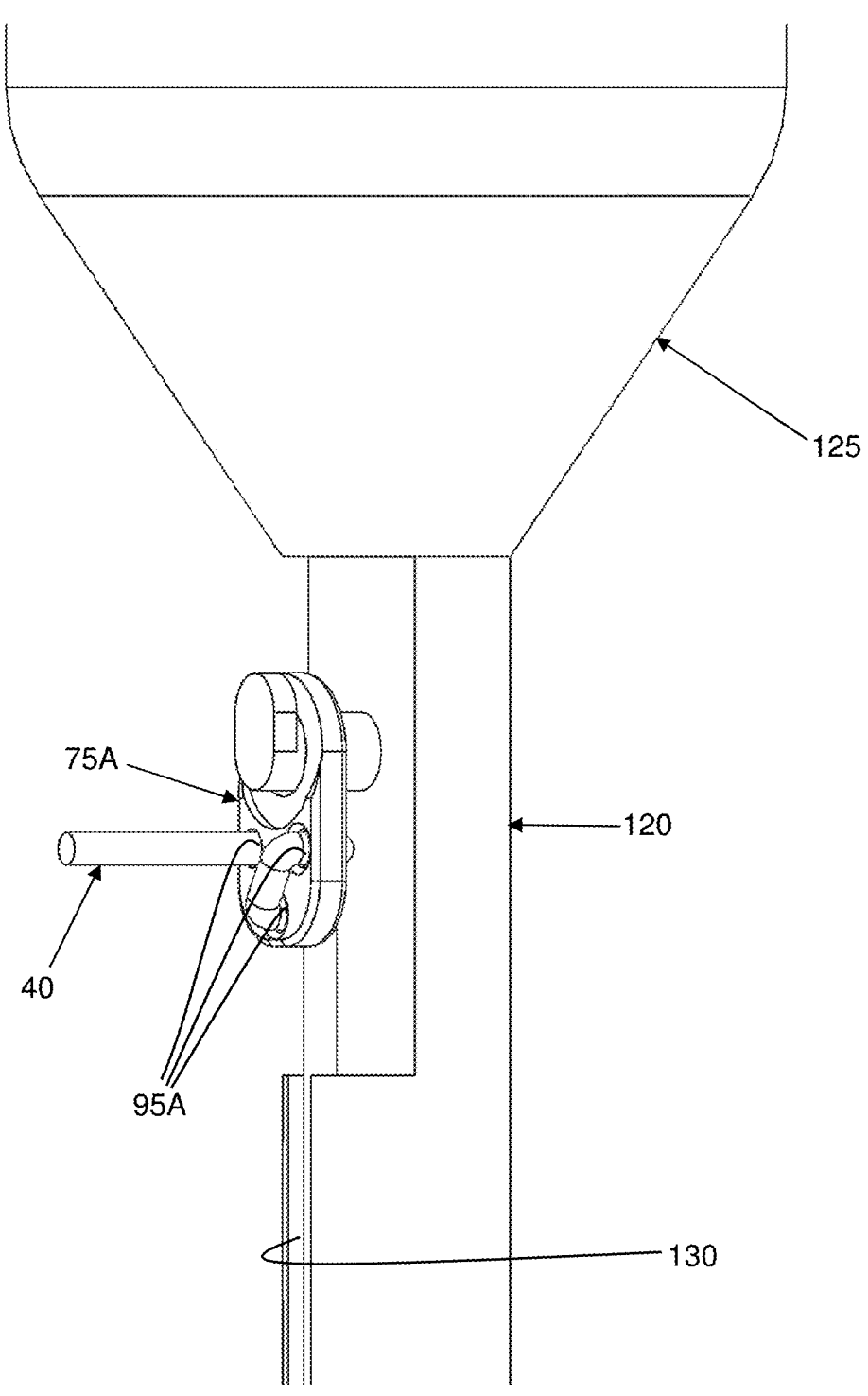

FIGS. 31 and 32 show another form of deployment assembly 115A, wherein thumb metacarpal anchor 45 is loaded onto shaft 120 of deployment assembly 115A (as opposed to thumb metacarpal anchor 45 being loaded onto handle 125 of deployment assembly 115).

Another Suture-Locking Washer and Thumb Metacarpal Anchor

Figure 33:
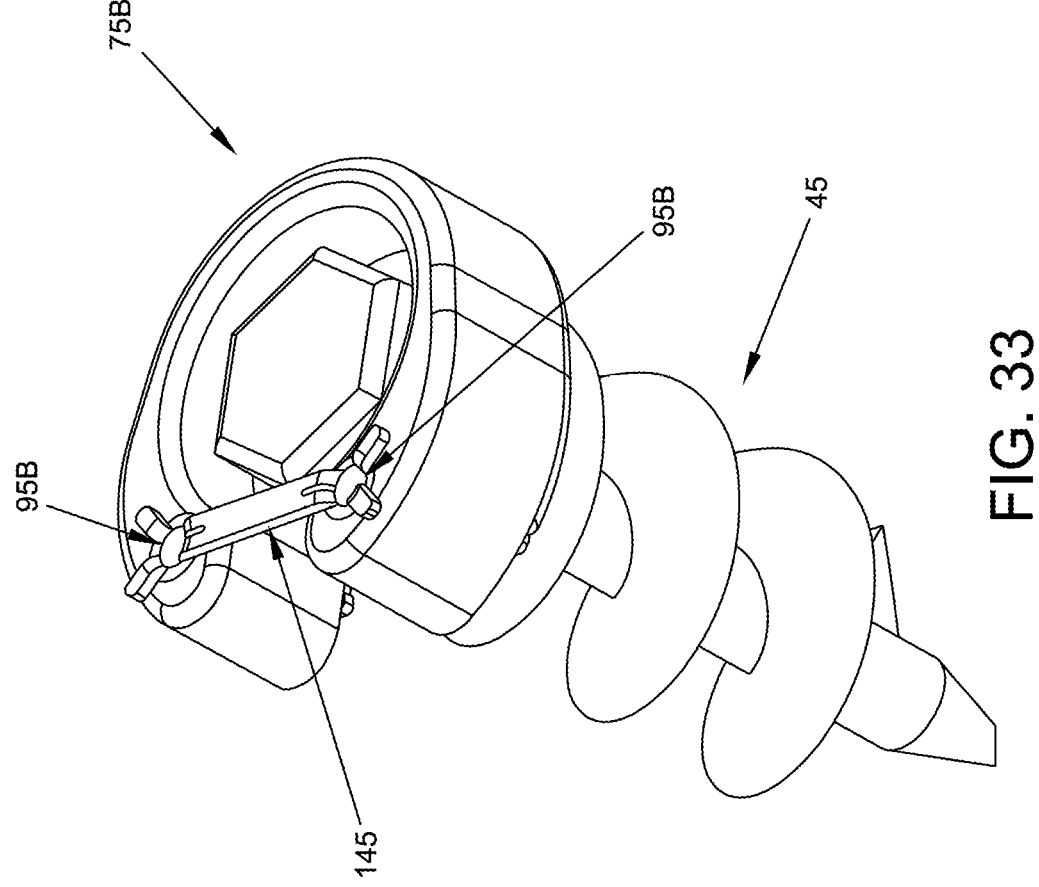
FIGS. 33-53 are schematic views illustrating another novel suture-locking washer and thumb metacarpal anchor formed in accordance with the present invention.
Figures 34, 35, 36, 37:
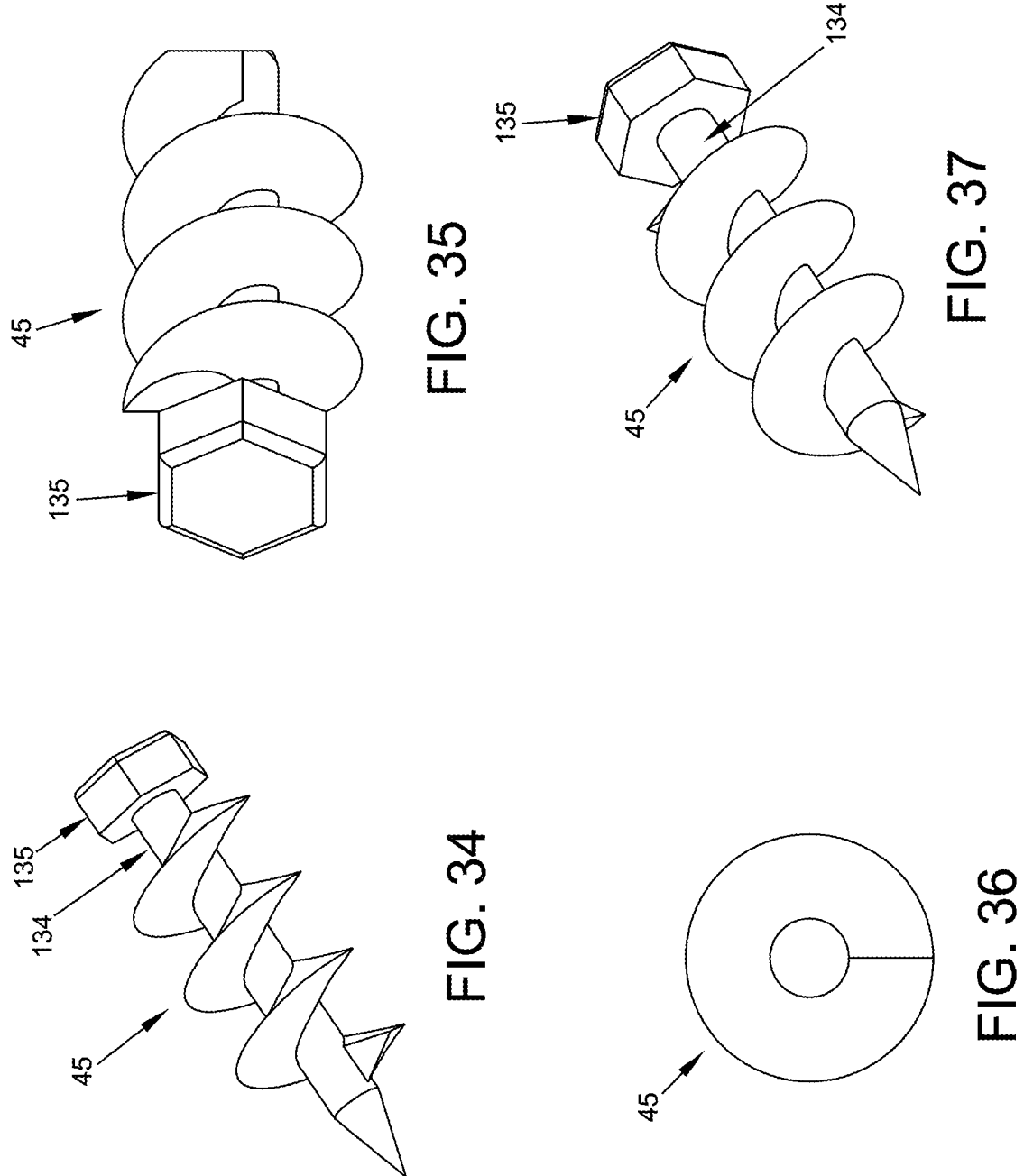
Figure 39:
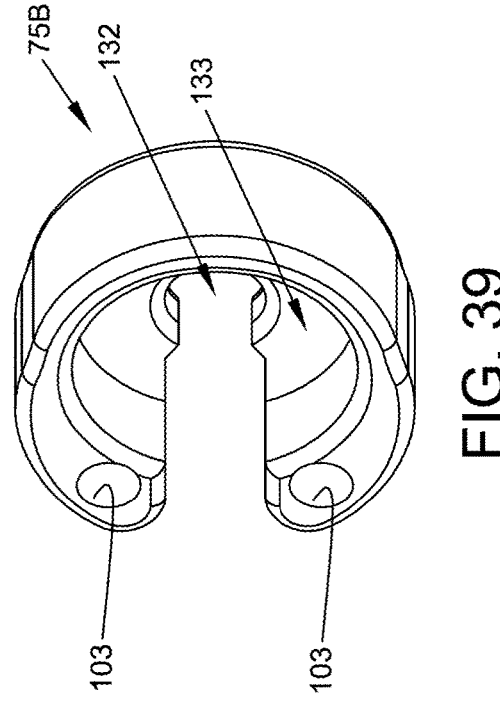
Figure 41:
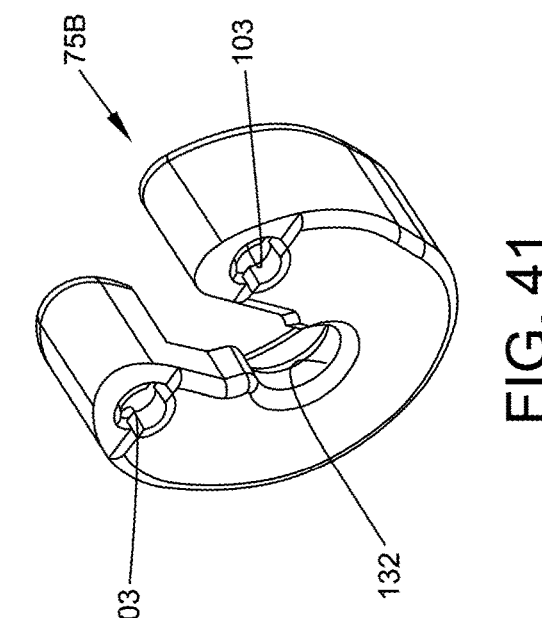
Figure 38:
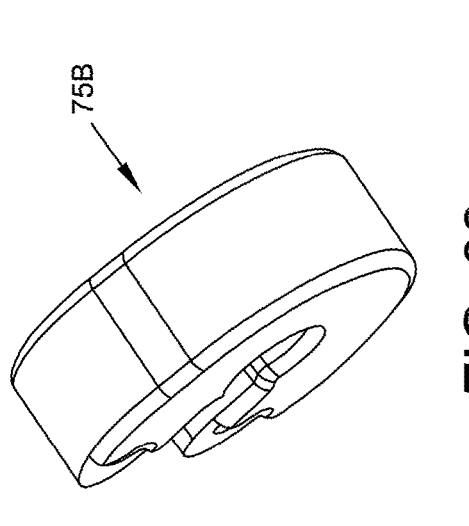
Figure 40:
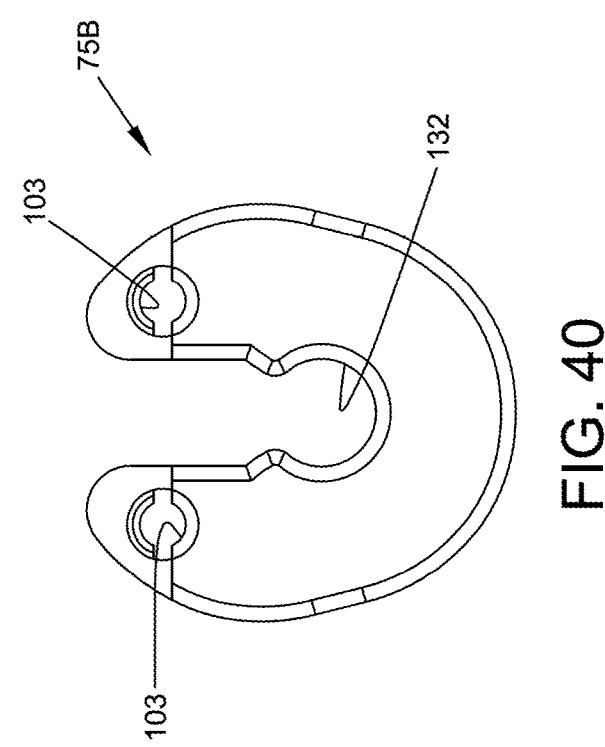
Figures 42, 43, 44, 45:
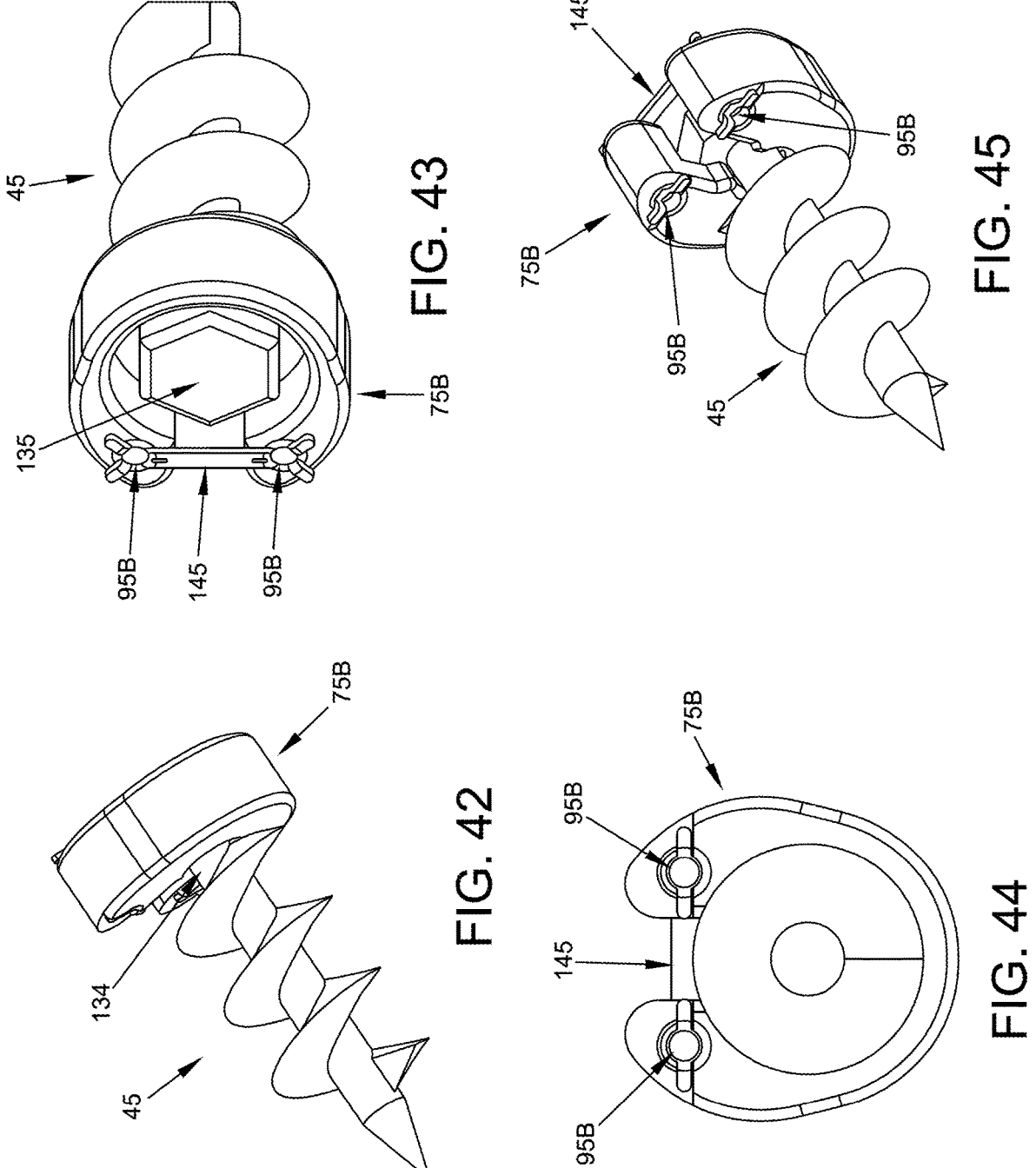
Figures 46, 47, 48:
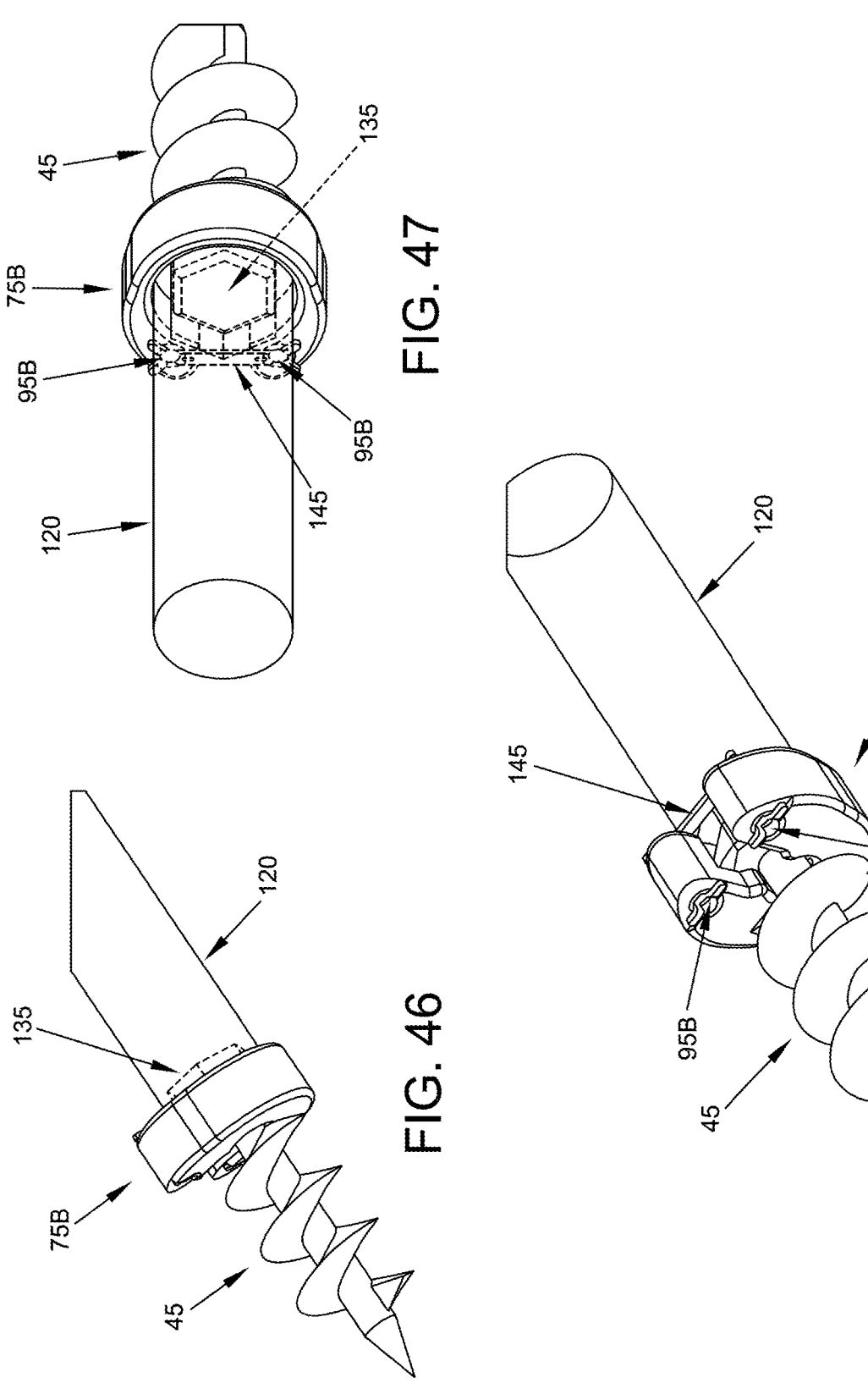
Figure 50:
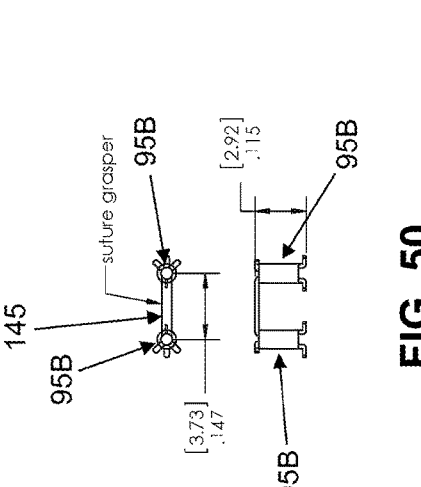
Figure 52:
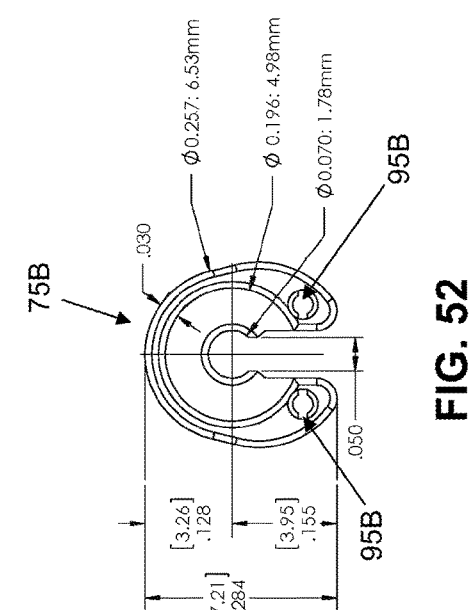
Figure 49:
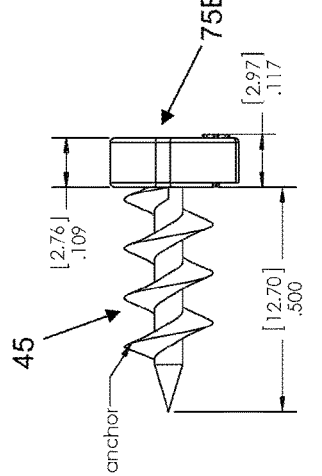
Figure 51:
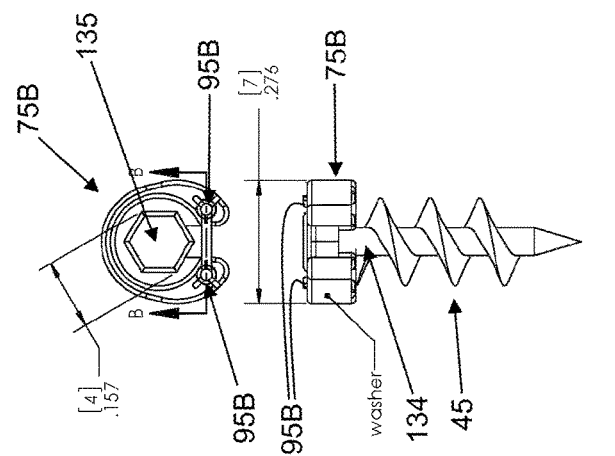
Figure 53:
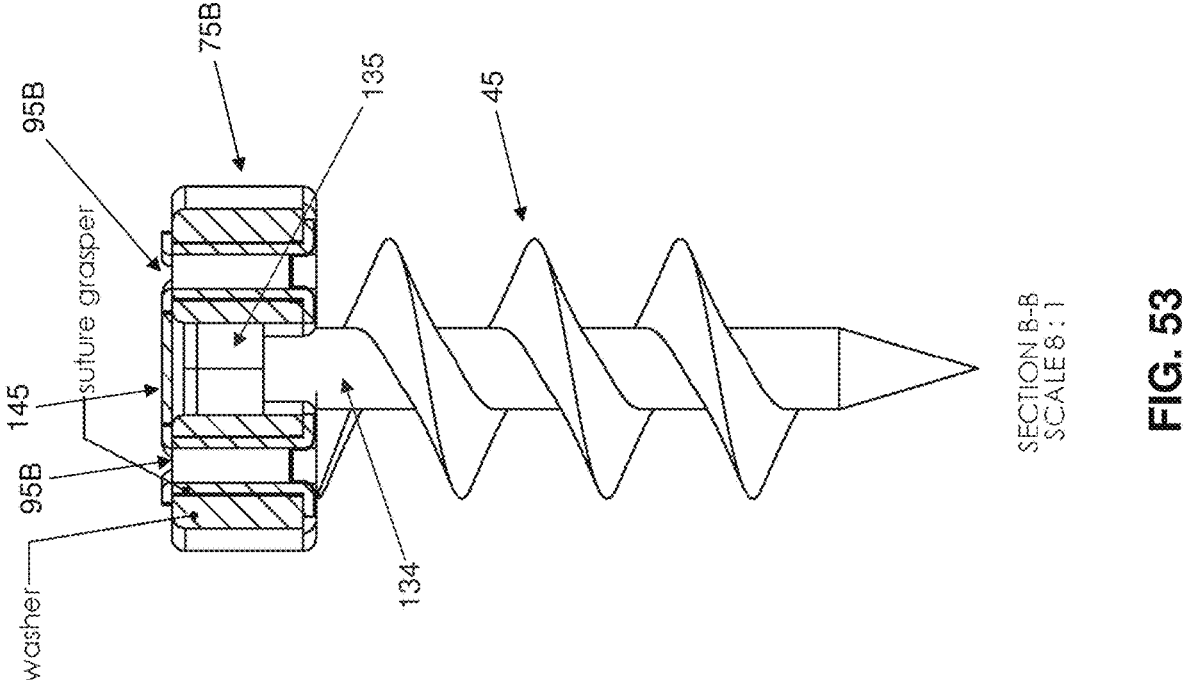

FIGS. 33-53 show still another form of suture-locking washer and thumb metacarpal anchor formed in accordance with the present invention. More particularly, in this form of the invention, there is provided a suture-locking washer 75B comprising at least two suture-securing mechanisms 95B. See FIG. 33. Suture-locking washer 75B is configured to mount to the proximal end of a screw-type thumb metacarpal anchor 45, whereby to permit the suture to be knotlessly secured to thumb metacarpal anchor 45. Anchor washer 75B is generally C-shaped (FIGS. 39-41) and preferably comprises a bore 132 and a counterbore 133, wherein bore 132 receives the shaft 134 of thumb metacarpal anchor 45 (FIG. 43) and counterbore 133 receives the head 135 of thumb metacarpal anchor 45, whereby to facilitate mounting anchor washer 75B to the proximal end of thumb metacarpal anchor 45. In this form of the invention, suture-securing mechanisms 95B preferably comprise a connecting bar 145 (see FIGS. 33 and 43) for connecting one suture-securing mechanism 95B to an adjacent suture-securing mechanism 95B, and for securing anchor washer 75B to the proximal end of thumb metacarpal anchor 45. It should be appreciated that anchor washer 75B may be secured to thumb metacarpal anchor 45 and/or sling 40 and/or 15 deployment assembly 115 at the time of manufacture and may be sterilized as a unit prior to delivery to an end user (e.g., a surgeon).

Suture-Locking Washer for Securing Suture Perpendicular to the Longitudinal Axis of an Anchor In the foregoing disclosure, suture-locking washers 75, 75A and 75B are disclosed as having suture-securing mechanisms 95 mounted to the suture-locking washer such that (a) free end(s) of sling 40 (e.g., the free end(s) of a suture) can be passed through a given suture-securing mechanism 95 which is, in turn, mounted to a given suture-locking washer 75, 75A or 75B, whereby to facilitate knotless securement of the free end(s) of sling 40 to a suture-locking washer 75, 75A, 75B.

And, in the foregoing disclosure, the aforementioned suture-locking washers 75, 75A and 75B are disclosed as having one or more suture-securing mechanisms 95 disposed parallel to the longitudinal axis of an anchor to which the suture-locking washer 75, 75A and 75B is attached. See, for example, FIGS. 9, 30 and 53.

However, it should also be appreciated that, if desired, the one or more holes 103 formed in the suture-locking washer which are configured to receive the one or more suture-securing mechanisms 95 may be disposed perpendicular (rather than parallel) to the longitudinal axis of an anchor to which the suture-locking washer is mounted. Thus, in one form of the invention, suture-securing mechanisms 95 are disposed perpendicular to the longitudinal axis of an anchor to which the suture locking washer is mounted.

Figure 54:
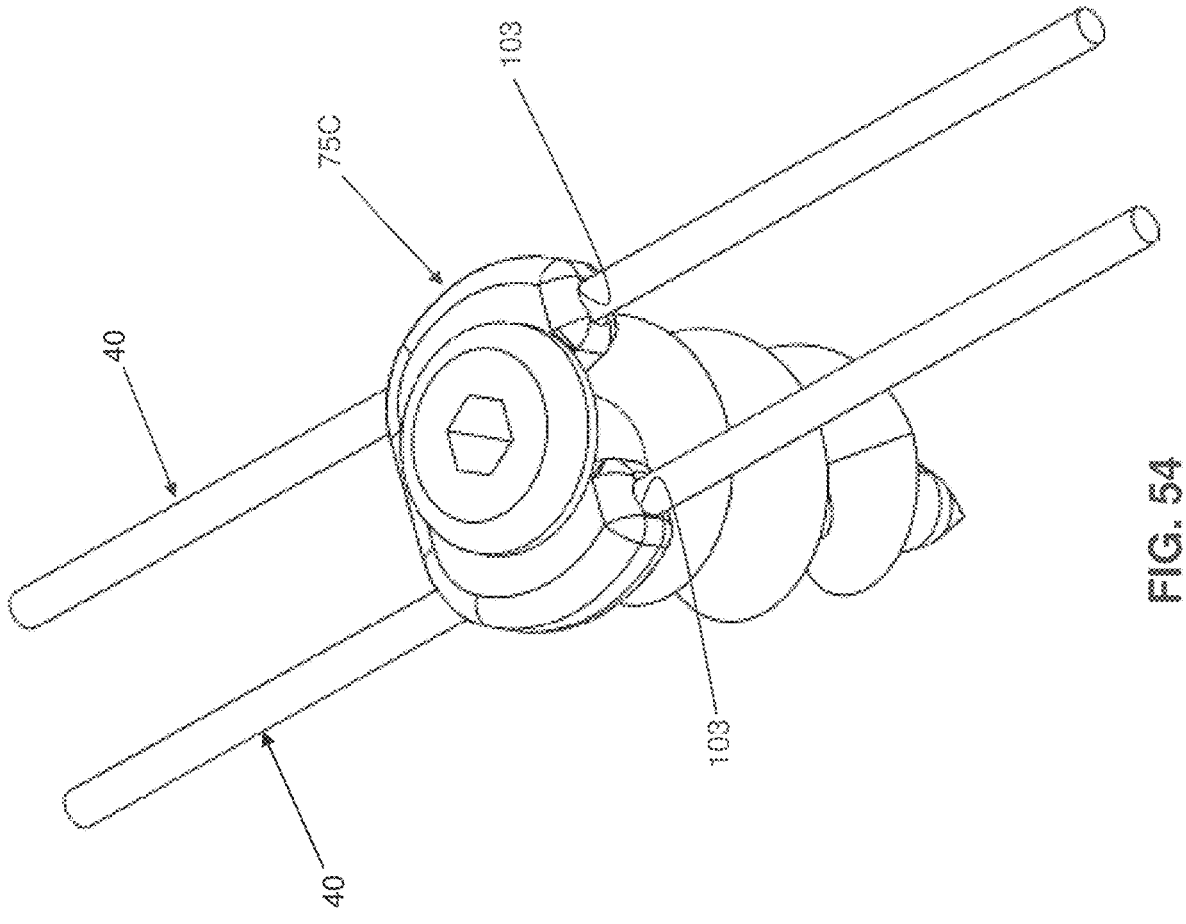
FIGS. 54-57 are schematic views illustrating another novel suture-locking washer and thumb metacarpal anchor formed in accordance with the present invention.
Figure 55:
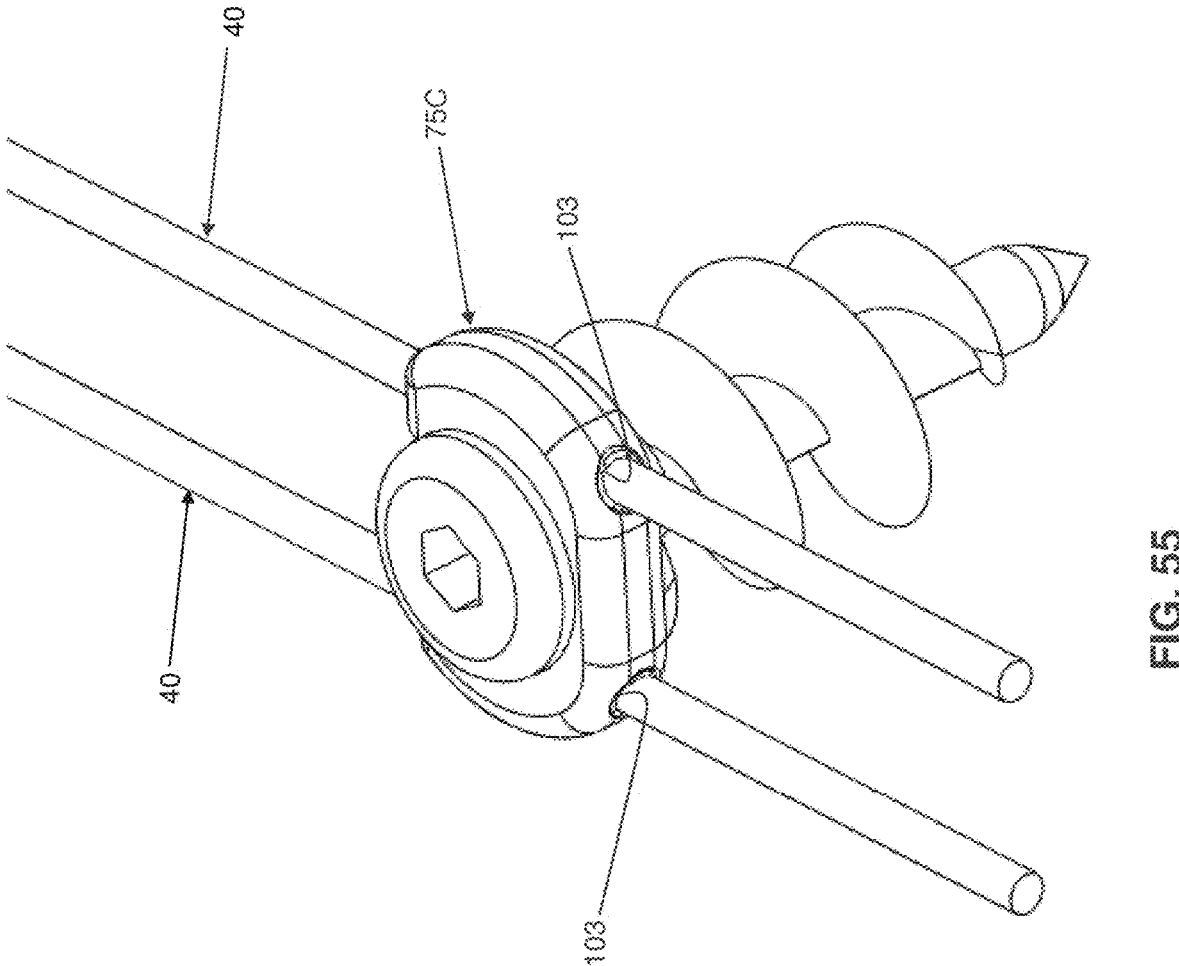

By way of example but not limitation, and looking now at FIGS. 54 and 55, there is shown a novel suture-locking washer 75C formed in accordance with the present invention. Suture-locking washer 75C comprises a plurality of holes 103 oriented perpendicular to the longitudinal axis of an anchor to which suture-locking washer 75C is mounted.

Figure 56:
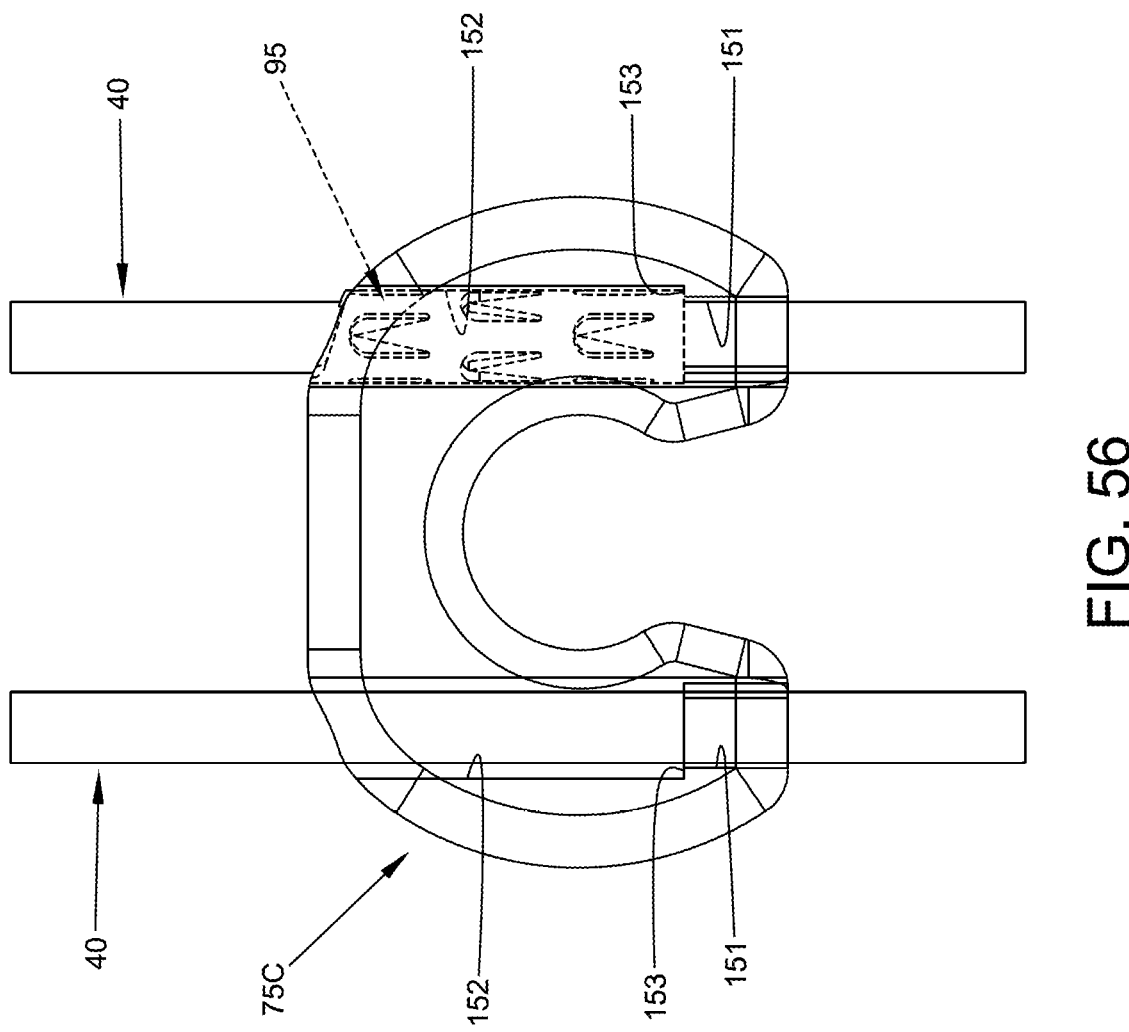

In this form of the invention, and looking now at FIG. 56, holes 103 preferably comprise stepped bores 151 and 152, which together define a shoulder 153 formed therein. Shoulder 153 provides a stop for seating a suture-securing mechanism 95 within a hole 103. Note that, if desired, similar shoulders may be provided in holes 103 of suture-locking washers 75, 75A and 75B.

Figure 57:
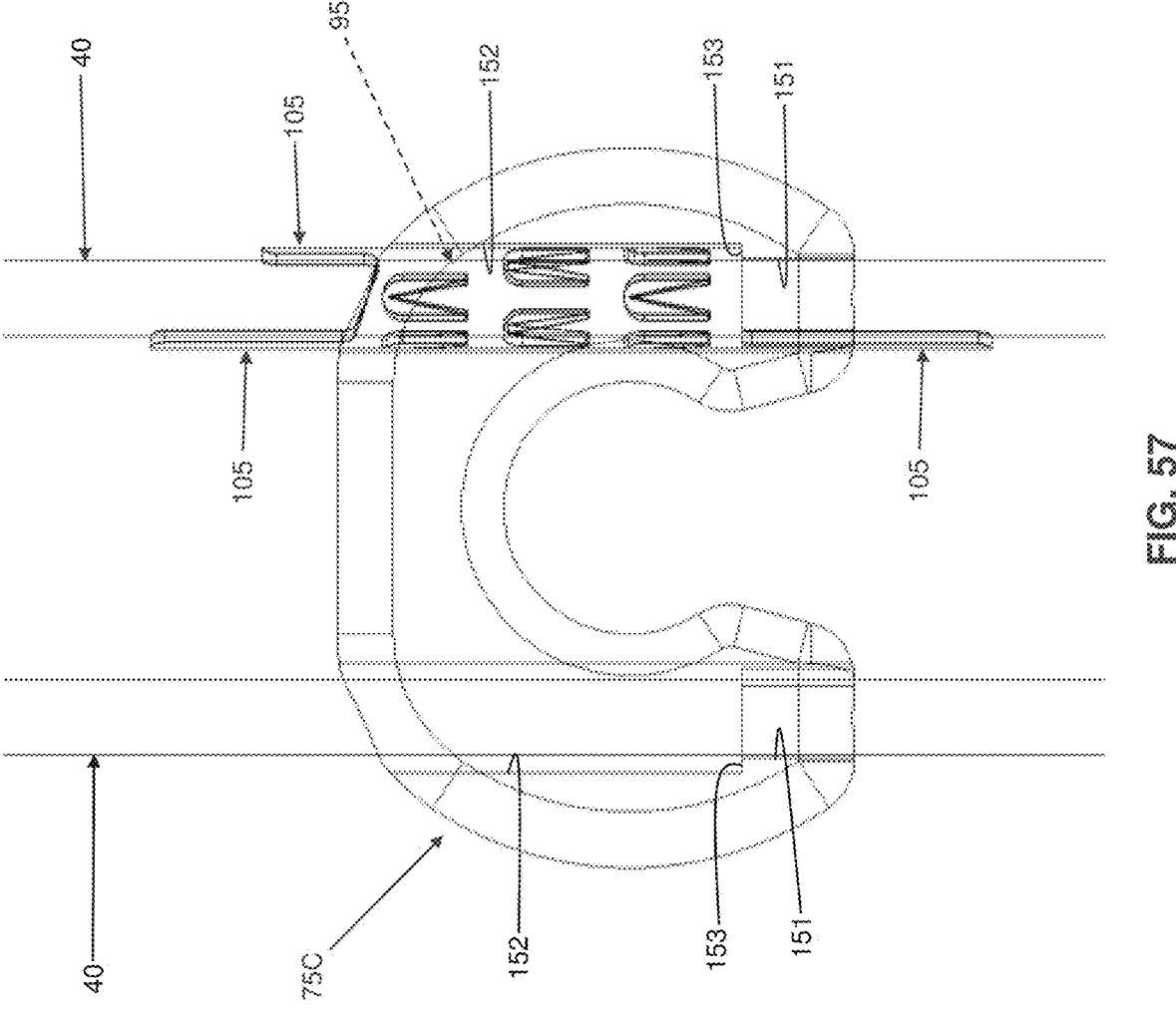

It should be appreciated that, in this form of the invention, suture-securing mechanism 95 may also comprise the aforementioned protrusions 105 for securing suture-securing mechanisms 95 to suture-locking washers 75C, i.e., in the manner previously discussed. See FIG. 57. It should also be appreciated that, in this form of the invention, shoulder 153 may be cut-away as appropriate to enable one or more protrusions 105 to extend out of bores 151.

In one form of the invention, suture-securing mechanisms 95 may be mounted to suture-locking washer 75C (or to suture-locking washers 75, 75A or 75B) before sling 40 is passed through suture-securing mechanisms 95.

Figure 58:
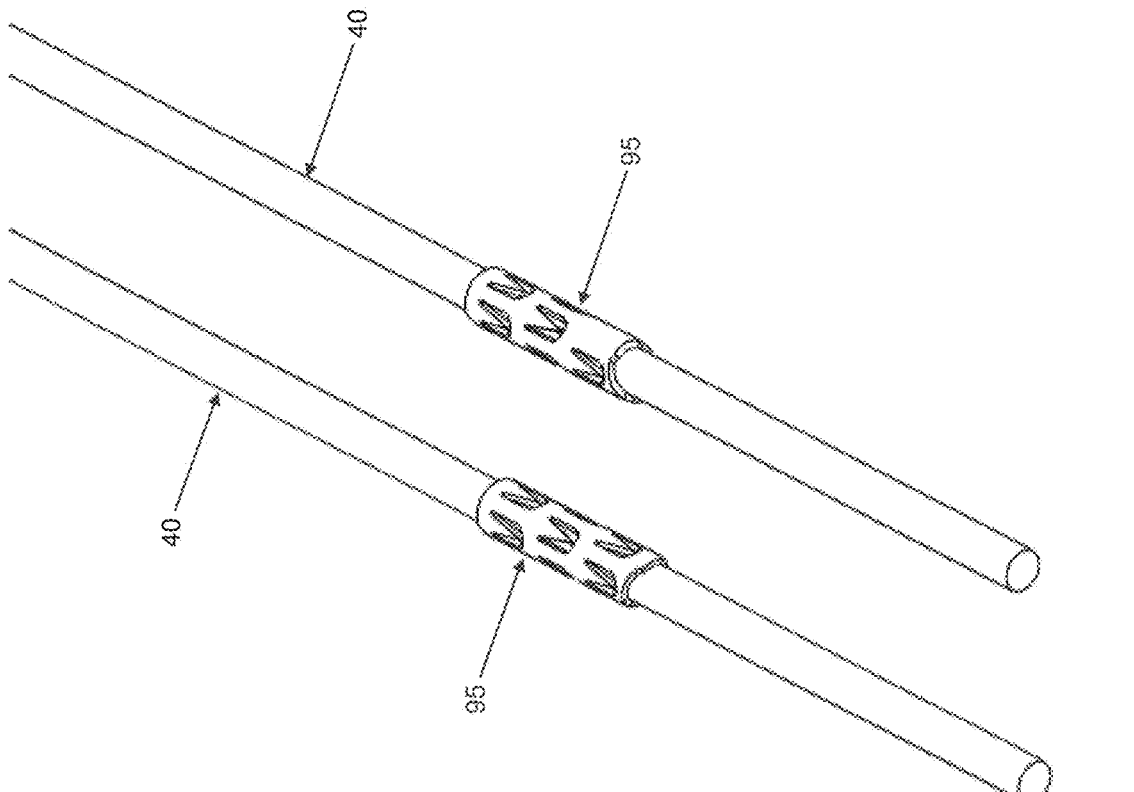
FIGS. 58-61 are schematic views illustrating how the suture-securing mechanisms of the present invention may be mounted within the suture-locking washers.
Figure 59:
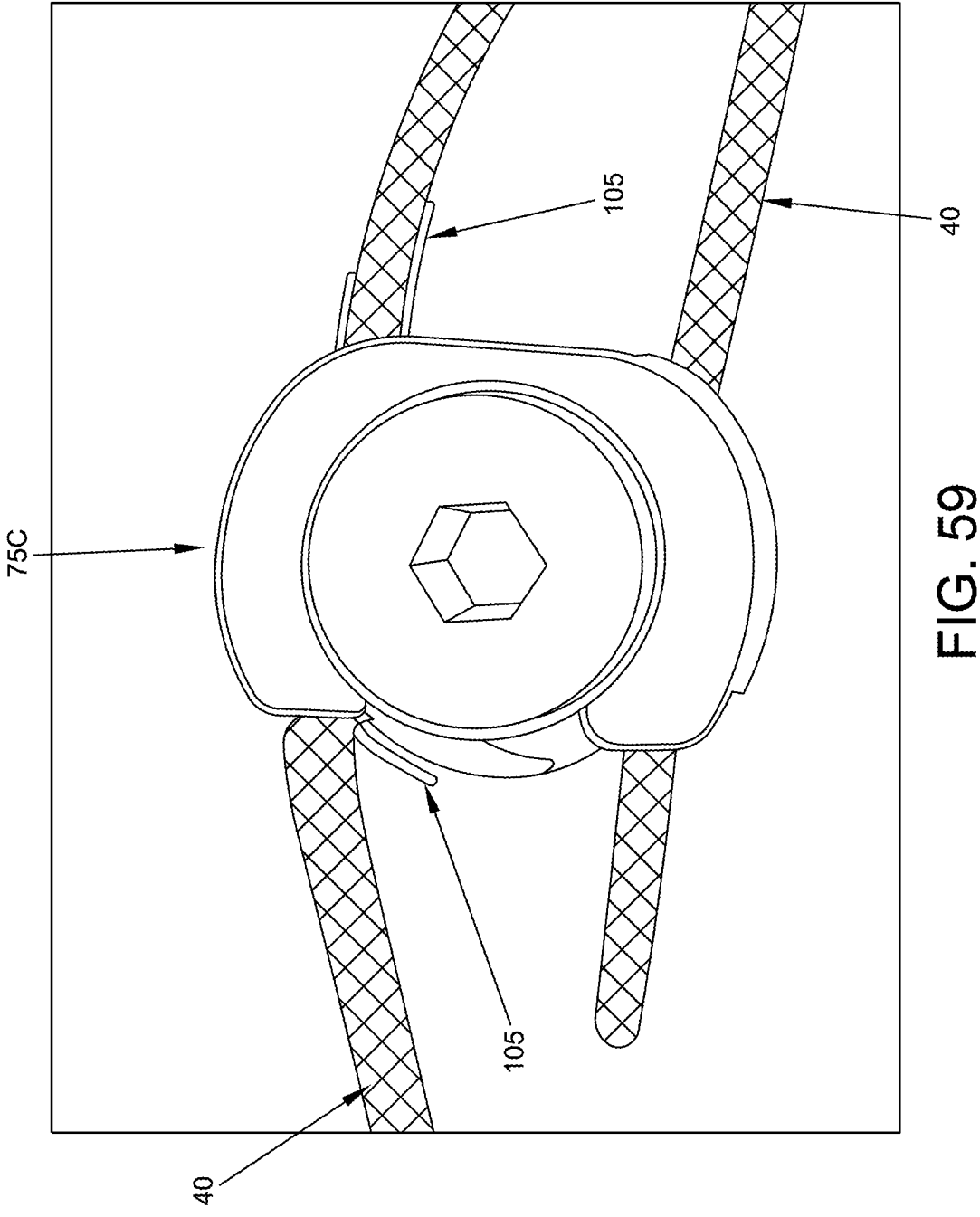
Figure 60:
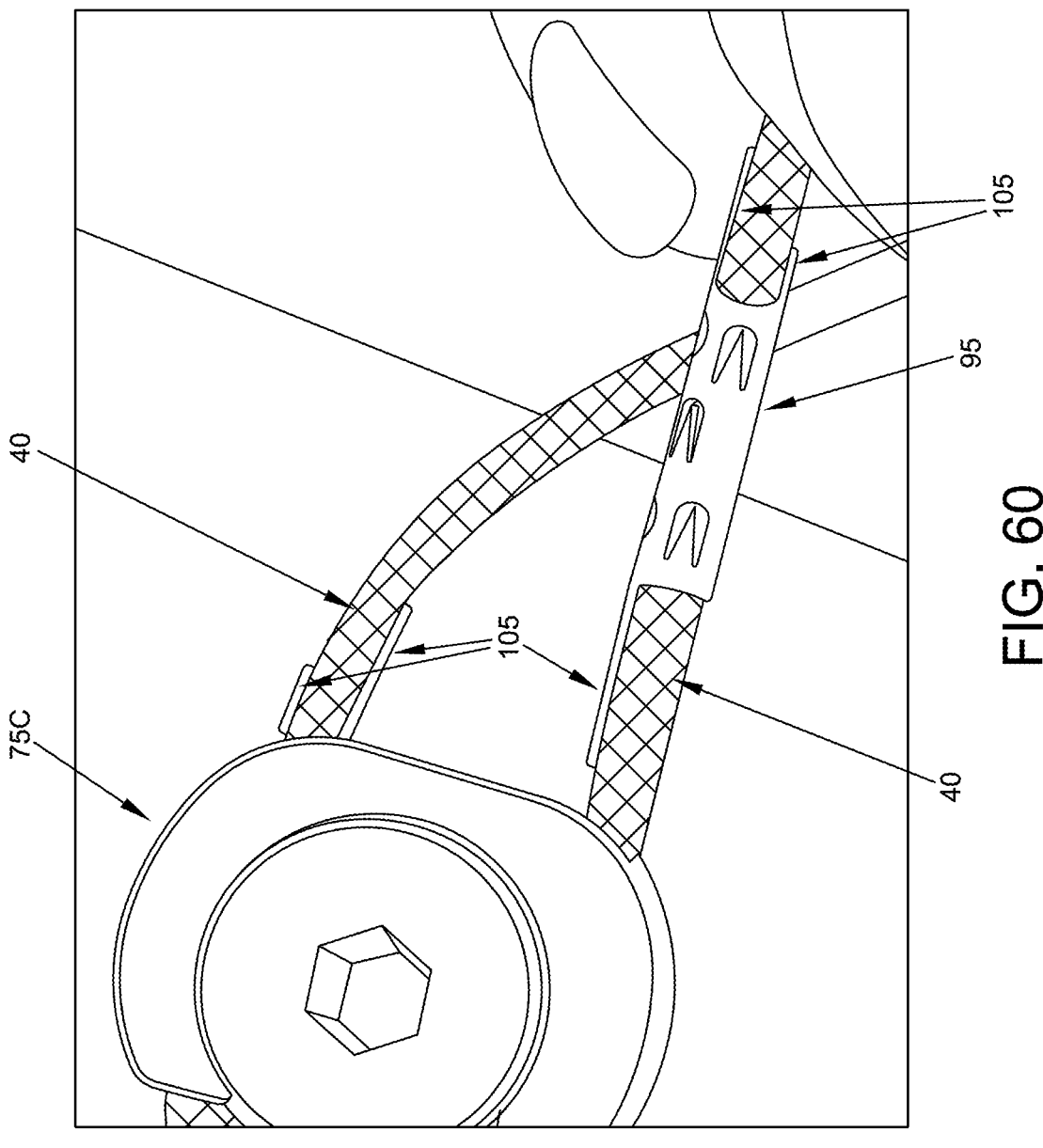
Figure 61:
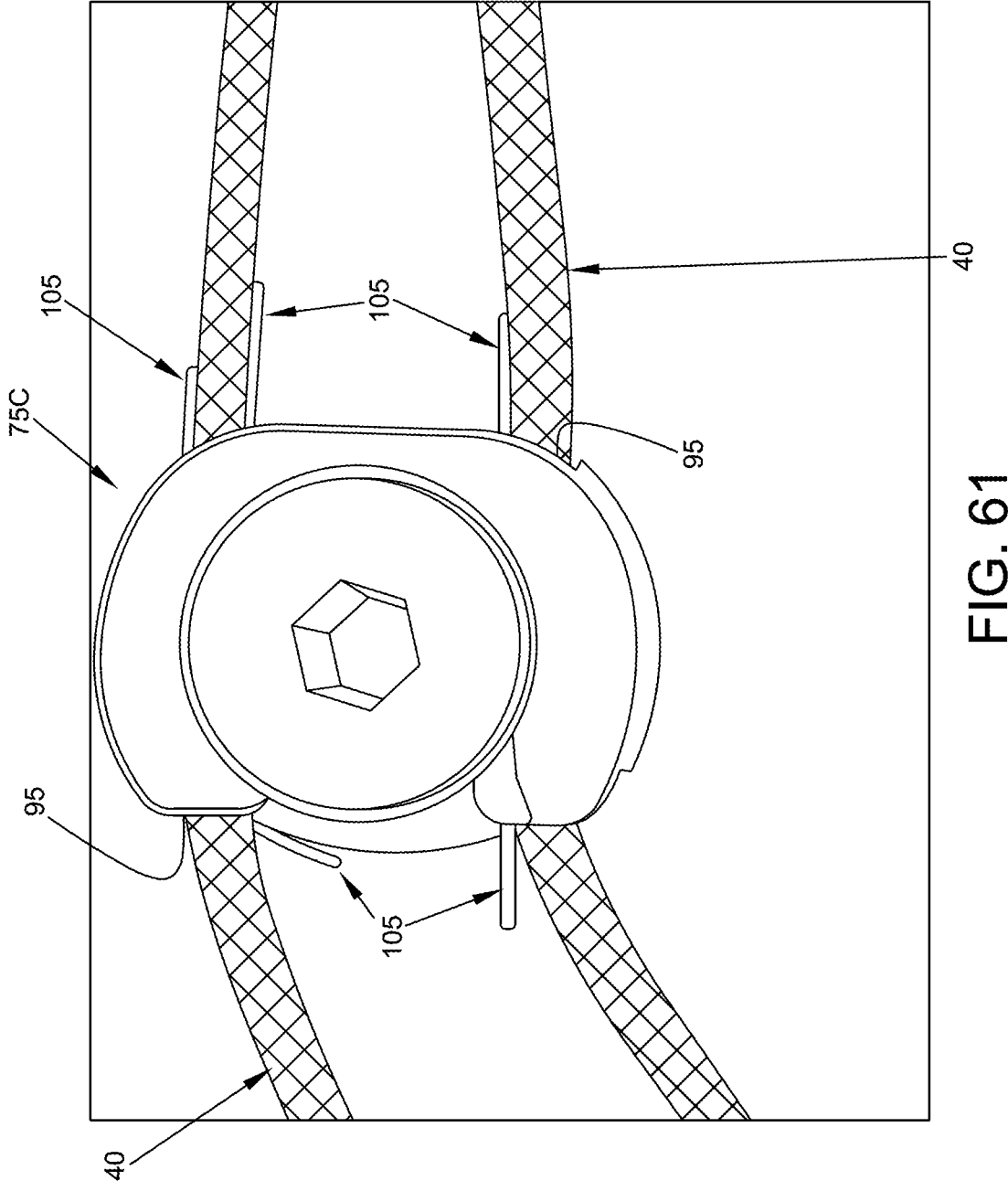
Figures 62, 63, 64, 65:
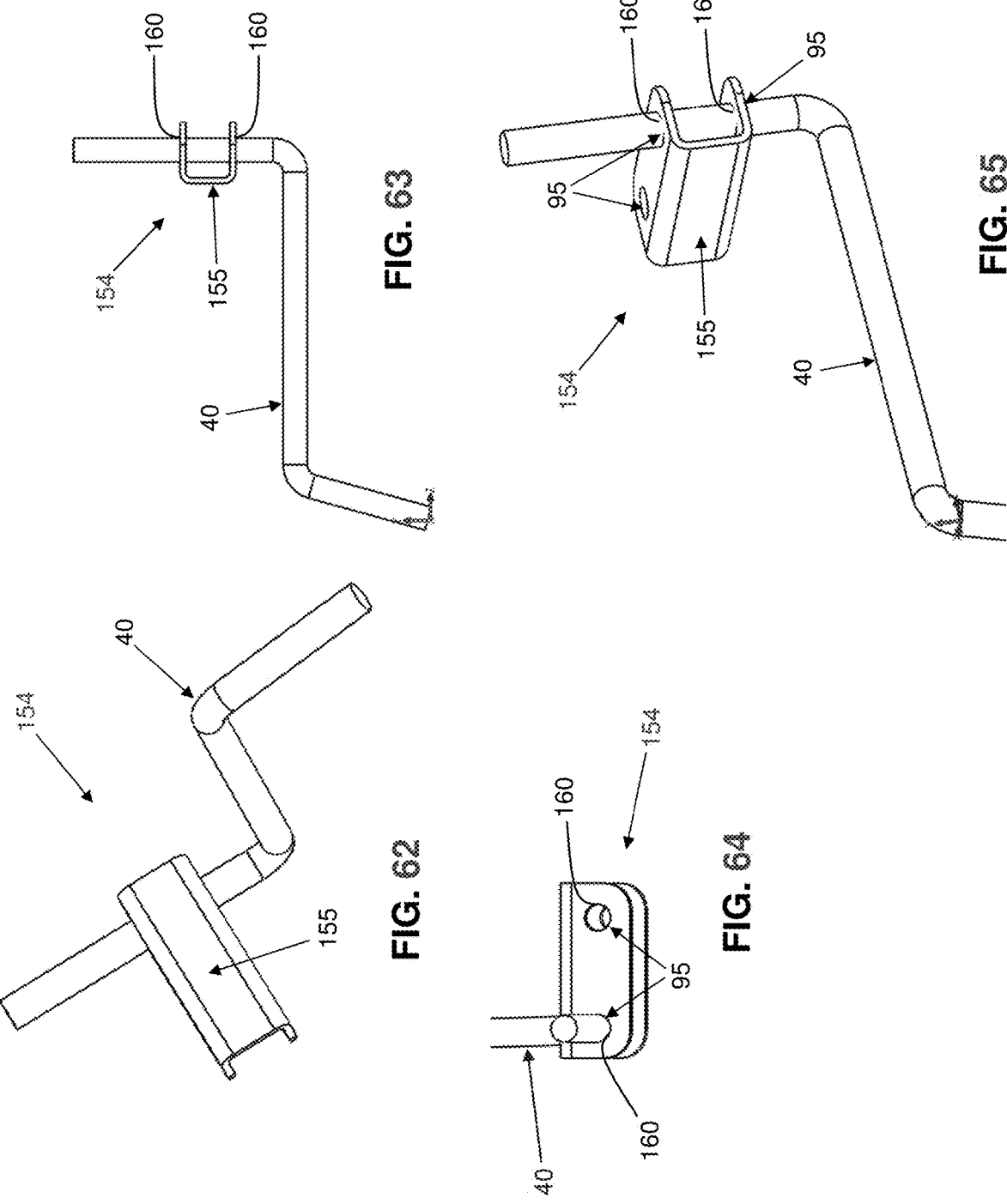
FIGS. 62-65 are various schematic views of a component which may be incorporated into a suture-locking washer, wherein the component incorporates a suture-securing mechanism.

Alternatively, in another form of the invention, sling 40 may be passed through suture-securing mechanism 95 before suture-securing mechanism 95 is mounted to suture-locking washer 75C (or to suture-locking washers 75, 75A or 75B). More particularly, with this approach, suture-securing mechanisms 95 are mounted to sling 40, e.g., a suture (FIG. 58), the free ends of sling 40 (e.g., the free ends of a suture) are threaded through holes 103 in suture-locking washer 75C (FIG. 59), and then suture-securing mechanisms 95 are "towed" into place within holes 103 (FIG. 60) and secured to the suture-locking washer (FIG. 61).

Component Which May Be Incorporated Into a Suture-Locking Washer

FIGS. 62-65 show a component which may be incorporated into a suture-locking washer, wherein the component incorporates a suture-securing mechanism. More particularly, in this form of the invention, there is provided a component 154 that comprises a housing 155 which includes a pair of openings 160 which receive suture-securing mechanisms 95. If desired, a suture-securing mechanism 95 may be disposed in an opening 160, or a suture-securing mechanism 95 may be mounted in, and extend between, two aligned openings 160. Furthermore, some of the openings 160 may omit a suture-securing mechanism 95 (i.e., some of the openings 160 may comprise a smooth-walled bore). Component 154 is configured so that it may be incorporated into a suture-locking washer of the sort described above, whereby to adjustably secure a sling (e.g., a suture) 40 to component 154, and hence to adjustably secure a sling (e.g., a suture) 40 to a suture-locking washer and bone anchor.

Suture-Locking Washer Which is Not Mounted to a Bone Anchor

Figure 66:
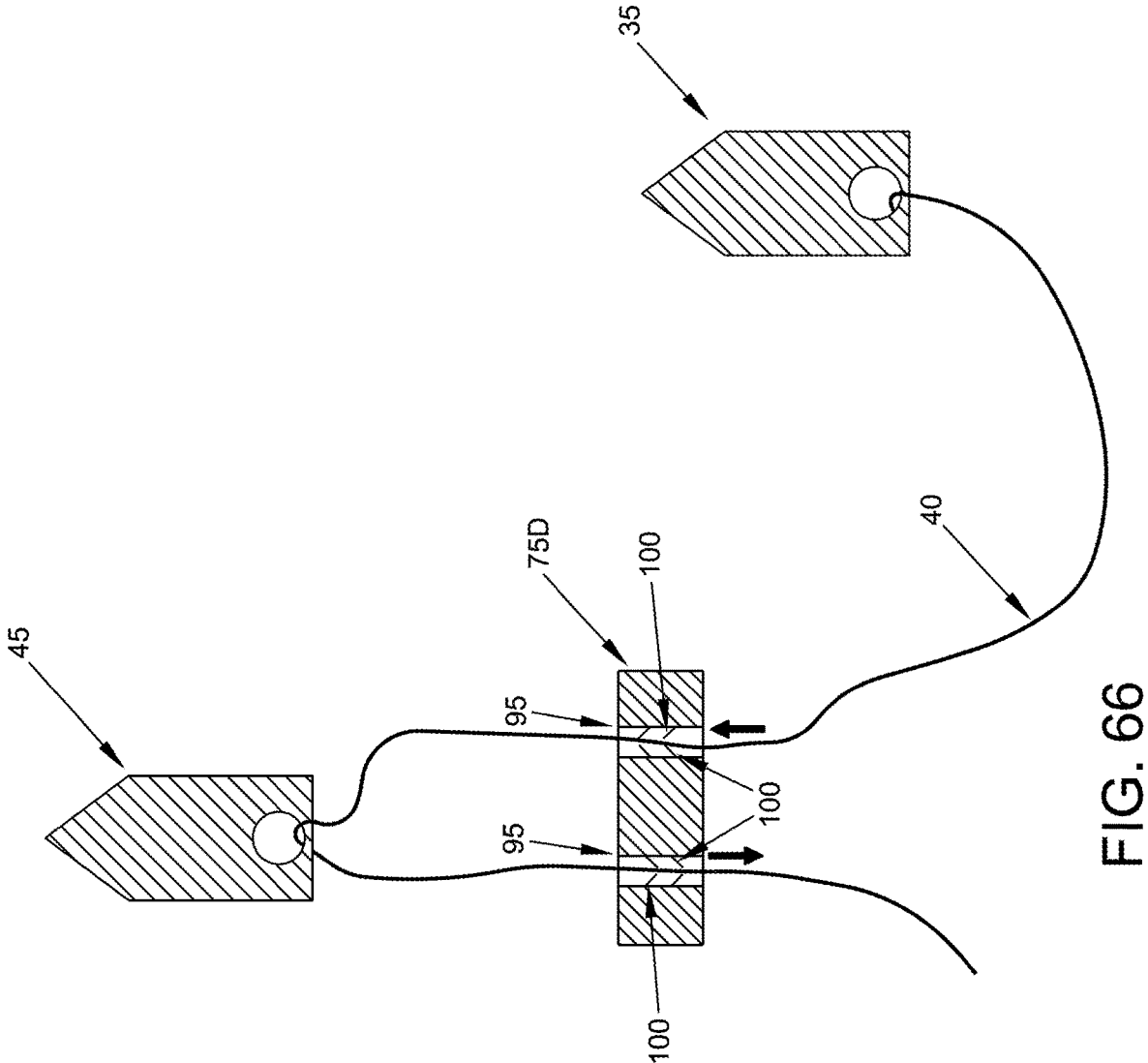
FIG. 66 is a schematic view showing another novel sling suspension system formed in accordance with the present invention.

In another form of the invention, and looking now at FIG. 66, sling suspension system 30 may comprise an index metacarpal anchor 35 for deployment in index metacarpal 25, a thumb metacarpal anchor 45 for deployment in thumb metacarpal 15, and a sling 40 (e.g., a suture) for securing thumb metacarpal anchor 45 to index metacarpal anchor 35. In this form of the invention, sling 40 is secured to index metacarpal anchor 35, and sling 40 is slidable relative to thumb metacarpal anchor 45. A suture-locking washer 75D is slidably mounted onto sling 40. Suture-locking washer 75D comprises two suture-securing mechanisms 95, wherein the two suture-securing mechanisms 95 are configured to allow suture movement in opposite directions. More particularly, the suture-securing mechanism 95 receiving the portion of sling 40 extending between index metacarpal anchor 35 and thumb metacarpal anchor 45 allows suture movement toward thumb metacarpal anchor 45 but prevents suture movement toward index metacarpal anchor 35, and the portion of sling 40 extending between thumb metacarpal anchor 45 and the other suture-securing mechanism 95 allows suture movement away from thumb metacarpal anchor 45 but prevents suture movement toward thumb metacarpal anchor 45.

In this form of the invention, index metacarpal anchor 35 is disposed in index metacarpal 25, thumb metacarpal anchor 45 is disposed in thumb metacarpal 15, thumb metacarpal 15 is positioned in the appropriate location relative to index metacarpal 25, and then the free end of sling 40 is pulled as suture-locking washer 75D is advanced towards thumb metacarpal anchor 45 until suture-locking washer 75D is seated against thumb metacarpal 15. The locking engagement of suture-locking washer 75D with sling 40 keeps thumb metacarpal 15 locked against movement relative to index metacarpal 25.

Bone Anchor Comprising Suture-Securing Mechanisms

If desired, suture-securing mechanisms 95 may be incorporated directly into a bone anchor, e.g., holes 103 may be formed in the head of a bone anchor, and suture-securing mechanisms 95 may be disposed in holes 103. In this way, a bone anchor may be provided with a suture-locking facility without requiring the use of a separate element (i.e., a suture-locking washer).

Other Medical Devices Comprising Suture-Securing Mechanisms

If desired, suture-securing mechanisms 95 may be incorporated into other medical devices, e.g., bone plates, etc. In this form of the invention, holes 103 may be formed in the medical device, and suture-securing mechanisms 95 may be disposed in holes 103. In this way, a medical device may be provided with a suture-locking facility.

Applications

In addition to the foregoing, it should also be appreciated that the present invention may be used in basal joint arthroplasties which may be conducted for purposes other than alleviating basal joint arthritis, e.g., such as in the case of disease and/or trauma.

Also, suture-locking washer 75 (and suture-locking washers 75B, 75C and 75D) and suture-securing mechanisms 95 (and suture-securing mechanism 95B) may be applicable to alternative applications that use bone anchors or other applications which use implantable medical devices. By way of example but not limitation, suture-locking washers 75 (and suture-locking washers 75B, 75C and 75D) may be utilized to provide knotless suture attachment to screw anchors during virtually all orthopedic procedures requiring fixation of suture, utilized to reposition or support the position of tendon, or other soft tissue, relative to bone.

Figure 67:
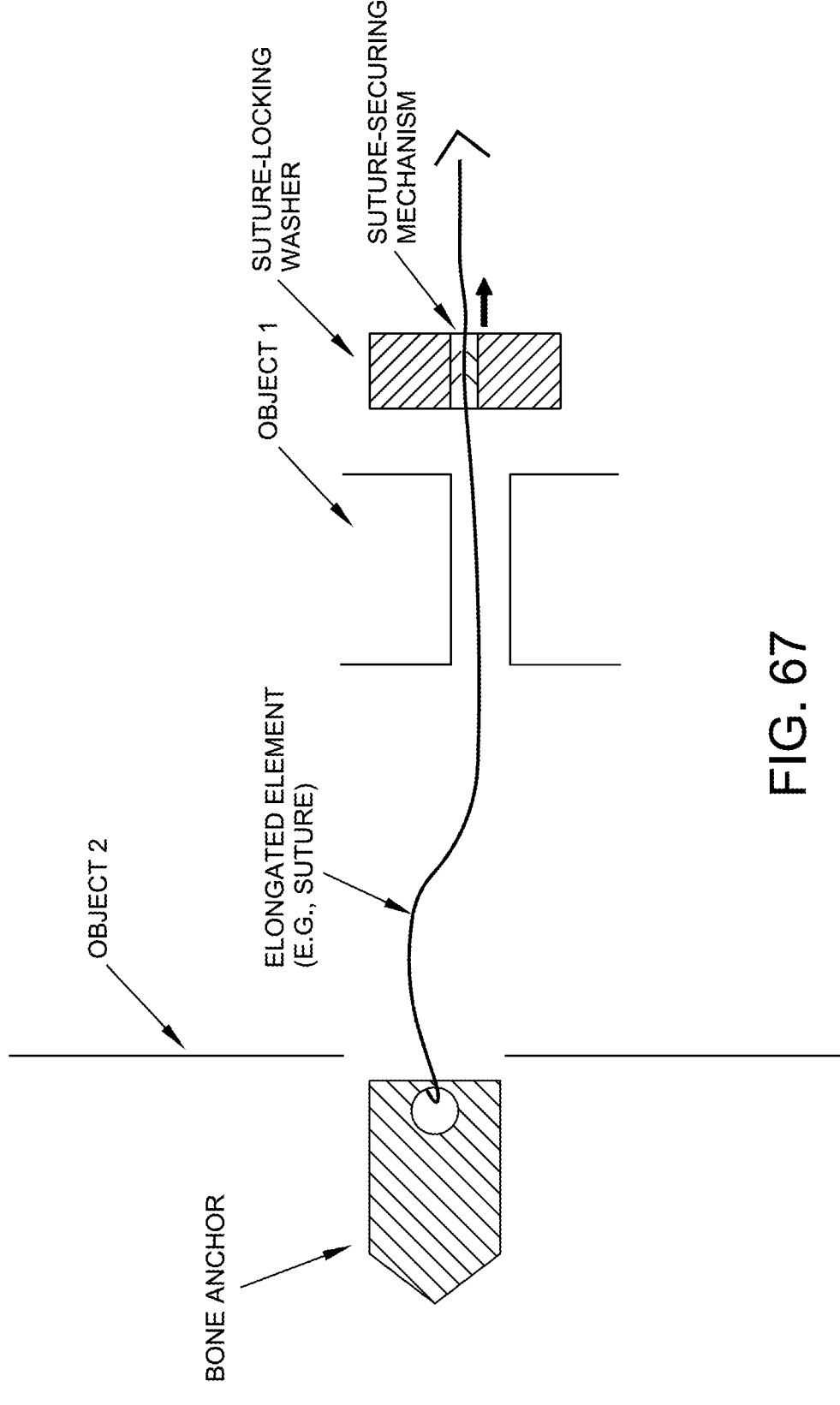
FIG. 67 is a schematic view showing another novel system formed in accordance with the present invention and useful for effecting a surgical repair.

More particularly, and looking now at FIG. 67, where it is desired to secure a first object (e.g., a bone, soft tissue, etc.) to a second object (e.g., a bone, etc.), a bone anchor is disposed in the second object, the suture extending away from the bone anchor is passed through an opening in the first object, and then the suture-locking washer 75 (or suture locking washer 75B, 75C or 75D), containing a suture-securing mechanism 95 (or suture-securing mechanism 95B), is loaded onto the free end of the suture and pushed against the far side of the first object so as to cinch the first object against the second object. In this way, the bone anchor, suture and suture-locking washer can be used to secure the first object to the second object.

Applications of the apparatus and methods of the present invention include, but are not limited to rotator cuff repair, tenodesis, medial (ulnar) collateral ligament reconstruction (the "Tommy John Procedure"), lateral ulnar collateral ligament reconstruction, Carpal instability treated with scapholunate and lunotriquetral ligament reconstructions (Blatt Capsulodesis), thumb carpometacarpal arthroplasty (ligament reconstruction with tendon interposition-LRTI), chronic thumb ulnar collateral ligament reconstruction (Gamekeeper's thumb), chronic thumb radial collateral ligament reconstruction, finger metacarpophalangeal ligament reconstruction, medial collateral ligament repair/reconstructions with autograft or allograft, lateral collateral ligament repair/reconstruction with autograft or allograft, posterolateral reconstruction with autograft or allograft, various lateral collateral ligament reconstructions (Watson-Jones/Chrisman Snook), or other applications involving securing suture strand(s) to bone in order to secure tendons or other soft tissue to bone.

Figure 68:
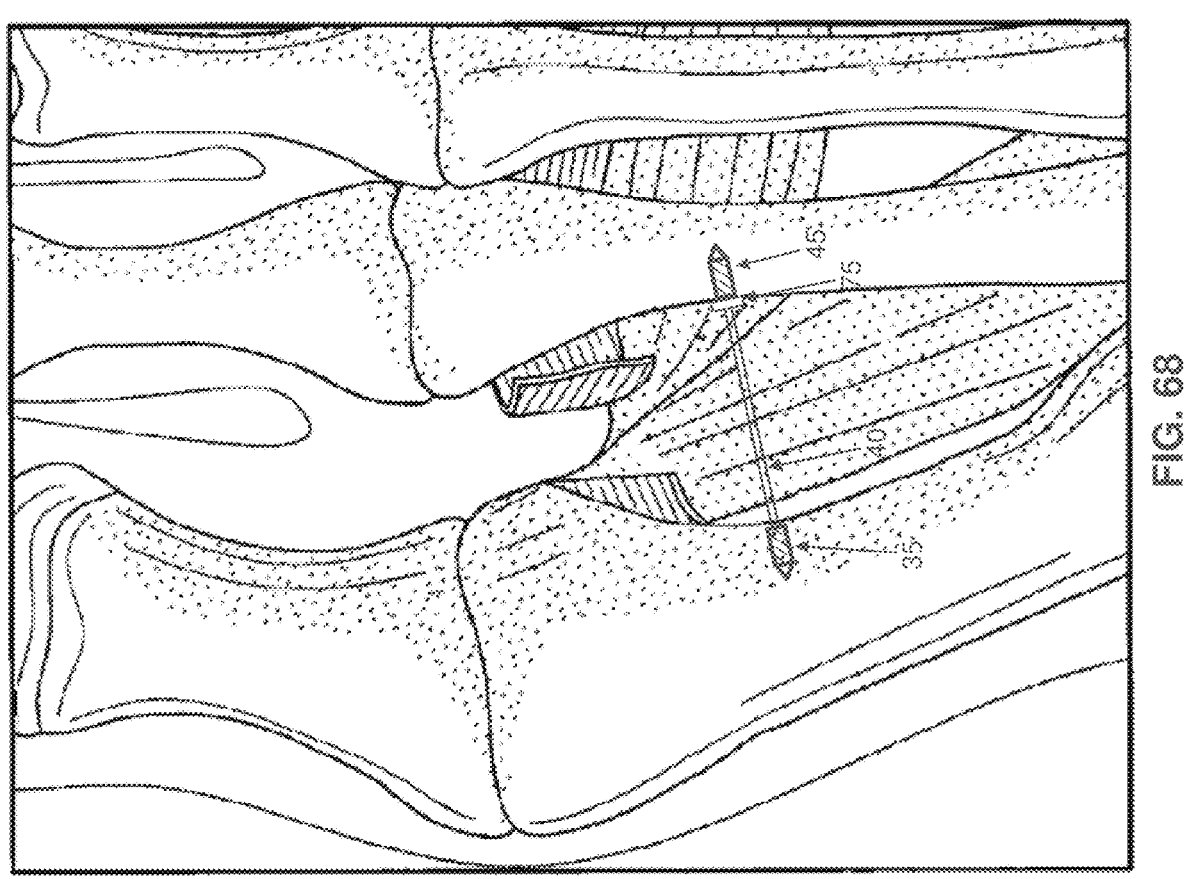
FIG. 68-72 are schematic views showing exemplary surgical repairs performed in accordance with the present invention.
Figure 69:
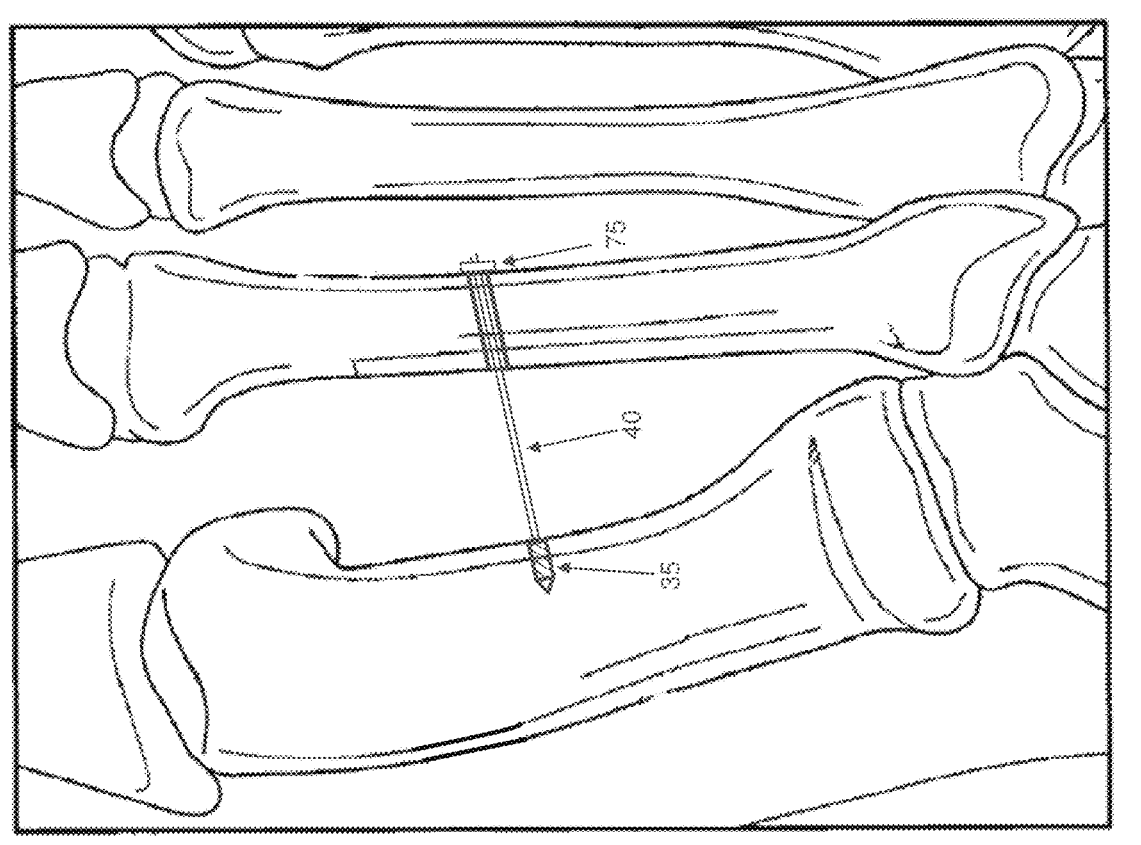
Figure 70:
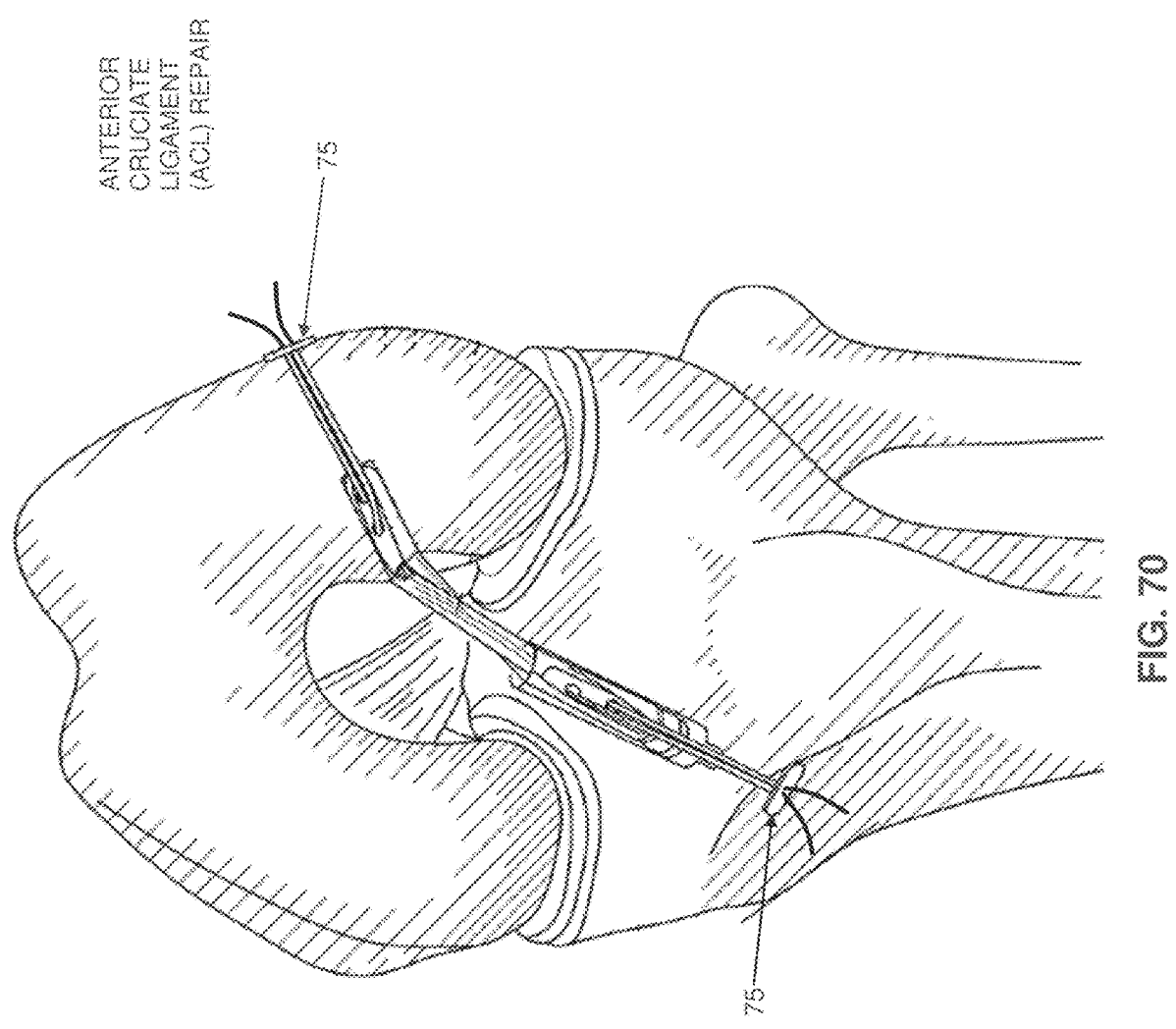
Figure 71:
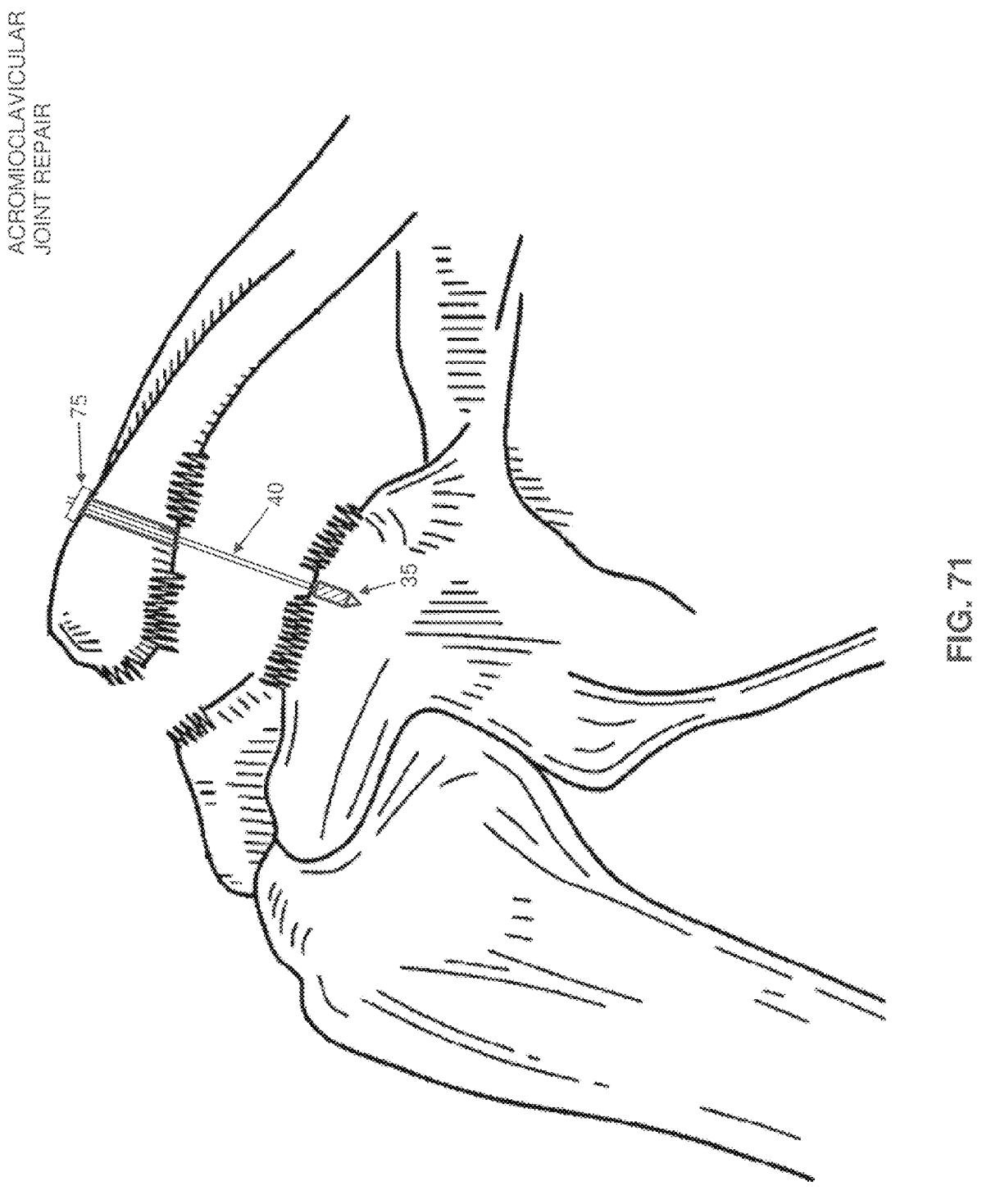
Figure 72:
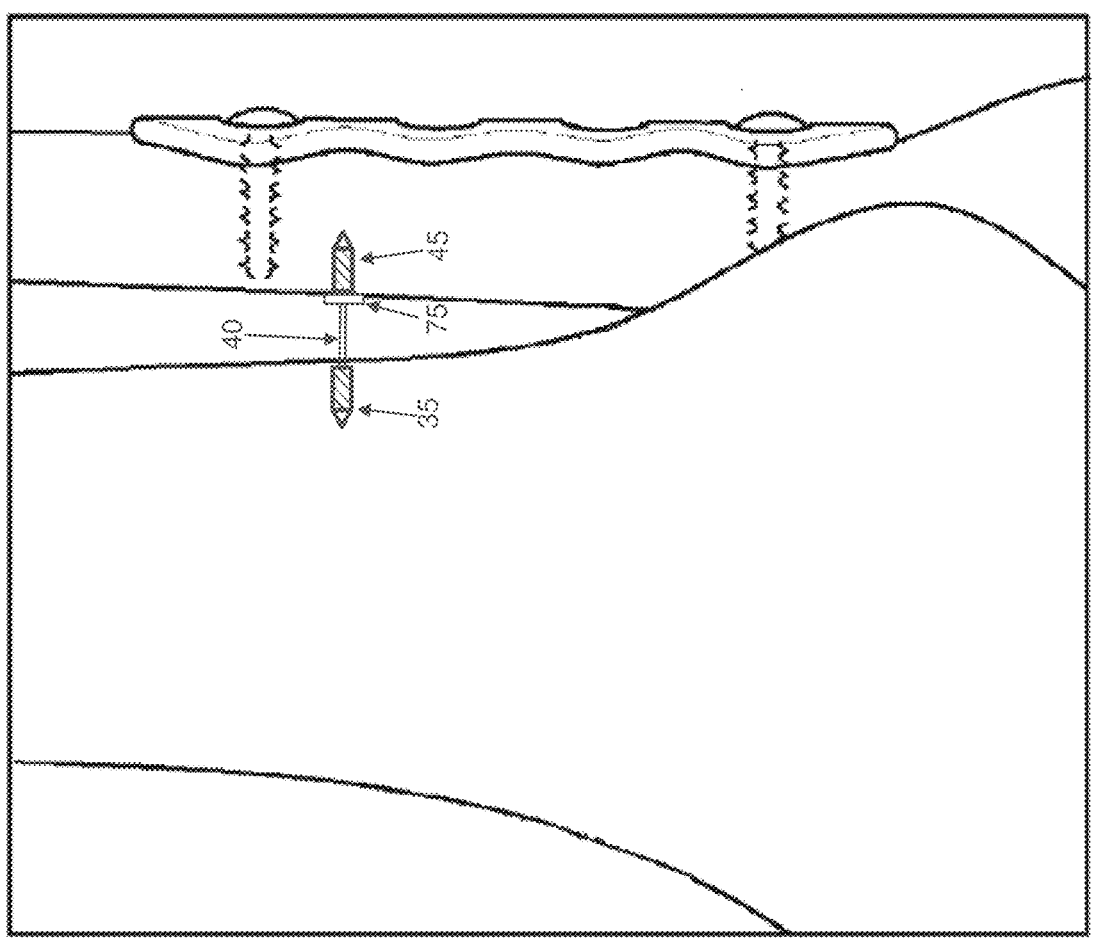

By way of example but not limitation, see FIG. 68 which shows a hallux valgus repair using the apparatus and methods of the present invention; FIG. 69 which shows another hallux valgus repair using the apparatus and methods of the present invention; FIG. 70 which shows an anterior cruciate ligament (ACL) repair using the apparatus and methods of the present invention; FIG. 71 which shows acromioclavicular joint repair using the apparatus and methods of the present invention; and FIG. 72 which shows an ankle syndesmosis repair using the apparatus and methods of the present invention.

Nomenclature

In the foregoing disclosure, there is disclosed a sling suspension system for supporting the thumb of a patient after basal joint arthroplasty, and the sling suspension system is disclosed as comprising a sling which may comprise a suture. In addition, in the foregoing disclosure, there are disclosed apparatus and methods for effecting other orthopedic repairs, wherein the apparatus comprises a sling or suture. In view of this, in order to render the text more readable, various components have been referred to herein in the context of suture, e.g., washers 75A, 75B, 75C and 75D are sometimes referred to as "suture-locking" washers, mechanisms 95 and 95B are sometimes referred to as "suture-securing" mechanisms, and elements 100 are sometimes referred to as "suture-holding" elements.

However, it should be appreciated that the apparatus and methods of the present invention are applicable to a wide range of applications where elongated elements other than suture per se need to be secured in place. By way of example but not limitation, such other elongated elements might comprise non-suture filaments. It will be appreciated by those skilled in the art that washers 75A, 75B, 75C and 75D, mechanisms 95 and 95B, and elements 100 are equally capable of locking or securing or holding non-suture elongated elements and filaments. Therefore, it will be appreciated that suture-locking washers 75A, 75B, 75C and 75D may also be appropriately referred to as "elongated element-locking" washers or "filament-locking" washers, suture-securing mechanisms 95 and 95B may also be appropriately referred to as "elongated element-securing" mechanisms or "filament-securing" mechanisms, and suture-holding elements 100 may also be appropriately referred to as "elongated element-holding" elements or "filament-holding" elements.

Therefore, where the context so admits, suture-locking washers 75A, 75B, 75C and 75D should also be considered to be "elongated element-locking" washers or "filament-locking" washers, suture-securing mechanisms 95 and 95B should also be considered to be "elongated element-securing" mechanisms or "filament-securing" mechanisms, and suture-holding elements 100 should also be considered to be "elongated element-holding" elements or "filament-holding" elements.

Modifications

It is to be appreciated that the present invention is by no means limited to the particular constructions herein disclosed and/or shown in the drawings, but also comprises any modifications or equivalents within the scope of the invention. Although the present invention has been described in terms of the preferred embodiments above, numerous modifications and/or additions to the above-described preferred embodiments would be readily apparent to one skilled in the art.

What is claimed is:

1. Apparatus for securing a first anatomical object to a second anatomical object, said apparatus comprising:
   a washer body comprising:
      a central bore extending through the washer body, wherein the central bore is configured to receive an anchor, wherein a portion of the washer body comprises a passageway opening into the central bore of the washer body;
      a first opening extending through the washer body on one side of the passageway; and
      a second opening extending through the washer body on an opposite side of the passageway; and
   a first tubular structure disposed in the first opening of the washer body and a second tubular structure disposed in the second opening of the washer body, wherein the first tubular structure and the second tubular structure each comprise a side wall defining a filament passageway, a portion of the side wall of the tubular structure projecting into the filament passageway so as to provide one-way movement of a filament extending through the filament passageway, wherein the first tubular structure comprises at least one end projection configured to be bent into engagement with a portion of the washer body adjacent to the first opening to secure the first tubular structure in the first opening in the washer body, and further wherein the second tubular structure comprises at least one end projection configured to be bent into engagement with a portion of the washer body adjacent to the second opening to secure the second tubular structure in the second opening in the washer body.

2. Apparatus according to claim 1 wherein the end projections are configured to extend out of the first and second openings in said washer body to secure the first and second tubular structures in the first and second openings in said washer body.

3. Apparatus according to claim 1 wherein the first and second openings each comprise a stepped bore defining a shoulder, and further wherein the first and second tubular structures engage said shoulder.

4. Apparatus according to claim 1 wherein the washer body is a bone anchor.

5. Apparatus according to claim 1 wherein said apparatus further comprises the filament extending through the filament passageway.

6. A method for securing a first anatomical object to a second anatomical object, said method comprising:
   providing apparatus for securing the first anatomical object to the second anatomical object, said apparatus comprising:
      a washer body comprising:
         a central bore extending through the washer body, wherein the central bore is configured to receive an anchor, wherein a portion of the washer body comprises a passageway opening into the central bore of the washer body;
         a first opening extending through the washer body on one side of the passageway; and
         a second opening extending through the washer body on an opposite side of the passageway; and
      a first tubular structure disposed in the first opening of the washer body and a second tubular structure disposed in the second opening of the washer body, wherein the first tubular structure and the second tubular structure each comprise a side wall defining a filament passageway, a portion of the side wall of the tubular structure projecting into the filament passageway, wherein the first tubular structure comprises at least one end projection configured to be bent into engagement with a portion of the washer body adjacent to the first opening to secure the first tubular structure in the first opening in the washer body, and further wherein the second tubular structure comprises at least one end projection configured to be bent into engagement with a portion of the washer body adjacent to the second opening to secure the second tubular structure in the second opening in the washer body;
   passing a filament through said filament passageway;
   associating one end of said filament with the second anatomical object and associating said washer body with the first anatomical object; and
   moving said filament through said filament passageway so as to shorten the length of said filament extending between the first anatomical object and the second anatomical object so as to fixedly connect the first anatomical object to the second anatomical object, wherein the portion of the sidewall of the tubular structure projecting into the filament passageway provides one-way movement of the filament.

7. A method according to claim 6 wherein said washer body is secured to the first anatomical object using a bone anchor.

8. A method according to claim 6 wherein said washer body is secured to the first anatomical object by positioning said washer body against a far surface of the first anatomical object.

9. A method according to claim 8 wherein said filament extends to the far surface of the first anatomical object by passing said filament through a through-hole formed in the first anatomical object.

10. A method according to claim 6 wherein said filament is secured to the second anatomical object using a bone anchor.

11. A method according to claim 6 wherein said filament is secured to the second anatomical object by positioning a second washer body against a far surface of the second anatomical object.

12. A method according to claim 11 wherein said filament extends to the far surface of the second anatomical object by passing said filament through a through-hole formed in the second anatomical object.

13. Apparatus for securing a first anatomical object to a second anatomical object, the apparatus comprising:

a bone anchor comprising an elongated shaft having a distal end, a proximal end and an enlarged head at the proximal end of the elongated shaft;

a washer body comprising:

a central bore extending through the washer body, wherein the central bore is configured to receive the elongated shaft of the bone anchor, wherein a portion of the washer body comprises a passageway opening into the central bore of the washer body;

a first opening extending through the washer body on one side of the passageway; and a second opening extending through the washer body on an opposite side of the passageway; and a first tubular structure disposed in the first opening of the washer body and a second tubular structure disposed in the second opening of the washer body, wherein the first tubular structure and the second tubular structure each comprise a side wall defining a filament passageway, a portion of the side wall of the tubular structure projecting into the filament passageway so as to secure a filament extending through the filament passageway, wherein the first tubular structure comprises at least one end projection configured to be bent into engagement with a portion of the washer body adjacent to the first opening to secure the first tubular structure in the first opening in the washer body, and further wherein the second tubular structure comprises at least one end projection configured to be bent into engagement with a portion of the washer body adjacent to the second opening to secure the second tubular structure in the second opening in the washer body.

14. A method for securing a first anatomical object to a second anatomical object, the method comprising:

providing apparatus for securing the first anatomical object to the second anatomical object, the apparatus comprising:

a bone anchor comprising an elongated shaft having a distal end, a proximal end and an enlarged head at the proximal end of the elongated shaft;

a washer body comprising:

a central bore extending through the washer body, wherein the central bore is configured to receive the elongated shaft of the bone anchor, wherein a portion of the washer body comprises a passageway opening into the central bore of the washer body;

a first opening extending through the washer body on one side of the passageway; and a second opening extending through the washer body on an opposite side of the passageway; and a first tubular structure disposed in the first opening of the washer body and a second tubular structure disposed in the second opening of the washer body, wherein the first tubular structure and the second tubular structure each comprise a side wall defining a filament passageway, a portion of the side wall of the tubular structure projecting into the filament passageway, wherein the first tubular structure comprises at least one end projection configured to be bent into engagement with a portion of the washer body adjacent to the first opening to secure the first tubular structure in the first opening in the washer body, and further wherein the second tubular structure comprises at least one end projection configured to be bent into engagement with a portion of the washer body adjacent to the second opening to secure the second tubular structure in the second opening in the washer body;

passing a filament through the filament passageway;

mounting the washer body to the bone anchor;

connecting one end of the filament with the first anatomical object and inserting the apparatus into the second anatomical object; and moving the filament through the filament passageway so as to shorten the length of the filament extending between the first anatomical object and the second anatomical object so as to fixedly connect the first anatomical object to the second anatomical object, wherein the portion of the sidewall of the tubular structure projecting into the passageway secures the filament extending through the filament passageway.

* * * * *